(12) United States Patent
Rotenstreich et al.

(10) Patent No.: US 11,076,757 B2
(45) Date of Patent: *Aug. 3, 2021

(54) SYSTEM AND METHOD FOR PERFORMING OBJECTIVE PERIMETRY AND DIAGNOSIS OF PATIENTS WITH RETINITIS PIGMENTOSA AND OTHER OCULAR DISEASES

(71) Applicant: TEL HASHOMER MEDICAL RESEARCH INFRASTRUCTURE AND SERVICES, LTD, Ramat Gan (IL)

(72) Inventors: Ygal Rotenstreich, Kfar Bilu (IL); Ifat Sher, Shoham (IL)

(73) Assignee: TEL HASHOMERMEDICAL RESEARCH INFRASTRUCTURE AND SERVICES, LTD, Ramat Gan (IL)

( * ) Notice: Subject to any disclaimer, the term of this patent is extended or adjusted under 35 U.S.C. 154(b) by 318 days.

This patent is subject to a terminal disclaimer.

(21) Appl. No.: 16/068,994

(22) PCT Filed: Jan. 12, 2017

(86) PCT No.: PCT/US2017/013122
§ 371 (c)(1),
(2) Date: Jul. 10, 2018

(87) PCT Pub. No.: WO2017/123710
PCT Pub. Date: Jul. 20, 2017

(65) Prior Publication Data
US 2019/0008381 A1    Jan. 10, 2019

Related U.S. Application Data

(63) Continuation of application No. PCT/US2017/013122, filed on Jan. 12, 2017.
(Continued)

(51) Int. Cl.
*A61B 3/11* (2006.01)
*A61B 3/14* (2006.01)
(Continued)

(52) U.S. Cl.
CPC ............ *A61B 3/112* (2013.01); *A61B 3/0008* (2013.01); *A61B 3/0025* (2013.01); *A61B 3/024* (2013.01); *A61B 3/11* (2013.01); *A61B 3/14* (2013.01)

(58) Field of Classification Search
CPC ....... A61B 3/0008; A61B 5/163; A61B 5/112; A61B 3/0025; A61B 3/024; A61B 3/11; A61B 3/14
See application file for complete search history.

(56) References Cited

U.S. PATENT DOCUMENTS

| 5,114,222 A | 5/1992 | Cornsweet |
| 5,422,690 A | 6/1995 | Rothberg et al. |

(Continued)

FOREIGN PATENT DOCUMENTS

| EP | 1790281 A1 | 5/2007 |
| JP | 2004216118 A | 8/2004 |

(Continued)

OTHER PUBLICATIONS

PCT Search Report for International Application No. PCT/US2017/013122 dated Jun. 2, 2017, 4 pp.

(Continued)

*Primary Examiner* — Patrick Fernandes
(74) *Attorney, Agent, or Firm* — The Roy Gross Law Firm, LLC; Roy Gross

(57) ABSTRACT

A system and method for determining a state of health of an eye using a pupillometer is provided comprising an ocular fixture, a testing compartment, a camera, and a controller. The testing compartment comprises a plurality of chromatic beam emitters arranged about a visual field. The ocular fixture is positioned to facilitate exposure of light sensitive ocular structures of the eye to a chromatic stimuli. The camera is positioned to record temporal pupil responses of the eye. The controller controls emission wavelength, intensity, and duration of the chromatic beam emitters. The controller processes temporal pupil response data to generate signals representative of the eye positioned at the ocular fixture in response to the chromatic stimuli at a plurality of locations in the visual field. The method comprises driving (Continued)

the chromatic beam emitters with the controller to generate signals using chromatic stimuli and determining the state of health of the eye.

20 Claims, 32 Drawing Sheets

Related U.S. Application Data

(60) Provisional application No. 62/277,520, filed on Jan. 12, 2016.

(51) Int. Cl.
*A61B 3/024* (2006.01)
*A61B 3/00* (2006.01)

(56) References Cited

U.S. PATENT DOCUMENTS

| | | | |
|---|---|---|---|
| 5,459,536 A | 10/1995 | Shalon et al. | |
| 5,490,098 A | 2/1996 | Kardon | |
| 5,610,673 A | 3/1997 | Rafal et al. | |
| 5,805,271 A | 9/1998 | Kirschbaum et al. | |
| 6,022,109 A | 2/2000 | Dal Santo | |
| 6,116,736 A | 9/2000 | Stark et al. | |
| 6,260,968 B1 | 7/2001 | Stark et al. | |
| 6,820,979 B1 | 11/2004 | Stark et al. | |
| 7,083,280 B2 | 8/2006 | Hakamata | |
| 7,118,217 B2 | 10/2006 | Kardon et al. | |
| 7,147,327 B2 | 12/2006 | Stark et al. | |
| 7,216,982 B2 | 5/2007 | Fujimatsu et al. | |
| 7,407,287 B2 | 8/2008 | Hakamata | |
| 7,448,751 B2 | 11/2008 | Kiderman et al. | |
| 7,520,614 B2 | 4/2009 | Joos et al. | |
| 7,614,746 B2 | 11/2009 | Severns | |
| 7,625,087 B2 | 12/2009 | Taylor et al. | |
| 7,665,845 B2 | 2/2010 | Kiderman et al. | |
| 7,670,002 B2 | 3/2010 | Stark et al. | |
| 7,677,728 B2 | 3/2010 | Hirohara et al. | |
| 7,712,899 B2 | 5/2010 | Tanassi et al. | |
| 7,731,360 B2 | 6/2010 | MacDougall et al. | |
| 7,753,523 B2 | 7/2010 | Kiderman et al. | |
| 7,802,900 B2 | 9/2010 | Suba | |
| 7,866,818 B2 | 1/2011 | Schroeder et al. | |
| 7,967,442 B2 | 6/2011 | Siminou | |
| 7,976,160 B2 | 7/2011 | Nauche | |
| 7,980,699 B2 | 7/2011 | Neal et al. | |
| 8,016,420 B2 | 9/2011 | Yee et al. | |
| 8,096,658 B2 | 1/2012 | Kikawa et al. | |
| 8,235,526 B2 | 8/2012 | Stark et al. | |
| 8,348,426 B2 | 1/2013 | Tsukada et al. | |
| 8,388,135 B2 | 3/2013 | Hacker et al. | |
| 8,393,734 B2 | 3/2013 | Privitera et al. | |
| 8,500,281 B2 | 8/2013 | Ahn et al. | |
| 8,534,840 B2 | 9/2013 | Siminou | |
| 8,662,667 B2 | 3/2014 | Schuhrke et al. | |
| 8,744,140 B2 | 6/2014 | Baughman et al. | |
| 8,750,575 B2 | 6/2014 | Baughman et al. | |
| 8,807,753 B2 | 8/2014 | Maddess et al. | |
| 8,833,940 B2 | 9/2014 | Yee et al. | |
| 8,911,085 B2 | 12/2014 | Privitera et al. | |
| 9,101,296 B2 | 8/2015 | Schroeder et al. | |
| 9,198,570 B2 | 12/2015 | Siminou, III et al. | |
| 9,220,408 B2 | 12/2015 | Privitera et al. | |
| 2002/0099305 A1* | 7/2002 | Fukushima | A61B 5/163 600/558 |
| 2003/0098951 A1 | 5/2003 | Hakamata | |
| 2004/0105075 A1 | 6/2004 | Kandel et al. | |
| 2004/0246441 A1 | 12/2004 | Stark et al. | |
| 2005/0099601 A1 | 5/2005 | MacDougall et al. | |
| 2005/0270483 A1 | 12/2005 | Fujimatsu et al. | |
| 2006/0106437 A1 | 5/2006 | Czeisler et al. | |
| 2006/0181678 A1 | 8/2006 | Stark et al. | |
| 2006/0181679 A1 | 8/2006 | Hakamata | |
| 2006/0189886 A1 | 8/2006 | Jones et al. | |
| 2007/0121068 A1 | 5/2007 | MacDougall et al. | |
| 2007/0132841 A1 | 6/2007 | MacDougall et al. | |
| 2007/0229760 A1 | 10/2007 | Hirohara et al. | |
| 2008/0024724 A1 | 1/2008 | Todd | |
| 2008/0049186 A1 | 2/2008 | MacDougall et al. | |
| 2008/0049187 A1 | 2/2008 | Joos et al. | |
| 2008/0117384 A1 | 5/2008 | Inakagata et al. | |
| 2008/0198330 A1 | 8/2008 | Taylor | |
| 2008/0234972 A1 | 9/2008 | Tsukada et al. | |
| 2008/0273084 A1 | 11/2008 | MacDougall et al. | |
| 2008/0278685 A1 | 11/2008 | MacDougall et al. | |
| 2008/0284979 A1 | 11/2008 | Yee et al. | |
| 2009/0161090 A1 | 6/2009 | Campbell et al. | |
| 2009/0174865 A1 | 7/2009 | Privitera et al. | |
| 2009/0190093 A1 | 7/2009 | Tanassi et al. | |
| 2009/0213329 A1* | 8/2009 | Kandel | A61B 3/112 351/206 |
| 2010/0149489 A1 | 6/2010 | Kikawa et al. | |
| 2010/0165293 A1 | 7/2010 | Tanassi et al. | |
| 2010/0195049 A1 | 8/2010 | Stark et al. | |
| 2010/0214532 A1 | 8/2010 | Siminou | |
| 2010/0220286 A1 | 9/2010 | Nauche | |
| 2010/0249532 A1 | 9/2010 | Maddess et al. | |
| 2011/0033090 A1 | 2/2011 | Baughman et al. | |
| 2011/0043758 A1 | 2/2011 | Ahn et al. | |
| 2011/0069279 A1 | 3/2011 | Hacker et al. | |
| 2011/0170064 A1 | 7/2011 | Taylor | |
| 2011/0228224 A1 | 9/2011 | Siminou | |
| 2011/0279777 A1 | 11/2011 | Yee et al. | |
| 2011/0299034 A1 | 12/2011 | Walsh et al. | |
| 2012/0008091 A1 | 1/2012 | Stewart | |
| 2012/0127430 A1* | 5/2012 | Rotenstreich | A61B 3/0008 351/210 |
| 2012/0268715 A1 | 10/2012 | Stark et al. | |
| 2012/0274906 A1 | 11/2012 | Privitera et al. | |
| 2013/0011023 A1 | 1/2013 | Baughman et al. | |
| 2013/0033677 A1 | 2/2013 | MacDougall et al. | |
| 2014/0043587 A1 | 2/2014 | Siminou, III et al. | |
| 2014/0347629 A1 | 11/2014 | Donitzky et al. | |
| 2015/0201828 A1 | 7/2015 | Hara | |
| 2015/0245766 A1 | 9/2015 | Rennaker et al. | |
| 2015/0282704 A1 | 10/2015 | Maddess et al. | |
| 2015/0297074 A1 | 10/2015 | Privitera et al. | |
| 2015/0342495 A1 | 12/2015 | Davis et al. | |

FOREIGN PATENT DOCUMENTS

| | | |
|---|---|---|
| RU | 2508898 C2 | 2/2012 |
| WO | 2015063598 A1 | 5/2015 |
| WO | 2015120438 A1 | 8/2015 |

OTHER PUBLICATIONS

PCT Written Opinion for International Application No. PCT/US2017/013122 dated Jun. 2, 2017, 7 pp.
PCT Preliminary Report on Patentability for International Application No. PCT/US2017/013122 dated Jul. 17, 2018, 8 pp.
Sharma et al (2008) Diagnostic tools for glaucoma detection and management, Surv Opthalmol 53 Suppl 1S17-32.
Ross et al (1984) Variability of visual field measurements in Normal Subjects with retinitis pigmentosa, Arch Ophthalmol, vol. 102, pp. 1004-1010.
Grover et al (1998) Patterns of visual field progression in patients with retinitis pigmentosa, Ophthalmology, 105(6):1069-75.
Trope et al (1987) A comparison of goldmann and humphrey automated perimetry in patients with glaucoma, Br J Ophthalmol, 71(7):489-93.
Kim et al (2007) Intersession repeatability of humphrey perimetry measurements in patients with retinitis pigmentosa, Invest Ophtalmol Vis Sci, 48(10):4720-4.
Seiple et al (2004) Test-retest reliability of the multifocal electroretinogram and humphrey visual fields in patients with retinitis pigmentosa, Documenta ophthalmologica, 109(3):255-72.
Heijl et al (1989) Test-retest variability in glaucomatous visual fields, Am J Ophthalmol, 108(2):130-5.

(56) References Cited

OTHER PUBLICATIONS

Artes et al (2002) Properties of perimetric threshold estimates from full threshold, SITA standard, and SITA fast strategies, Invest Ophthalmol Visual Sci, 43(8):2654-9.
Turalba et al (2010) A review of current technology used in evaluating visual function in glaucoma, Semin Opthalmol, 25(5-6):309-16.
Chauhan et al (2008) Practical recommendations for measuring rates of visual field change in glaucoma, Br J Ophthalmol, 92(4):569-73.
Advanced glaucoma interventional study.2. visual field test scoring and reliability (1994) Ophthalmology, 101(8):1445-55.
Hartong et al (2006) Retinitis pigmentosa, Lancet, 368(9549):1795-1809.
Birch et al (1999) Yearly rates of rod and cone functional loss in retinitis pigmentosa and cone-rod dystrophy, Ophthalmology, 106(2):258-68.
Holopigian et al (1996) Rates of change differ among measures of visual function in patients with retinitis pigmentosa, Ophthalmology, 103(3):398-405.
Ben-Ner et al., "Chromatic multifocal pupilometer for objective perimetry in patients with macular degemation", Israel Society for Vision & Eye Research 35th Annual Meeting, p. 22, Presentation: Mar. 11-12, 2015 (Abstract Only published).
Ben-Ner et al., "Chromatic Multifocal pupilometer for Objective Diagnosis of Neurodegeneration in the Eye and the Brain", Israel Society for Vision & Eye Research 37th Annual Meeting, p. 30, Presentation: Mar. 15-16, 2017 (Abstract Only published).
Chibel et al., "Chromatic pupilometer-based perimetry in normal eyes and patients with retinitis pigmentosa", Israel Society for Vision & Eye Research 34rd Annual Meeting, p. 100, Presentation: Mar. 26-27, 2014 (Abstract only published).
Chibel et al., "Chromatic multifocal pupilometer for objective perimetry in health subjects and patients with retinal dystrophies", Israel Society for Vision & Eye Research 35th Annual Meeting, p. 89, Presentation: Mar. 11-12, 2015 (Abstract Only published).
Chibel et al., Chromatic Multifocal Pupillometer for Objective Permetry and Diagnosis of Patients with Retinitis Pigmentosa, Ophthamology, 123, pp. 1898-1911, 2016.
Gomez et al., "Pupillary Escape Quantification with an Image-Processing System in Clinical Perimetry", Bioelectronics Section, Department of Electrical Engineering; Proceeding of SPIE, vol. 2673, pp. 252-261, 1996.
Kardon et al., "Chromatic Pupil Responses. Preferential Activation of the MelanpsinMediated Versus Outer Photoreceptor-Mediated Pupil Light Reflex", American Academy of Ophthalmology, pp. 1564-1573, 2009.
Kardon et al., "Chromatic Pupillometry in Patients with Retinitis Pigmentosa", American Academy of Opthalmology, Elsevier Inc., pp. 376-381, 2011.
Maeda et al., "A Pupil Perimeter for Objective Visual Field Measurement", Department of Sensory Science; Complex Medical Engineering, IEEE/ICME International Conference, pp. 1116-1119, May 2007.
Mhajna et al., "Chromatic pupilometer-based perimetry in patients with Best's vitelliform macular dystrophy", Israel Society for Vision & Eye Research 34rd Annual Meeting, p. 101, Presentation: Mar. 26-27, 2014 (Abstract only published).
Rotenstreich et al (2004) The application of chromatic dark-adapted kinetic perimetry to retinal diseases, Ophthalmology, 111(6) 1222-7.
Rotenstreich et al., "Novel Technique" A pupilometer-Based Objective Chromatic Perimetry, Investigative Ophthalmology & Visual Science, vol. 54, 3944, Jun. 2013 (Abstract only).
Rotenstreich et al (2014) Novel Technique: a pupillometry based objective chromatic perimetry, Ophthalmic Technology XXIV, vol. 8930.
Rotenstreich et al., "Novel technique: a pupilometer-based objective chromatic perimetry", SPIE Photonics West 2014, Presentation: Feb. 1-6, 2014, (Abstract only published).
Rotenstreich et al (2015) The first prototype of chromatic pupillometer for objective perimetry in retinal degneration patients, Ophthalmic Technologies XXIV. vol. 9307.
Rotenstreich et al., "Chromatic multifocal pupilometer for objective perimetryin patients with macular degeneration", SPIE Photonics West 2016, Presentation: Feb. 13-18, 2016, p. 110 (Abstract Only published).
Rotenstreich et al, "Pupillary responses of healthy subjects to chromatic light stimuli at incremental intensities at central and peripheral visual field locations", SPIE Photonics West 2016, Presentation: Feb. 13-18, 2016, p. 110 (Abstract Only published).
Rotenstreich et al., "Objective chromatic perimetry using a multifocal pupilometer", SPIE Photonics West 2016, Presentation Feb. 13-18, 2016, p. 117 (Abstract Only published).
Rotenstreich et al., "Chromatic multifocal pupilometer for objective perimetry in macular and retinal degeneration diseases", American Academy of Ophthalmology, AAO 2016 Presentation: Oct. 15-18, 2016 (Abstract Only published).
Rotenstreich et al., "Chromatic Multifocal Pupillometer for Objective Early Diagnosis of Mild Cognitive Impairment", Proceedings vol. 10045, Ophthalmic Technologies XXVII; 100451Z (2017) (Abstract Only).
Sher-Rosenthal et al., "Novel Technique: Chromatic Multifocal Pupillometer for Objective Evaluating 76-Point Central 30 Degree Perimetry", Investigative Ophthalmology & Visual Science, vol. 55, 4839, Apr. 2014 (Abstract Only).
Sher-Rosenthal et al., "Chromatic multifocal pupilloperimetry for objective perimetry in retinal and optic nerve neurodegeneration", AROV Annual Meeting Presentation, Jun. 2017 (Abstract Only published).
Skatt et al., "Pupillometer-Based Objective Chromatic Perimetry in Normal Subjects and Glaucoma Patients", Investigative Ophthalmology & Visual Science, vol. 52, 5094, Apr. 2011 (Abstract only).
Skatt et al., "A Preliminary Evaluation of a Pupillometer-Based Objective Chromatic Perimetry", Investigative Ophthalmology & Visual Science, vol. 51, 4793, Apr. 2010 (Abstract Only published).
Skat et al (2013) Pupillometer-Based Objective Chromatic Perimetry in Normal Eyes and Patients with Retinal Photorecptor Dystrophies, Investigative Ophthalmology & Visual Science, vol. 54(4): 2761-2771.
Tapia et al., "Pupillary responses evoked by chromatic stimulus in objective perimetry", IS&T/SPIE Conference on Human Vision and Electronic Imaging IV, Jan. 1999, 598-605, SPIE vol. 3644.
Yahia et al., "Objective chromatic pupilometer—pupillary responses of health subjects to chromatic stimulations from small 2.5-mm-diameter spots", Israel Society for Vision & Eye Research 34rd Annual Meeting, p. 122, Presentation: Mar. 26-27, 2014 (Abstract only published).
Yahia et al., "Pupillary responses of healthy subjects to chromatic light stimuli at incremental intensities at central and peripheral visual field locations", Israel Society for Vision & Eye Research 35th Annual Meeting, p. 87, Presentation: Mar. 11-12, 2015, (Abstract Only published).
European Office Action dated Feb. 26, 2015 for the corresponding EP Application No. 10754996.6.
International Search Report and Written Opinion dated Mar. 23, 2011 for corresponding PCT Application No. PCT/IL2010/000624.
Curcio et al., "Human Photoreceptor Topography", The Journal of Comparative Neurology, Wiley-Liss, Inc. vol. 292, pp. 497-523, 1990.

* cited by examiner

SYSTEM AND METHOD FOR PERFORMING OBJECTIVE PERIMETRY AND DIAGNOSIS OF PATIENTS WITH RETINITIS PIGMENTOSA AND OTHER OCULAR DISEASES

CROSS-REFERENCE TO RELATED APPLICATIONS

This application claims the benefit of U.S. Provisional Application Ser. No. 62/277,520 (ACCU 0017 MA), filed Jan. 12, 2016.

BACKGROUND

The present disclosure relates to the use of objective perimetry in the diagnosis of ocular diseases and, more specifically, to the use of a chromatic multifocal pupillometer in the objective diagnosis of retinitis pigmentosa (RP), and other ocular diseases, and in the assessment of visual field defects.

BRIEF SUMMARY

Visual field (VF) testing is part of the current clinical standard for evaluating retinal degeneration and optic nerve damage. Dark-adapted Goldmann perimetry and automated perimetry are used most commonly for detecting and monitoring patients with retinitis pigmentosa (RP). These methods bear significant limitations because they are subjective by nature and rely heavily on subject cooperation and attention. Hence, testing of young children, the elderly, and individuals with impaired communication skills is doomed to yield unreliable results. These tests also may be stressful for patients because they need to make conscious decisions on identification of near-threshold stimuli that appear rapidly and disappear. Moreover, test results may be affected by the patient's fatigue, wakefulness, and attentiveness during the long procedure. Therefore, constant monitoring and instruction of participants by qualified personnel are needed to obtain reliable results. Furthermore, test-retest variability, in particular in peripheral locations and in regions of VF deficits, makes it difficult to determine whether the VF is worsening over the course of serial examinations. Hence, frequent examinations are needed and misdiagnosis of early stages is common.

Retinitis pigmentosa encompasses a group of progressive retinal degeneration diseases that predominantly affect the rod photoreceptor system, resulting in night blindness in the early phase of the disease and loss of peripheral vision that progresses to tunnel vision. In later stages of RP, degeneration of cone photoreceptors causes progressive decline of visual acuity. Disease progression is monitored by electroretinography and perimetry. However, poor test-retest repeatability in patients with RP, specifically in areas with VF deficits, limits the ability to assess disease progression and particularly to design and interpret clinical trials of potential therapeutic agents.

A chromatic multifocal pupillometer can be used for detection of VF defects in RP patients. Retinitis pigmentosa patients have demonstrated a significantly reduced percentage of pupil contraction (PPC) compared with healthy participants in testing conditions that emphasize rod contribution (blue light). By contrast, the PPC in response to red light (which emphasizes cone contribution) is reduced significantly in RP patients compared with healthy participants, mostly in peripheral locations. In central locations, there is no significant difference between the PPC of RP patients and healthy participants in response to red light. RP patients have also demonstrated significantly lower PPC in response to blue light in peripheral locations of the central VF than healthy participants. Furthermore, minimal PPC has been recorded in RP patients in areas that were not detected in dark-adapted chromatic Goldmann perimetry. It is contemplated that VF defects, as well as rod and cone function, may be assessed in RP patients using a chromatic multi-focal pupillometer.

Considering the dynamics of the pupil response in the central VF of RP patients and healthy participants, it is contemplated that additional parameters of the pupil light response, i.e., the maximal contraction velocity (MCV), the latency of MCV (LMCV), pupil response latency (PRL), percentage of pupil maximal relaxation (PRP), maximal relaxation velocity (MRV), latency of MRV (LMRV), maximal contraction acceleration (MCA), latency MCA (LMCA), maximal contraction deceleration (MCD), latency of MCD (LMCD), maximal relaxation acceleration (MRA), latency of MRA (LMRA), maximal relaxation deceleration (MRD), and latency of MRA (LMRD) may be used to evaluate retinal degeneration. RP patients have demonstrated significantly lower PPC and MCV in areas that were reported as non-seeing by CDA-GVF. Considering that the mean absolute deviation in the LMCV parameter between different test point locations is often significantly higher in RP patients, it is contemplated that LMCV may be a valuable diagnostic tool for RP.

In accordance with one embodiment of the present disclosure, a method for determining a state of health of an eye using a pupillometer is provided comprising an ocular fixture, a testing compartment, at least one camera, and a controller. The testing compartment comprises a plurality of chromatic beam emitters arranged about a visual field of the pupillometer. Selected ones of the chromatic beam emitters are structurally configured to generate chromatic stimuli within a blue portion of a visible electromagnetic spectrum. Selected ones of the chromatic beam emitters are structurally configured to generate chromatic stimuli within a red portion of the visible electromagnetic spectrum. The ocular fixture is positioned to facilitate exposure of light sensitive ocular structures of the eye to a blue and red chromatic stimuli of the chromatic beam emitters. The camera is positioned to record temporal pupil contraction of the eye in response to the blue and red chromatic stimuli of the chromatic beam emitters. The controller controls emission wavelength, intensity, and duration of the chromatic beam emitters. The controller processes temporal pupil contraction data recorded by the camera to generate a plurality of latent maximum contraction velocity (LMCV) signals representative of the eye positioned at the ocular fixture in response to the blue and red chromatic stimuli at a plurality of locations in the visual field of the pupillometer. The method comprises positioning a subject eye at the ocular fixture, driving the chromatic beam emitters with the controller to generate the LMCV signals using chromatic stimuli within the blue and red portions of the visible electromagnetic spectrum, where the controller drives the chromatic beam emitters such that red chromatic stimuli intensity is at least 2 times greater than the blue chromatic stimuli intensity, and determining the state of health of the subject eye as an objective function of the LMCV signals.

In accordance with another embodiment of the present disclosure, a method for determining the state of health of an eye using a pupillometer is provided comprising an ocular fixture, a testing compartment, at least one camera, and a controller. The testing compartment comprises a plurality of chromatic beam emitters arranged about a visual field of the pupillometer. Selected ones of the chromatic beam emitters are structurally configured to generate chromatic stimuli. The ocular fixture is positioned to facilitate exposure of light sensitive ocular structures of the eye to the chromatic stimuli of the chromatic beam emitters. The camera is positioned to record temporal pupil contraction of the eye in response to the chromatic stimuli of the chromatic beam emitters. The controller controls emission wavelength, intensity, and duration of the chromatic beam emitters. The controller processes temporal pupil contraction data recorded by the camera to generate latent maximum contraction velocity (LMCV) signals and percentage of pupil contraction (PPC) or maximal contraction velocity (MCV) signals representative of the eye positioned at the ocular fixture in response to the chromatic stimuli of the chromatic beam emitters at a plurality of locations in the visual field of the pupillometer. The method comprises positioning a subject eye at the ocular fixture, driving the chromatic beam emitters with the controller in a first illumination mode to determine an extent of a functional visual field of the subject eye from the PPC or MCV signals, and driving the chromatic beam emitters with the controller in a second illumination mode to determine the state of health of the subject eye as an objective function of the LMCV signals, where the controller selects and drives the chromatic beam emitters based on the extent of the functional visual field determined in the first illumination mode.

In accordance with another embodiment of the present disclosure, a pupillometer is provided comprising an ocular fixture, a testing compartment, at least one camera, and a controller. The testing compartment comprises a plurality of chromatic beam emitters arranged about a visual field of the pupillometer. Selected ones of the chromatic beam emitters are structurally configured to generate chromatic stimuli within a blue portion of a visible electromagnetic spectrum. Selected ones of the chromatic beam emitters are structurally configured to generate chromatic stimuli within a red portion of the visible electromagnetic spectrum. The ocular fixture is positioned to facilitate exposure of light sensitive ocular structures of an eye to a blue and red chromatic stimuli of the chromatic beam emitters. The camera is positioned to record temporal pupil contraction of the eye in response to the blue and red chromatic stimuli of the chromatic beam emitters. The controller controls emission wavelength, intensity, and duration of the chromatic beam emitters. The controller processes temporal pupil contraction data recorded by the camera to generate a latent maximum contraction velocity (LMCV) signal representative of the eye in response to the blue and red chromatic stimuli of the chromatic beam emitters. The controller is programmed to drive the chromatic beam emitters to generate chromatic stimuli within the blue and red portions of the visible electromagnetic spectrum such that red chromatic stimuli intensity is at least 2 times greater than blue chromatic stimuli intensity for generation of the latent maximum contraction velocity (LMCV) signal.

In accordance with yet another embodiment of the present disclosure, a pupillometer is provided comprising an ocular fixture, a testing compartment, at least one camera, and a controller. The testing compartment comprises a plurality of chromatic beam emitters arranged about a visual field of the pupillometer. Selected ones of the chromatic beam emitters are structurally configured to generate chromatic stimuli. The ocular fixture is positioned to facilitate exposure of light sensitive ocular structures of an eye to the chromatic stimuli of the chromatic beam emitters. The camera is positioned to record temporal pupil contraction of the eye in response to the chromatic stimuli of the chromatic beam emitters. The controller controls emission wavelength, intensity, and duration of the chromatic beam emitters. The controller processes temporal pupil contraction data recorded by the camera to generate latent maximum contraction velocity (LMCV) signals and percentage of pupil contraction (PPC) or maximal contraction velocity (MCV) signals representative of the eye positioned at the ocular fixture in response to the chromatic stimuli of the chromatic beam emitters at a plurality of locations in the visual field of the pupillometer. The controller is programmed to drive the chromatic beam emitters in a first illumination mode to determine an extent of a functional visual field of a subject eye from the PPC or MCV signals and drive the chromatic beam emitters in a second illumination mode to determine the state of health of the subject eye as an objective function of the LMCV signals, where the controller selects and drives the chromatic beam emitters based on the extent of the functional visual field determined in the first illumination mode.

Although the concepts of the present disclosure are described herein with primary reference to the diagnosis of Retinitis Pigmentosa, and other forms of retinal degeneration and optic nerve damage, it is contemplated that the concepts will enjoy applicability to the diagnosis of a variety of ocular and non-ocular diseases, syndromes or disorders including, for example, Best Vitelliform Macular Dystrophy, macular degeneration, Glaucoma, mild cognitive impairment, Alzheimer and others which can affect the retinal cells and visual pathways in the eye and brain.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIGS. 6G-6I illustrate the mean LCMV parameters in response to blue light in healthy subjects (FIG. 6G), in patients from group A (FIG. 6H), and in patients from group B (FIG. 6I), for each of the 76 test targets of the 16.2 degree visual field (VF) according to one or more embodiments shown and described herein;

FIGS. 7G-7I illustrate the mean LCMV parameters in response to blue light in healthy subjects (FIG. 7G), in patients from group A (FIG. 7H), and in patients from group B (FIG. 7I), for each of the 76 test targets of the 16.2 degree visual field (VF) according to one or more embodiments shown and described herein;

DETAILED DESCRIPTION

The principles and operation of the system and method for performing objective perimetry and diagnosis of patients with retinitis pigmentosa (RP) and other ocular diseases may be better understood with reference to the drawings and the accompanying description.

Embodiments of the present disclosure, as will be explained in further detail below, are generally directed to a system and method that presents chromatic stimuli to a subject eye, records the temporal pupil response to the chromatic stimuli via a camera and analyzes the recorded temporal pupil response data. The recorded temporal pupil response data may be processed by the system and pupil response parameters may be determined to define a visual field of a subject eye and for determining a state of health of the subject eye. The system and method for performing objective perimetry and diagnosis of patients with retinitis pigmentosa and other ocular diseases will now be described in more detail.

Figure 1:
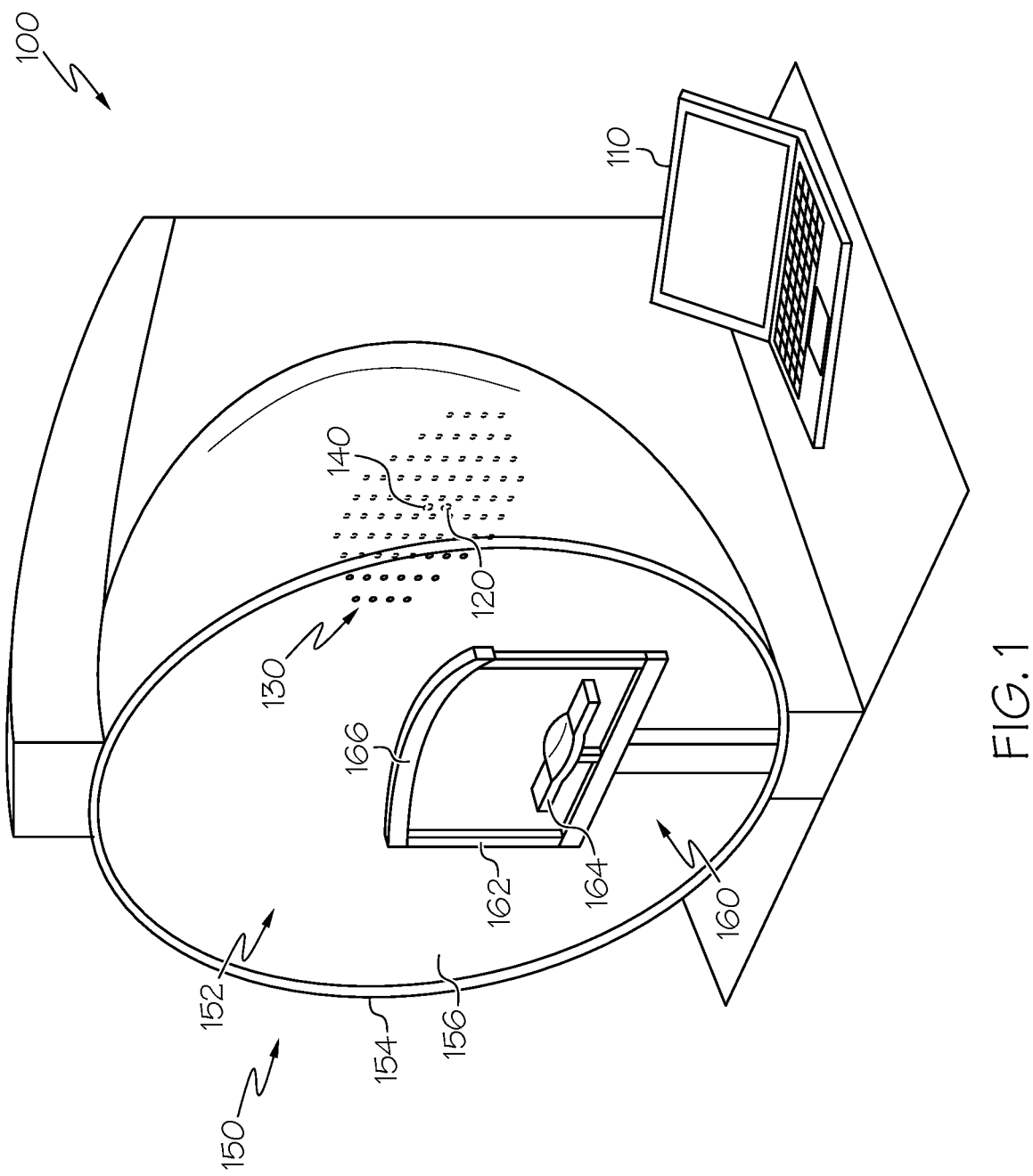
FIG. 1 illustrates an example of an open chromatic multifocal pupillometer system according to one or more embodiments shown and described herein.
Figure 2:
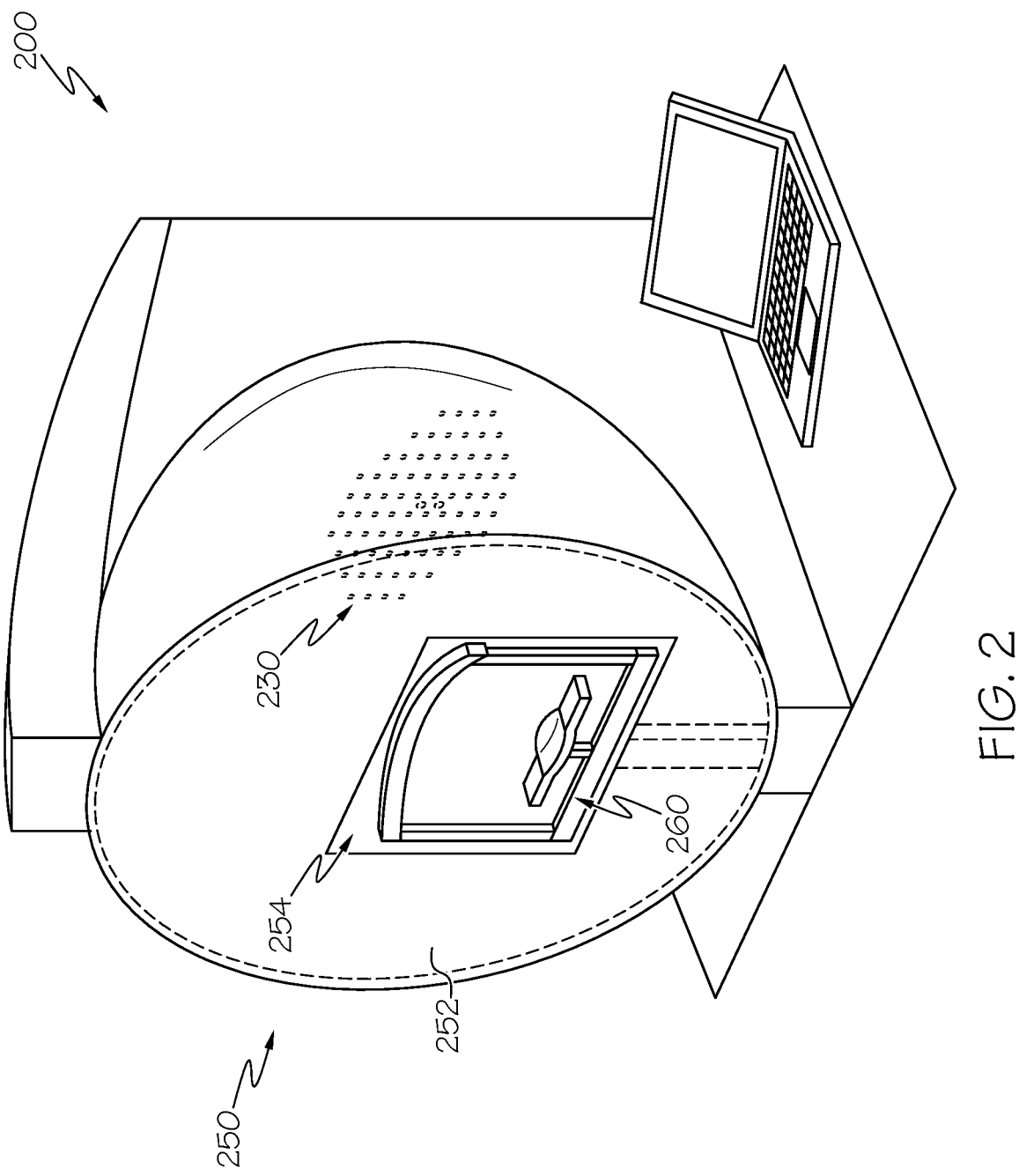
FIG. 2 illustrates an example of a closed chromatic multifocal pupillometer system according to one or more embodiments shown and described herein.

Referring now to the drawings, FIGS. 1 and 2 illustrate examples of a chromatic multifocal pupilometer system for performing objective perimetry and diagnosis of patients with retinitis pigmentosa and other ocular diseases. As illustrated in FIG. 1, the chromatic multifocal pupilometer system 100 comprises a controller 110, a camera 120, a plurality of chromatic beam emitters 130, a fixation point 140, a testing compartment 150 and an ocular fixture 160, comprising a frame structure 162, a chin rest 164 and a forehead band 166. As a non-limiting example and as shown in FIG. 1, the testing compartment 150 is an open testing compartment provided in the form of a substantially hemispheric bowl having an opening 152 defined by a perimeter 154 and an inner surface 156. In other embodiments, for example, without limitation, and as shown in FIG. 2, the testing compartment 250 is a closed testing compartment 250 provided in the form of a substantially hemispheric bowl comprising an enclosing surface 252 with a viewing port 254 positioned between the ocular fixture 260 and the plurality of chromatic beam emitters 230. In other embodiments, the testing compartment is a portable unit. In further embodiments, the testing compartment encompasses a room such that the chromatic stimuli are presented in the dark room comprising a background luminance of less than about 30 cd/m², preferably 0.05 cd/m².

Referring again to FIG. 1, the ocular fixture 160 is coupled to the chromatic multifocal pupilometer system 100. The ocular fixture 160 is positioned to facilitate exposure of light sensitive ocular structures of an eye to the chromatic stimuli of the chromatic beam emitters 130. The chin rest 164 and forehead band 166 interconnected by the frame structure 162 within the opening 152 of the testing compartment 150 may aid in positioning of the eye toward the chromatic beam emitters 130. In some embodiments, the ocular fixture 160 may comprise additional or fewer components for positioning the subject eye.

The plurality of chromatic beam emitters 130 may be arranged about the inner surface 156 of the testing compartment 150. The plurality of chromatic beam emitters 130, for example without limitation, may be positioned in a grid pattern at a plurality of locations arranged about the inner surface 156 of the testing compartment. In some embodiments, the chromatic beam emitters 130 are positioned and driven to generate chromatic stimuli throughout a substantial entirety of the visual field. The visual field may be defined by a viewing cone of about +/−120 degrees extending from the ocular fixture 160 into the testing compartment. In some embodiments, the visual field is defined by a viewing cone of about +/−15 degrees or about +/−16.2 degrees extending from the ocular fixture 160 to the chromatic beam emitters 130. In other embodiments, the visual field is defined by a viewing cone of about +/−30 degrees extending from the ocular fixture 160 to the chromatic beam emitters 130. The viewing cone encompasses between about 1 and about 1000 chromatic beam emitters or between about 7 and about 76 chromatic beam emitters.

Additionally, the inner surface 156 may be associated with the camera 120 and the fixation point 140. In FIG. 1, the camera 120 is positioned below the fixation point 140 and the fixation point 140 is positioned at the center of the field defined by the plurality of chromatic beam emitters 130. However, in other embodiments the camera 120 may be positioned independent of the location of the fixation point 140 or the field defined by the plurality of chromatic beam emitters 130 so long as the camera is capable of recording the temporal pupil contraction of the subject eye when the subject eye is positioned by the ocular fixture 160 to receive chromatic stimuli from the plurality chromatic beam emitters 130. Similarly, in other embodiments, the fixation point 140 may be positioned independent of the center of the field defined by the plurality of chromatic beam emitters 130 within the testing compartment 150. In such embodiments, the fixation point 140 may be positioned at the center of the substantially hemispheric bowl on the inner surface 156 of the testing compartment 150. The fixation point 140, for example, without limitation, is an area, a spot or object which contrasts with the inner surface 156 of the testing compartment 150 so that the subject eye may maintain a gaze upon it during administration of the chromatic stimuli.

The camera 120 may be any device having an array of sensing devices (e.g., pixels) capable of detecting radiation in an ultraviolet wavelength band, a visible light wavelength band, or an infrared wavelength band. The camera 120 may be an infrared camera. The camera 120 may have any resolution. The camera 120 may be an omni-directional camera, or a panoramic camera. In some embodiments, one or more optical components, such as a mirror, fish-eye lens, or any other type of lens may be optically coupled to the camera 120. Additionally, one or more cameras may be positioned to record the temporal pupil contraction of the eye.

Still referring to FIG. 1, the controller 110 is communicatively coupled to the camera 120 and the plurality of chromatic beam emitters 130. The controller 110 may be any device or combination of components comprising a processor and non-transitory computer readable memory. The processor may be any device capable of executing the machine-readable instruction set stored in the non-transitory computer readable memory. Accordingly, the processor may be an electric controller, an integrated circuit, a microchip, a computer, or any other computing device. The processor is communicatively coupled to various components of the chromatic multifocal pupilometer system 100 by a communication path. Accordingly, the communication path may communicatively couple any number of processors with one another, and allow the components coupled to the communication path to operate in a distributed computing environment. Specifically, each of the components may operate as a node that may send and/or receive data. While the embodiment depicted in FIG. 1 includes a single controller 110 shown as a computer, other embodiments may include one or more discrete or integrated controllers each comprising one or more processor.

The non-transitory computer readable memory may comprise RAM, ROM, flash memories, hard drives, or any non-transitory memory device capable of storing machine-readable instructions such that the machine-readable instructions can be accessed and executed by the processor. The machine-readable instruction set may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine readable instructions and stored in the non-transitory computer readable memory. Alternatively, the machine-readable instruction set may be written in a hardware description language (HDL), such as logic implemented via either a field-programmable gate array (FPGA) configuration or an application-specific integrated circuit (ASIC), or their equivalents. Accordingly, the functionality described herein may be implemented in any conventional computer programming language, as pre-programmed hardware elements, or as a combination of hardware and software components. While the embodiment depicted in FIG. 1 includes a single controller with non-transitory computer readable memory, other embodiments may include more than one memory module.

In embodiments, the controller 110 activates selected ones of the chromatic beam emitters 130 providing chromatic stimuli defining various test locations within the visual field. The controller 110 may selectively activate chromatic beam emitters 130 individually or in combination. The duration in which the chromatic stimuli of the chromatic beam emitters are generated by the controller may be between about 0.1 seconds and about 60 seconds. In other embodiments, the controller activates selected ones of the chromatic beam emitters for a duration between about 1 second and about 10 seconds, preferably between about 1 second and about 8 seconds. Additionally, the controller 110 may simultaneously activate the camera 120 to record temporal pupil contraction of the eye in response to the chromatic stimuli of the chromatic beam emitters 130 for a duration between about 2 seconds and about 10,000 seconds, preferably about 12 seconds.

The controller processes the temporal pupil contraction data recorded by the camera to generate, for example, without limitation, latent maximum contraction velocity (LMCV) signals, percentage of pupil contraction (PPC) signals and maximum contraction velocity (MCV) signals representative of the eye positioned at the ocular fixture 160 in response to the chromatic stimuli of the chromatic beam emitters 130. Percentage of pupil contraction is a function of the initial diameter of the pupil (in pixels) and the minimum pupil diameter (in pixels). The initial diameter of the pupil is the diameter of the pupil before the chromatic stimulus is activated and after the subject eye has been dark adapted for a period of time. Percentage of pupil contraction (PPC) is determined using the following formula:

$$PPC = \frac{\text{Initial Pupil Diameter} - \text{Minimum Pupil Diamater}}{\text{Initial Pupil Diameter}} * 100$$

Figure 3:
FIG. 3 illustrates an example pupil response to chromatic stimuli indicating measured parameters maximum constriction velocity (MCV) and latency of maximum constriction velocity (LMCV) according to one or more embodiments shown and described herein.

The maximum contraction velocity (MCV) is determined by calculating the maximum rate at which the pupil contracts from the chromatic stimulus between the initial pupil diameter measurement and the minimum pupil diameter measurement. The latency of maximum contraction velocity (LMCV) is determined by calculating the time point for each pupil response at which the maximum rate of pupil contraction (MCV) occurs for each chromatic stimulus generated by the chromatic beam emitters 130 at the various test locations. Referring to FIG. 3, an example pupil response to chromatic stimuli indicating measured parameters maximum constriction velocity (MCV) and latency of maximum constriction velocity (LMCV) is depicted. As discussed below with respect to the experimental study, the example chart in FIG. 3 depicts the recorded pupil diameter constriction and de-constriction over a period of 4 seconds where the chromatic stimulus was presented during the first second. As shown, latency of maximum constriction velocity (LMCV) is the time interval from the initialization of the chromatic stimulus to the time point at which maximum constriction velocity (MCV) is achieved.

Additionally, the controller 110 controls emission wavelength, intensity and duration of the plurality of chromatic beam emitters 130, which are communicatively coupled to the controller 110 to generate the chromatic stimuli. The chromatic beam emitters 130 are structurally configured to generate chromatic stimuli within a blue portion of the visible electromagnetic spectrum or within a red portion of the visible electromagnetic spectrum. The chromatic beam emitters 130 that generate chromatic stimuli within the blue portion of the visible electromagnetic spectrum may be independent from the chromatic beam emitters 130 that generate chromatic stimuli within the red portion of the electromagnetic spectrum. Conversely, the chromatic beam emitters 130 that generate chromatic stimuli within the blue portion of the visible electromagnetic spectrum may be the same chromatic beam emitters 130 that generate chromatic stimuli within the red portion of the electromagnetic spectrum. The chromatic beam emitters 130 are driven by the controller 110 providing an emitter drive signal indicative of a wavelength within the blue or red portion of the visible electromagnetic spectrum. In doing so, the controller 110 may also control emission wavelength by changing the emitter drive signals between blue and red portions of the visible electromagnetic spectrum.

The blue chromatic stimuli emission wavelength has a peak value lying in a range from about 410 nm to about 520 nm or from about 480 nm to about 490 nm. The red chromatic stimuli emission wavelength has a peak value lying in a range from about 550 nm to about 700 nm or from about 620 nm to about 630 nm. The peak value generally varies by about +/−5 nm. In some embodiments, the red chromatic stimuli have a luminance between about 3 cd/m$^2$ and about 7000 cd/m$^2$. In other embodiments, the red chromatic stimuli have a luminance between about 500 cd/m$^2$ and about 2000 cd/m$^2$, preferably about 1000 cd/m$^2$. The intensity of the red chromatic stimuli is between about 2 and about 5 times greater than the blue chromatic stimuli intensity. However, in other embodiments, the red and blue chromatic stimuli approximate the minimum intensity yielding a pupil response to the stimuli in healthy participants.

In embodiments, the chromatic beam emitters 130 are light emitting diodes. In other embodiments the chromatic beam emitters 130 may be a liquid crystal display, plasma display or the like where portions of the display are defined by the controller 110 to generate chromatic stimuli. Regardless of the element implemented as the chromatic beam emitters 130, the chromatic beam emitters 130 are optically configured to generate a spot size of about 1.8 mm in the visual field. Similarly, in some embodiments, the chromatic beam emitters are optically configured to generate a spot size of between about 0.5 mm and about 8 mm in the visual field.

In operation, the above-described system is capable of preforming at least the following methods described in detail herein. In one embodiment, once a subject eye is positioned in the ocular fixture and dark-adapted, the controller 110 drives selected ones of the chromatic beam emitters 130 within the blue and red portions of the visible electromagnetic spectrum to generate LMVC signals in response to the blue and red chromatic stimuli generated by the chromatic beam emitters 130. The controller drives the chromatic beam emitters such that the red chromatic stimuli intensity is at least 2 times greater than blue chromatic stimuli intensity. Subsequently, the state of health of the subject eye is determined as an objective function of the LMCV signals.

In another embodiment, once the subject eye is positioned in the ocular fixture and dark-adapted, the controller 110 drives selected ones of the chromatic beam emitters 130 in a first illumination mode and records the temporal pupil response of the subject eye with the camera 120. The temporal pupil response data is used to generate PPC or MCV signals representative of the subject eye positioned at the ocular fixture in response to the chromatic stimuli of the chromatic beam emitters in the first illumination mode. The controller determines a functional visual field using the generated PPC or MCV signals. A normal function visual field is an island of vision measuring 90 degrees temporally to central Fixation, 50 degrees superiorly and nasally, and 60 degrees inferiorly. The controller 110 uses the functional visual field to select and drive chromatic beam emitters 130 in a second illumination mode. The controller generates LMCV signals representative of the subject eye in response to the second illumination and thus determines the state of health of the subject eye as an objective function of the LMCV signals. In some embodiments, the controller selects and drives chromatic beam emitters to define an illuminated portion of the visual field of the pupilometer and the illuminated portion of the visual field of the pupillometer does not exceed substantially beyond the functional visual field of the subject eye. In other embodiments, the controller selects and drives chromatic beam emitters to define an illuminated portion of the visual field of the pupilometer and the illuminated portion of the visual field of the pupillometer is substantially congruent with the functional visual field of the subject eye.

The first illuminance mode and the second illuminance mode may be multi-chromatic stimuli comprising red and blue chromatic stimuli. In some embodiments, the red chromatic stimuli may have a luminance between about 3 cd/m$^2$ and about 7000 cd/m$^2$. In other embodiments, the red chromatic stimuli may have a luminance between about 500 cd/m$^2$ and about 2000 cd/m$^2$. The intensity of the red chromatic stimuli may be between about 1 and about 1000 times the intensity of the blue chromatic stimuli. The red chromatic stimuli may have a luminance of about 1000 cd/m$^2$ and the intensity of the red chromatic stimuli may be between about 2 and about 5 times greater than the blue chromatic stimuli intensity.

In embodiments, should the participant blink during activation of the chromatic stimulus or for a period thereafter, the chromatic stimulus at that test location is retested. As a non-limiting example, should the participant blink during the first 2.5 seconds after the chromatic stimulus onset the results are automatically excluded and the test location is retested. Alternate periods may be implemented to acquire unimpeded temporal pupil contraction data. Additionally, the period for dark-adapting the subject eye prior to testing is between about 0 minutes and about 120 minutes or between about 2 minutes and about 10 minutes.

Experimental Study and Results

The system and method described herein may be better understood from the following experimental study and analysis of results. The study demonstrated the feasibility of using a chromatic multifocal pupillometer for objective diagnosis of retinitis pigmentosa (RP). The study was conducted on the right eye of 29 participants (16 healthy subjects and 13 retinitis pigmentosa (RP) patients). The objective of the study was to assess visual field (VF) defects and retinal cell function in healthy subjects and patients with retinal dystrophy using a chromatic multifocal pupillometer as described and implemented herein. The captured pupil responses were analyzed by mapping different pupil light response parameters across different locations of the VF in response to red and blue light. Correlations identified among the pupil response parameters, red and blue chromatic stimuli at different test points and known eye health of the participants indicated a chromatic multifocal pupillometer according to the system and method described herein may be used for objective diagnosis of RP and assessment of VF defects.

The chromatic multifocal pupillometer-based objective perimeter included 76 LEDs, i.e., target locations, having a target size of 1.8 mm in diameter. The VF of RP patients was assessed using the pupillometer and was compared with the patients' dark adapted Goldmann visual field (DA-GVF) results as well as the pupillometry results of healthy subjects.

Sixteen normal healthy volunteers, age-matched with patients, (see below; six males, ten females; mean±SD age: 38.4±15.6 years; range: 26-77 years) were included in the study. Inclusion criteria were normal eye examination, best-corrected visual acuity (BCVA) of 20/20, normal color vision, no history of past or present ocular disease, no use of any topical or systemic medications that could adversely influence efferent pupil movements, and normal 24-2 Swedish Interactive Threshold Algorithm (SITA), developed for the Humphrey standard perimeter (Humphrey Field Analyser II, SITA 24-2; Carl Zeiss Meditec, Inc., Jena, Germany).

The study patient group comprised 13 patients with retinitis pigmentosa (RP) (3 females and 10 males; mean±SD age: 36.15±14.6 years; range: 20-65 years). Inclusion criteria for RP patients were typical abnormal fundus appearance and a previously recorded ERG that was abnormal under scotopic or photopic conditions or both (in compliance with the protocol of the International Society for Clinical Electrophysiology of Vision (ISCEV) and typical abnormal Kinetic Chromatic Goldmann test results).

Exclusion criteria were a concurrent ocular disease and any other condition affecting the pupil response to light. Data recorded for all patients included gender, diagnosis and ERG responses. Patients were tested for best-corrected visual acuity and for color vision by Farnsworth D15 test. The right eyes of both healthy and RP participants were examined.

Light Stimuli: Light stimuli were presented using a Ganzfeld dome apparatus, an example of which is illustrated in FIGS. 1 and 2, placed 330 mm from the patient's eye. All tests were performed in a dark room. The untested eye was covered. Participants were asked to fixate on a white fixator (0.9 cd/m$^2$, as shown in FIG. 1, 140) at the center of the dome. Stimuli were presented from 76 targets (LEDs), i.e., chromatic beam emitters 130, with diameter of 1.8 mm$^2$ in a VF of 16.2 degrees. The wavelength and intensity of the chromatic stimuli selected for this study was 624±5 nm, 1000 cd/m$^2$ for the long wavelength (red light) and 485±5 nm, 200 cd/m$^2$ for short wavelength stimuli (blue light). The light intensities were chosen after preliminary calibrations that enabled us to identify the minimal stimulus intensity that yielded a substantial pupil response (PR) in five normal participants. The background luminance was 0.05 cd/m$^2$. The stimulus duration was 1 second and the inter-stimulus interval was 4 seconds.

Pupil diameter was recorded in real time by a computerized infrared high-resolution camera, e.g., camera 120 is shown in FIG. 1, that recorded the pupil diameter at a frequency of 30 Hz. The software (Accutome Inc.) searched for and measured the pupil in every image. The pupil diameter was measured in pixels with an accuracy of 0.1 mm. Prior to testing, the subjects were dark adapted for five minutes. Tests in which the subject blinked during the first 2.5 sec following stimulus onset were automatically excluded, and the targets were retested.

Analysis of Pupil Responses: During the recording of the pupil diameter in response to each chromatic stimulus, five parameters were calculated within the software, e.g., the computer-readable instruction set that was stored in the non-transitory memory of the controller, using the change in pupil diameter over time. The five parameters included, but were not limited to, the initial diameter of the pupil (in pixels), the minimum pupil diameter (in pixels), the percentage of pupil contraction (PPC), Maximal Contraction Velocity (MCV, in pixel/sec), and the Latency of the Maximal Contraction Velocity (LMCV, in sec). The PPC was determined using the following formula, as we previously described:

$$PPC = \frac{\text{Initial Pupil Diameter} - \text{Minimum Pupil \textit{Diamater}}}{\text{Initial Pupil Diameter}} * 100$$

The MCV was determined by calculating the maximum rate at which the pupil contracts from the light stimulus between the initial pupil diameter measurement and the minimum pupil diameter measurement. The LMCV was determined by calculating the time point for each pupil response at which the maximum rate of pupil contraction (MCV) occurs from each light stimulus.

RP patients were tested for kinetic VF by dark-adapted chromatic Goldmann perimetry (DA-GVF). A Goldmann perimeter (940-ST; Haag-Streit AG, Liebefeld, Switzerland) was used to map patients' conventional and two-color dark-adapted VFs. Patients were dark adapted for 30 minutes prior to testing. The setting used for stimuli were II3c for the long-wavelength stimulus and 2 log units lower in luminance (II$\overline{3}$C) for the short-wavelength stimulus. For quantification of functional DA-GVF, a schematic representation of the pupillometer target points was overlaid on the DA-GVF, and pupilometer targets that were within "seeing" areas by the DA-GVF were scored as 1. Pupilometer targets that were in "non-seeing" areas by the DA-GVF were scored as 0. Fraction of functioning VF was calculated as the sum of scores divided by 76.

Statistical analysis: Statistical analyses were performed using Excel and R 3.0.1. Results were presented as mean±standard error. Student's T-test was used to evaluate demographic differences between patients and controls. Test-retest reliability of the pupil response measurements were calculated using Pearson correlation and the correlation between pupillometer recordings and dark-adapted Goldman were calculated with Spearman's rho test. Variability in LMCV recordings was measured by the mean absolute deviation, and this measure was compared between the study group and the control group using a two-sided Wilcoxon-Mann-Whitney test. The effects of using fewer test-points and the robustness of the LMCV for discrimination was examined via simulation by randomly selecting n test-points (n=5, 10, 15, . . . 75) and calculating the Area Under the Curve (AUC) obtained using the LMCV based on these n points; this was done for 200 repeats and the mean AUC for each n thus obtained.

Figure 4A:
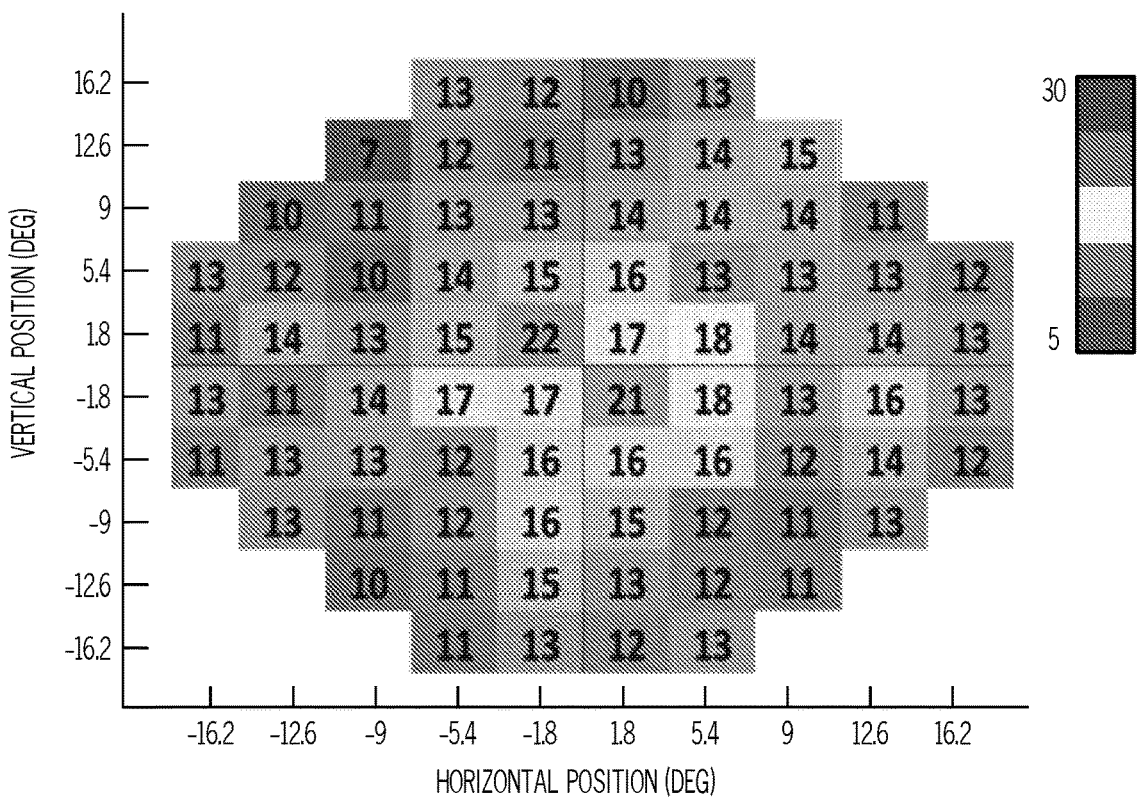
FIGS. 4A-4F illustrate the mean percentage of pupil contraction (PPC) (FIGS. 4A and 4B), maximum contraction velocity (MCV) of the pupil (FIGS. 4C and 4D), and latency in the maximum contraction velocity (LMCV) (FIGS. 4E and 4F) in response to chromatic stimuli within a blue (FIGS. 4A, 4C, and 4E) and red (FIGS. 4B, 4D, and 4F) portion of the electromagnetic spectrum according to one or more embodiments shown and described herein.
Figure 4B:
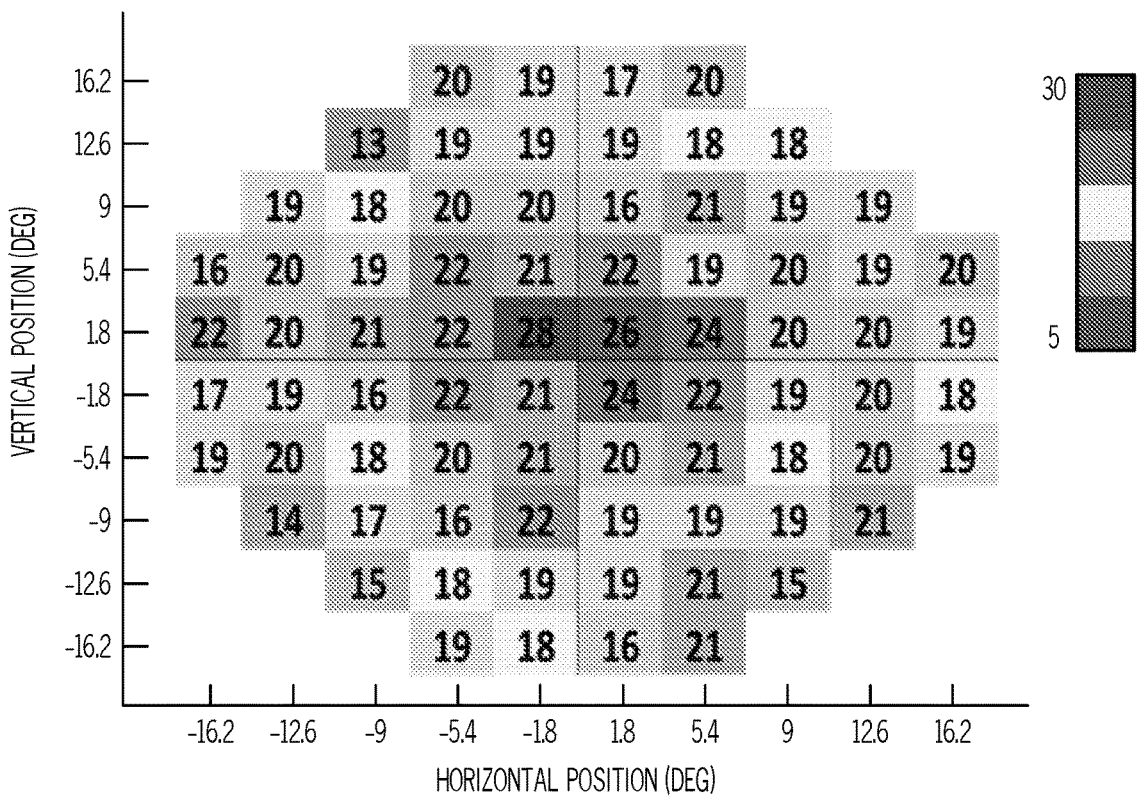
Figure 4C:
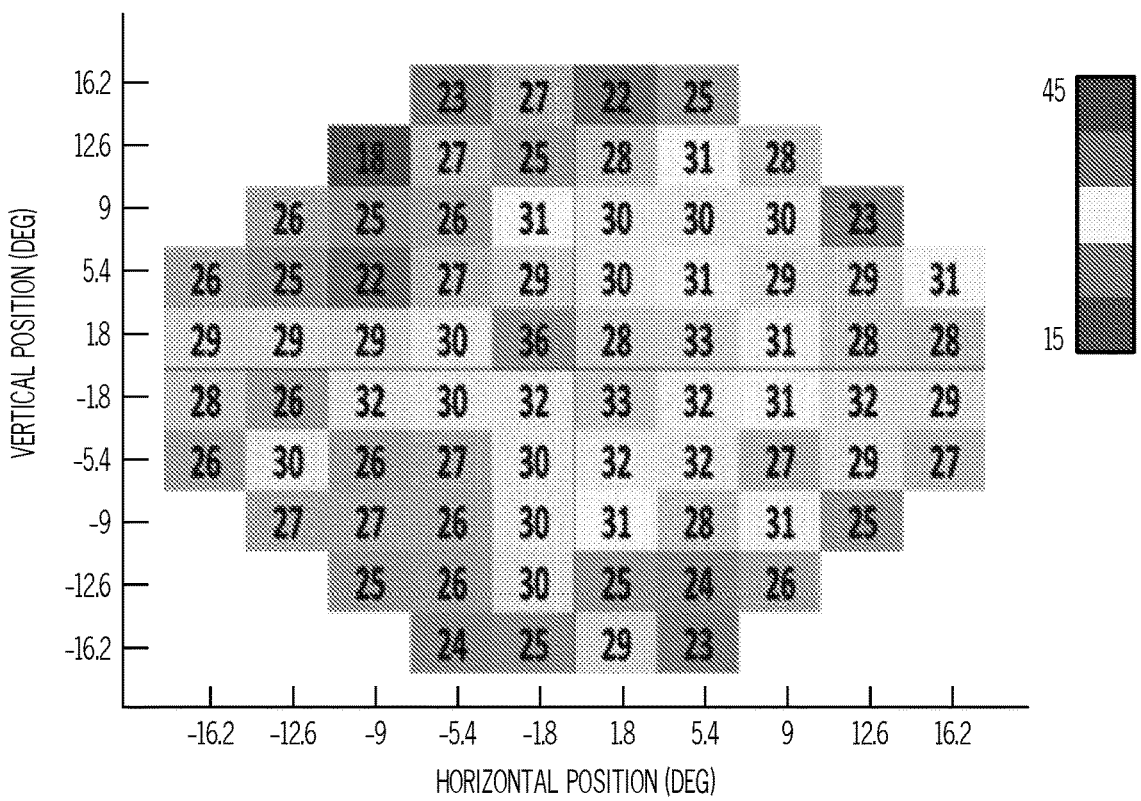
Figure 4D:
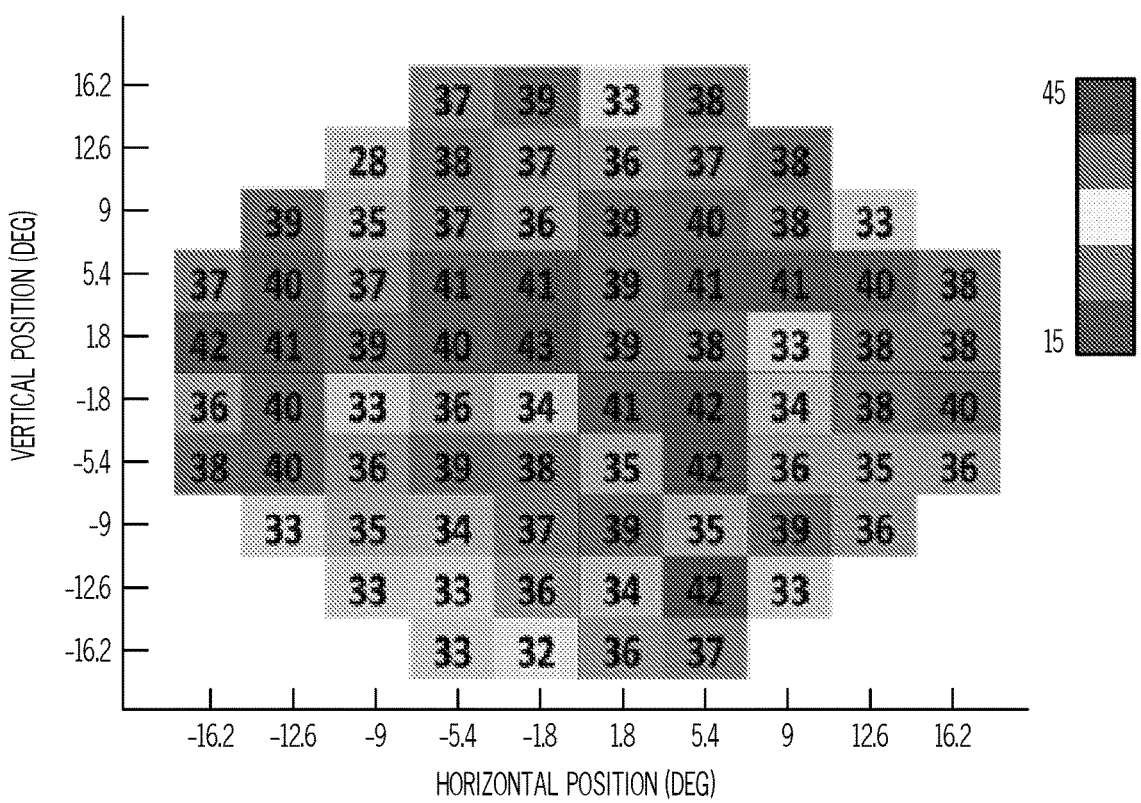
Figure 4E:
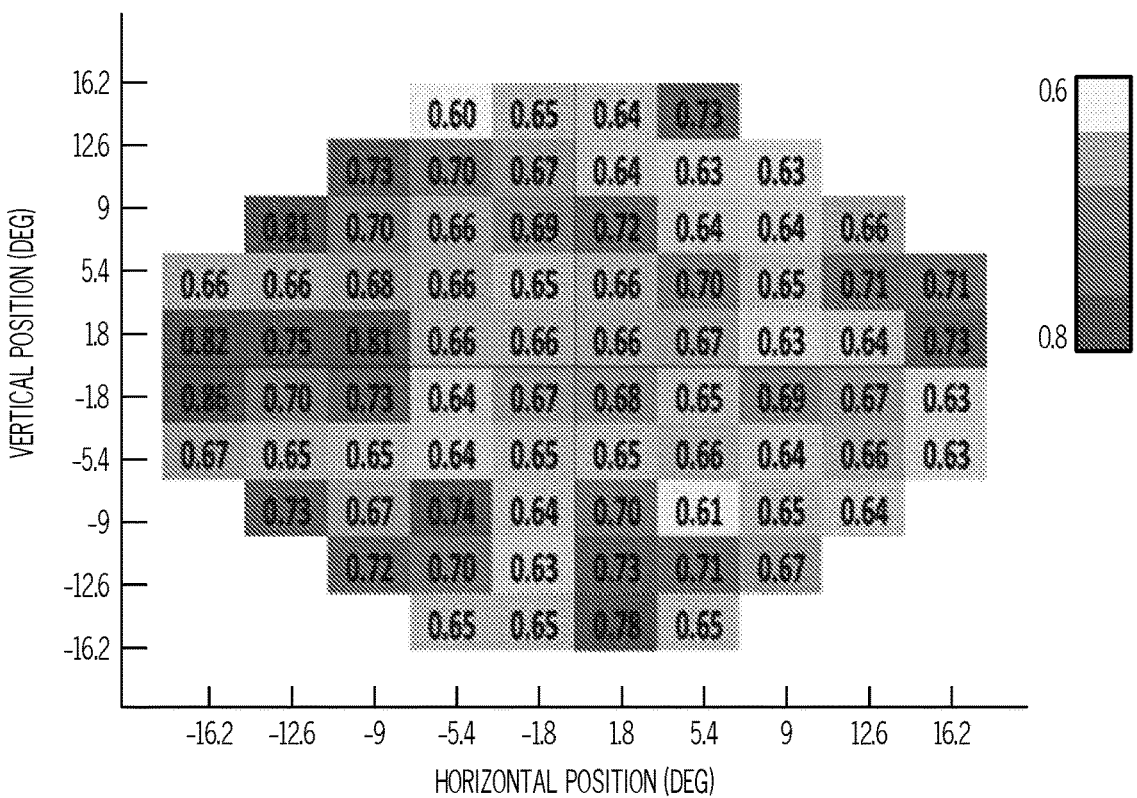
Figure 4F:
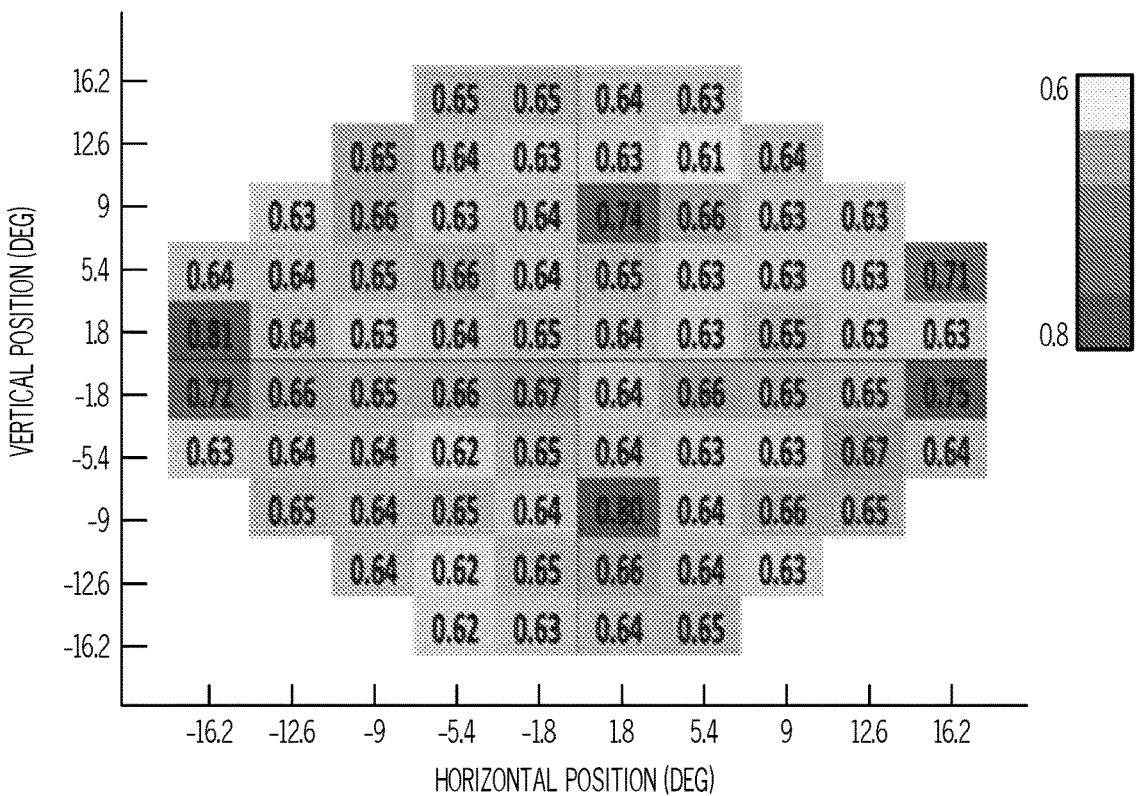

The pupil response parameters with respect to each test point for red and blue light stimuli were characterized for each of the control participants. FIGS. 4A-4F demonstrate maps of mean PPC (FIGS. 4A and 4B), MCV (FIGS. 4C and 4D), and LMCV (FIGS. 4E and 4F) recorded from control participants in each test point location, in response to red light stimuli (FIGS. 4A, 4C, 4E) and blue light stimuli (FIGS. 4B, 4D, 4F). The mean PPC recorded in response to blue light stimuli ranged from 13-28% at different test point locations (mean±SE: 19.4±0.22,) and was significantly higher compared with the red light stimuli (range 7-22%, mean±SE: 12±0.2, t-test p<0.0001), even though the red light stimuli were presented at a five-fold higher intensity than the blue light stimuli. Similarly, the mean MCV was significantly higher in response to blue light stimuli (range 28-43 pixel/sec, mean±SE: 37±0.3 pixel/sec) as compared with the red light stimuli (range 18-36 pixel/sec, mean±SE: 23.17±3, t-test p=2×10-7). There was no significant difference in the mean LMCV between the red and blue light (range 0.6-0.8 sec, t-test p=0.11). Higher PPC was recorded in central locations of the VF compared to peripheral locations in response to both red and blue light (FIGS. 4A and 4B). A similar pattern of faster mean MCV in central locations compared to peripheral locations was clearly demonstrated in response to red light stimuli (FIG. 4C). The central-peripheral gradient pattern was less evident in response to blue light (FIG. 4D). The LMCV parameter was relatively constant throughout the VF field, in response to both red and blue light with an interquartile range of 0.6-0.7 seconds. The longest LMCV values were measured at peripheral test points in response to both wavelengths (FIGS. 4E and 4F).

Figure 5A:
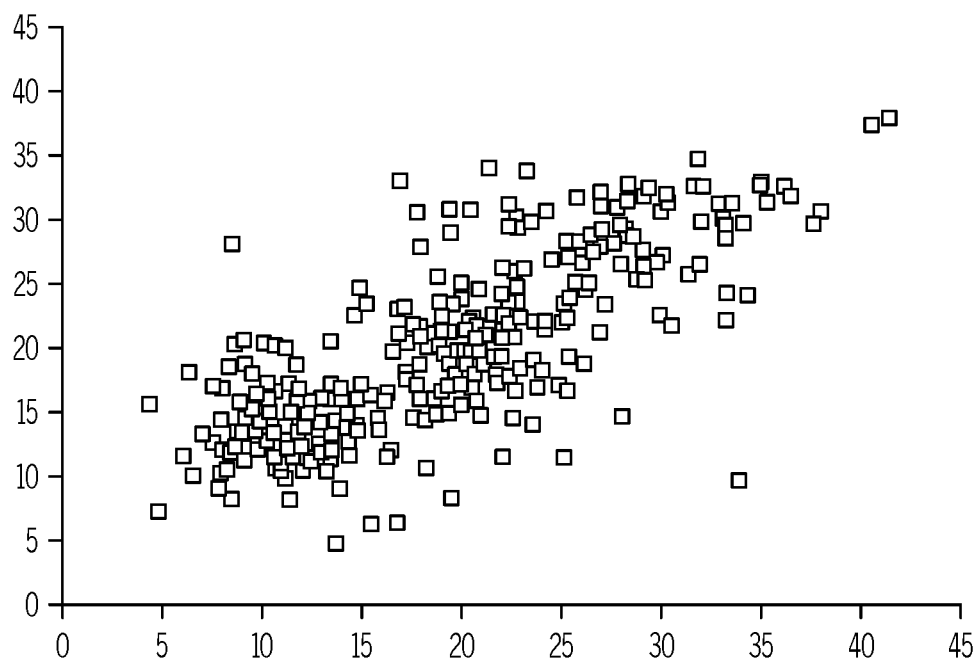
FIGS. 5A-5F illustrate results of a test and retest of PPC (FIG. 5A—blue light, FIG. 5B—red light), MCV (FIG. 5C—blue light, FIG. 5D—red light), and LMCV (FIG. 5E—blue light, FIG. 5F—red light) in healthy subjects, where the x-axis of each plot corresponds to the first test, and the y-axis of each plot corresponds to the retest according to one or more embodiments shown and described herein.
Figure 5B:
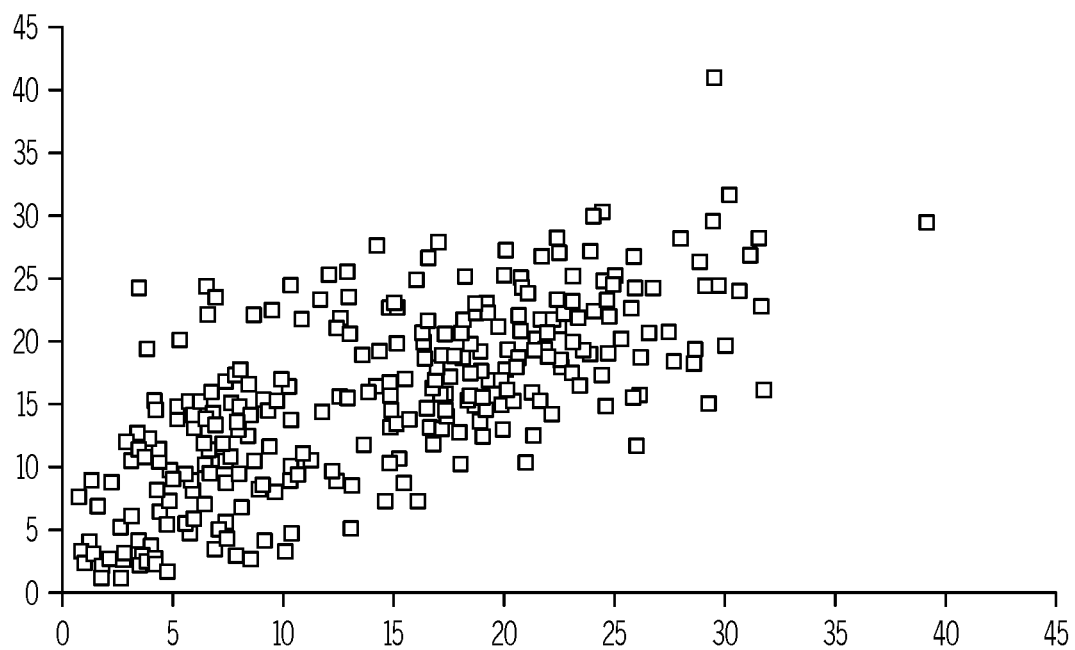
Figure 5C:
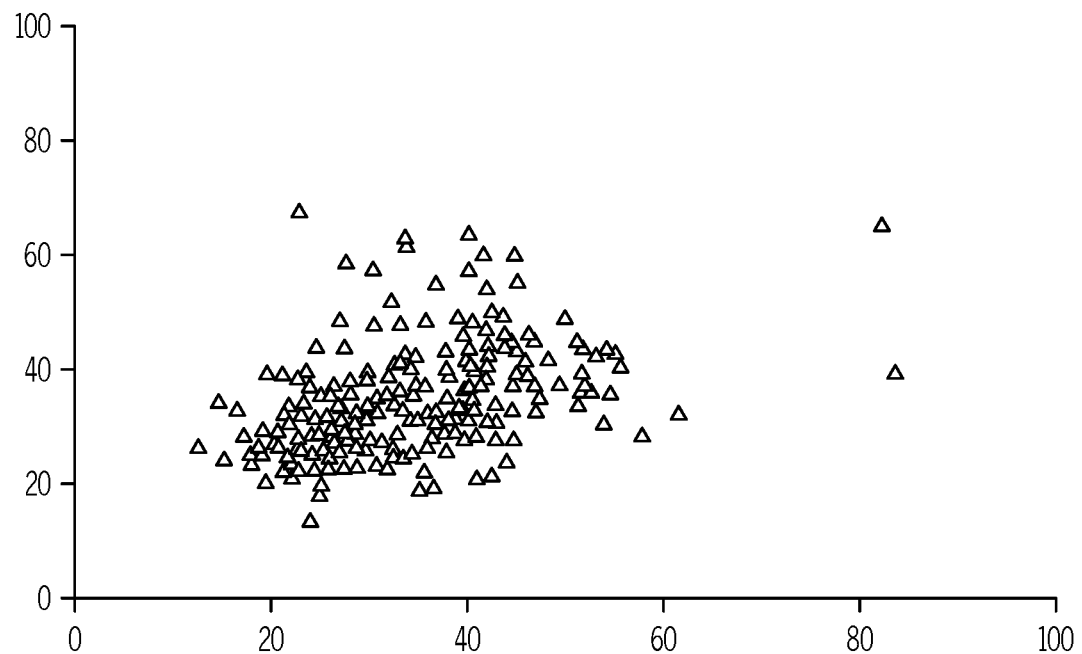
Figure 5D:
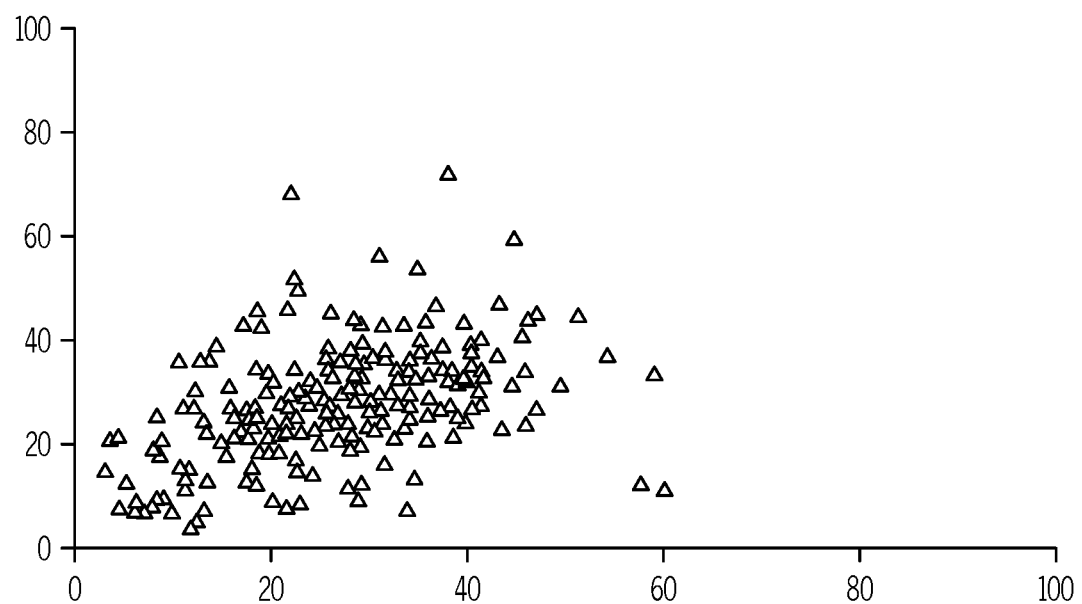
Figure 5E:
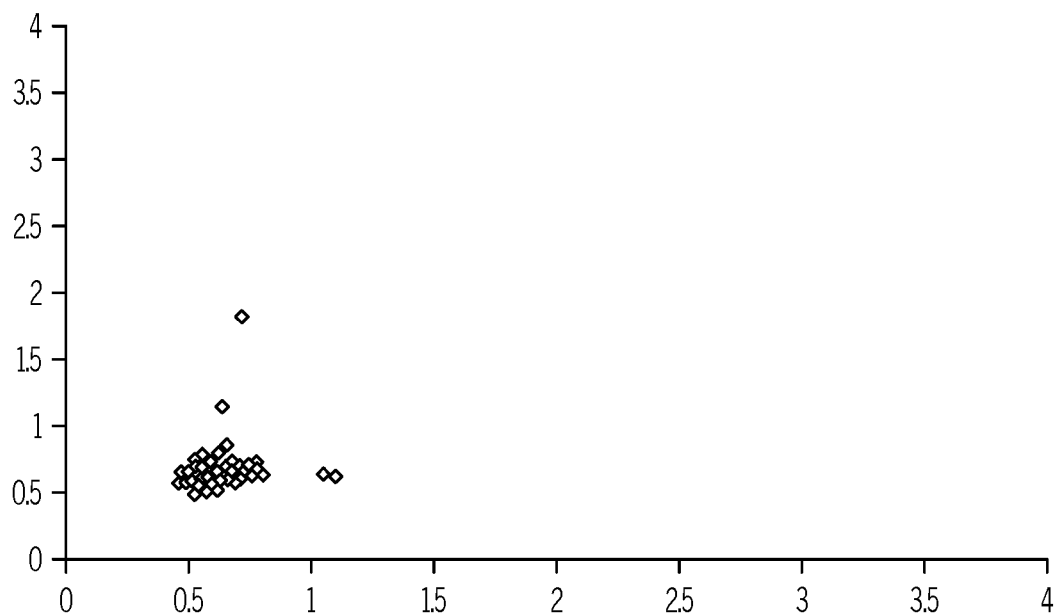
Figure 5F:
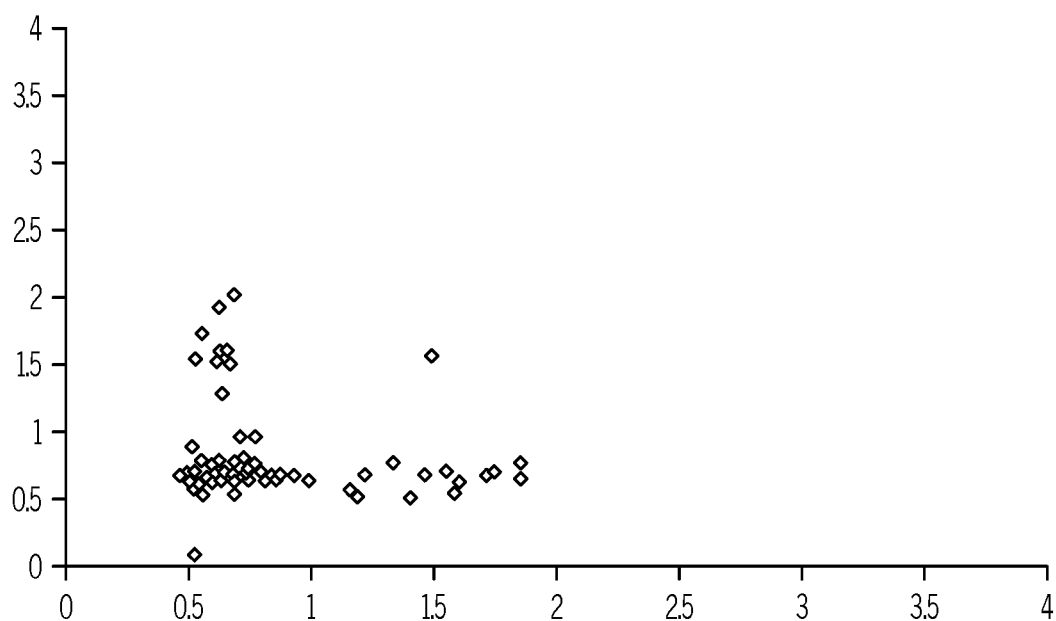

Referring to FIGS. 5A-5F, the test and retest results of PPC (FIGS. 5A and 5B), MCV (FIGS. 5C and 5D) and LMCV (FIGS. 5E and 5F) in healthy subjects in response to red light stimuli (FIGS. 5A, 5C, 5E) and blue light stimuli (FIGS. 5B, 5D, 5F). The x-axis of each plot corresponds to the first test and the y-axis of each plot corresponds to the retest. Test reliability was assessed by retesting 6 healthy controls and examining pupil response data originating from 685 stimuli (319 blue, 366 red). A good linear correlation between the test and the retest was demonstrated for the parameter PPC for both colors (red—R2=0.721, p<0.0001, FIG. 5A; blue—R2=0.762, P<0.0001, FIG. 5B). The MCV parameter demonstrated lower but still reasonable correlation between test and retest (red—R2=0.522, p<0.0001, FIG. 5C; blue—R2=0.513, P<0.0001, FIG. 5D). The lowest correlation between test and retest was recorded for the LMCV parameter (red—R2=0.208, p<0.0001, FIG. 5E; blue—R2=0.419, P<0.0001, FIG. 5F).

Additionally, the relationship between disease severity and the pupil response parameters was analyzed. RP patients demonstrated diminished pupil responses in correlation with disease severity. Thirteen RP patients were divided into 2 groups, based on their DA-GVF testing results. Group A consisted of 5 patients with some functional DA-GVF in response to red and blue light, while Group B included 8 patients with a severe disease with no detection of either blue or red light in the DA-GVF (Table 1).

TABLE 1

Summary of Patient Characteristics

| | | | | | | ERG | | | | | | | | | |
|---|---|---|---|---|---|---|---|---|---|---|---|---|---|---|---|
| | | | | | | Isolated rod response | | Dark adapted ERG a-wave | | Dark adapted ERG b-wave | | Single flash ERG a-wave | | Single flash ERG b-wave | |
| Subject | Gender | Age (y) | Diagnosis | BCVA | Group | Max | IT | Max | IT | Max | IT | Max | IT | Max | IT |
| 1 | M | 34 | RP | 20/40 | B | ND | ND | ND | ND | ND | ND | ND | ND | ND | ND |
| 2 | M | 44 | RP | 1/24 | A | 74 | 100 | 95 | 24.5 | 149 | 39 | 16 | 16 | 26 | 33 |
| 3 | F | 34 | RP | 20/25 | A | ND | ND | 15 | 17 | 11 | 42 | 21 | 6 | 33 | 23 |
| 4 | F | 32 | RP | 20/32 | A | ND | ND | ND | ND | 5 | 36 | ND | ND | 5 | 30 |
| 5 | M | 20 | US | 1/24 | A | 49 | 78 | 16 | 30 | 34 | 51 | 9 | 31 | 5 | 26 |
| 6 | F | 31 | RP | 20/20 | A | ND | ND | 15 | 19 | 7 | 44 | 7 | 16 | 13 | 46 |
| 7 | M | 27 | RP | 20/50 | B | ND | ND | ND | ND | ND | ND | ND | ND | ND | ND |

TABLE 1-continued

Summary of Patient Characteristics

| | | | | | | ERG | | | | | | | | | |
|---|---|---|---|---|---|---|---|---|---|---|---|---|---|---|---|
| | | | | | | Isolated rod response | | Dark adapted ERG a-wave | | Dark adapted ERG b-wave | | Single flash ERG a-wave | | Single flash ERG b-wave | |
| Subject | Gender | Age (y) | Diagnosis | BCVA | Group | Max | IT | Max | IT | Max | IT | Max | IT | Max | IT |
| 8 | M | 55 | RP | 20/63 | B | ND | ND | ND | ND | ND | ND | ND | ND | ND | ND |
| 24 | M | 21 | RP | 20/64 | B | ND | ND | 6 | 14 | 26 | 57 | 9 | 26 | 22 | 38 |
| 25 | M | 22 | RP | 20/640 | B | ND | ND | 15 | 17 | 17 | 44 | 10 | 17 | 10 | 26 |
| 26 | M | 28 | RP | 20/20 | B | ND | ND | ND | ND | ND | ND | ND | ND | ND | ND |
| 29 | M | 65 | RP | 20/30 | B | ND | ND | ND | ND | ND | ND | ND | ND | ND | ND |
| 30 | M | 58 | RP | 20/50 | B | ND | ND | ND | ND | ND | ND | ND | ND | ND | ND |

Age is reported in years. Group A—indicated some light detection in response to both red and blue by DA-GV. Group B—indicated no light detection in response to at least one color by DA-GVF. Abbreviations: F—Female, M—Male, AS—Usher Syndrome, RP—Retinitis pigmentosa, BCVA—Best corrected Visual Acuity, ERG—Electroretinography, IT—implicit time (in milliseconds), Max—Maximal response (in □V), ND—Not detected.

Figure 6A:
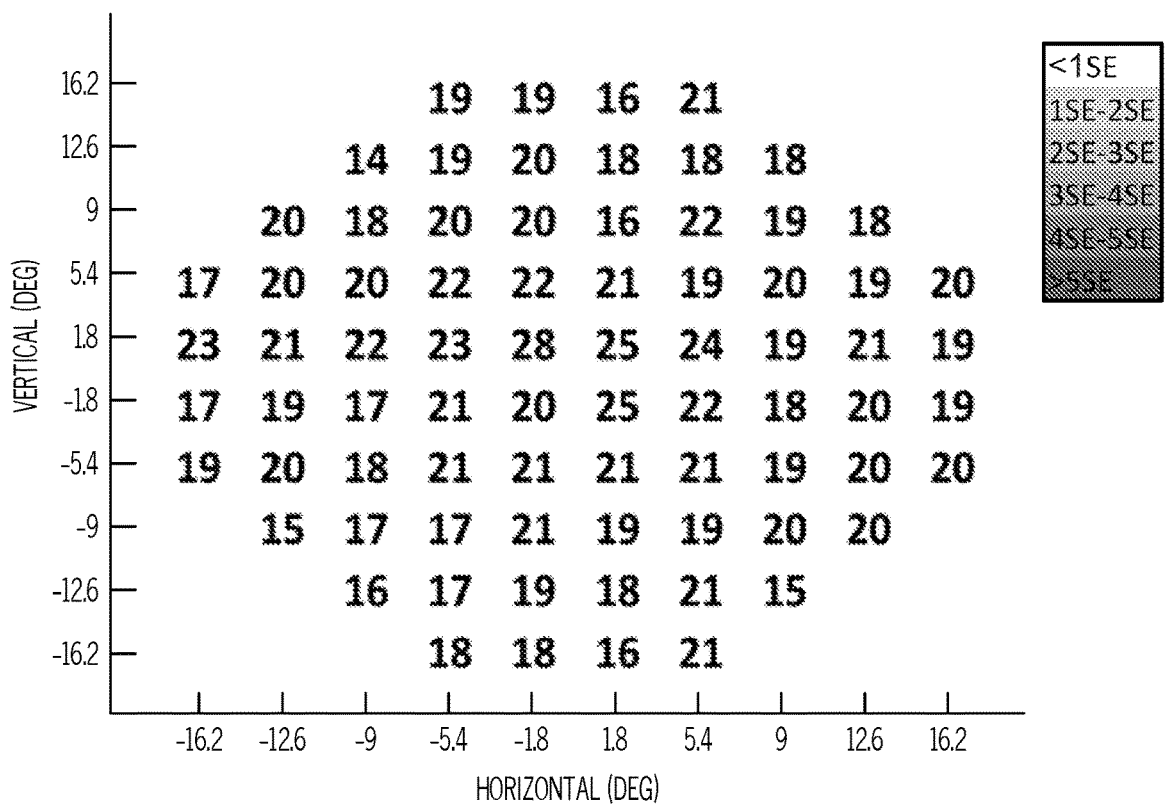
FIGS. 6A-6C illustrate the mean PPC parameters in response to blue light in healthy subjects (FIG. 6A), in patients from group A (FIG. 6B), and in patients from group B (FIG. 6C), for each of the 76 test targets of the 16.2 degree visual field (VF) according to one or more embodiments shown and described herein.
Figure 6B:
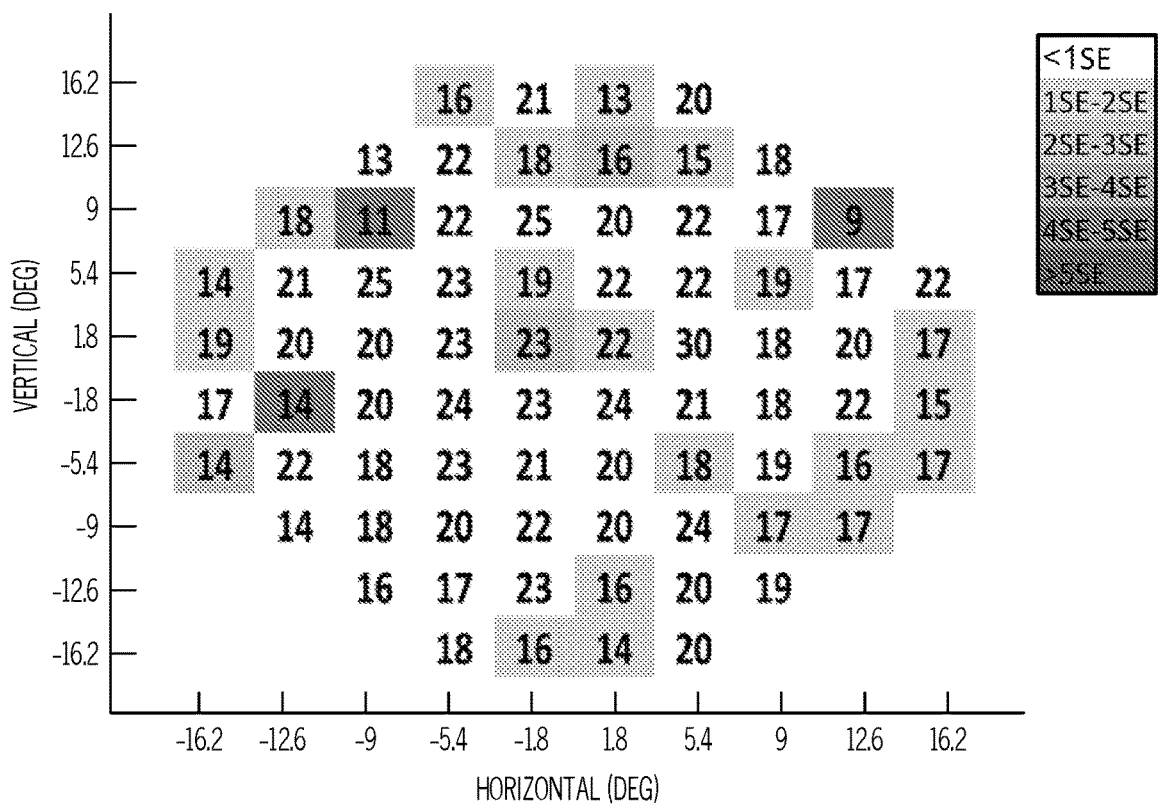
Figure 6C:
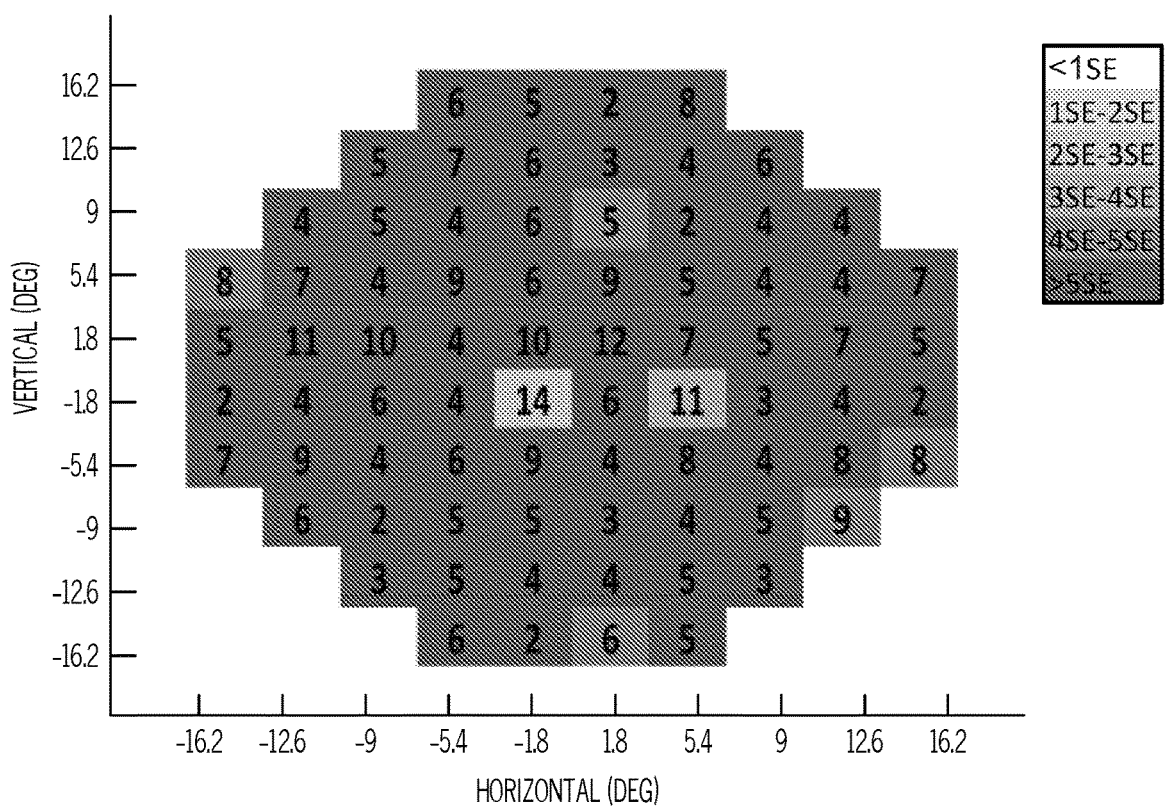
Figure 6D:
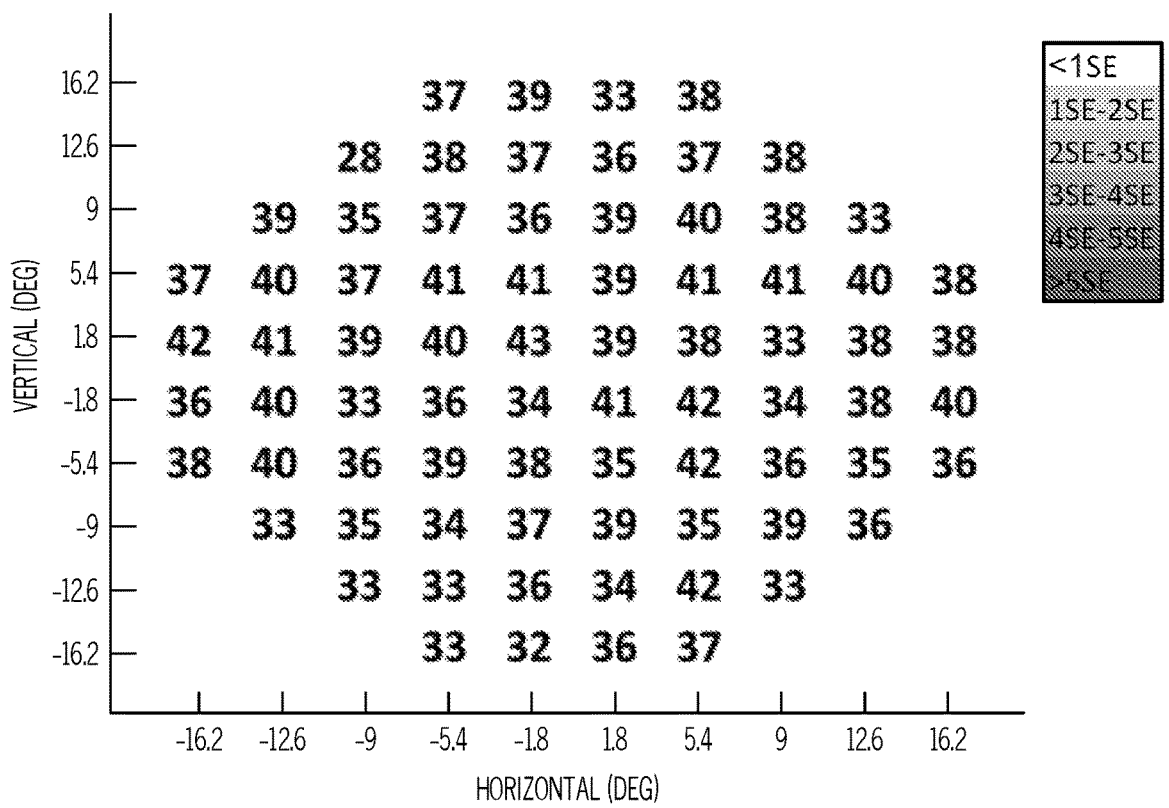
FIGS. 6D-6F illustrate the mean MCV parameters in response to blue light in healthy subjects (FIG. 6D), in patients from group A (FIG. 6E), and in patients from group B (FIG. 6F), for each of the 76 test targets of the 16.2 degree visual field (VF) according to one or more embodiments shown and described herein.
Figure 6E:
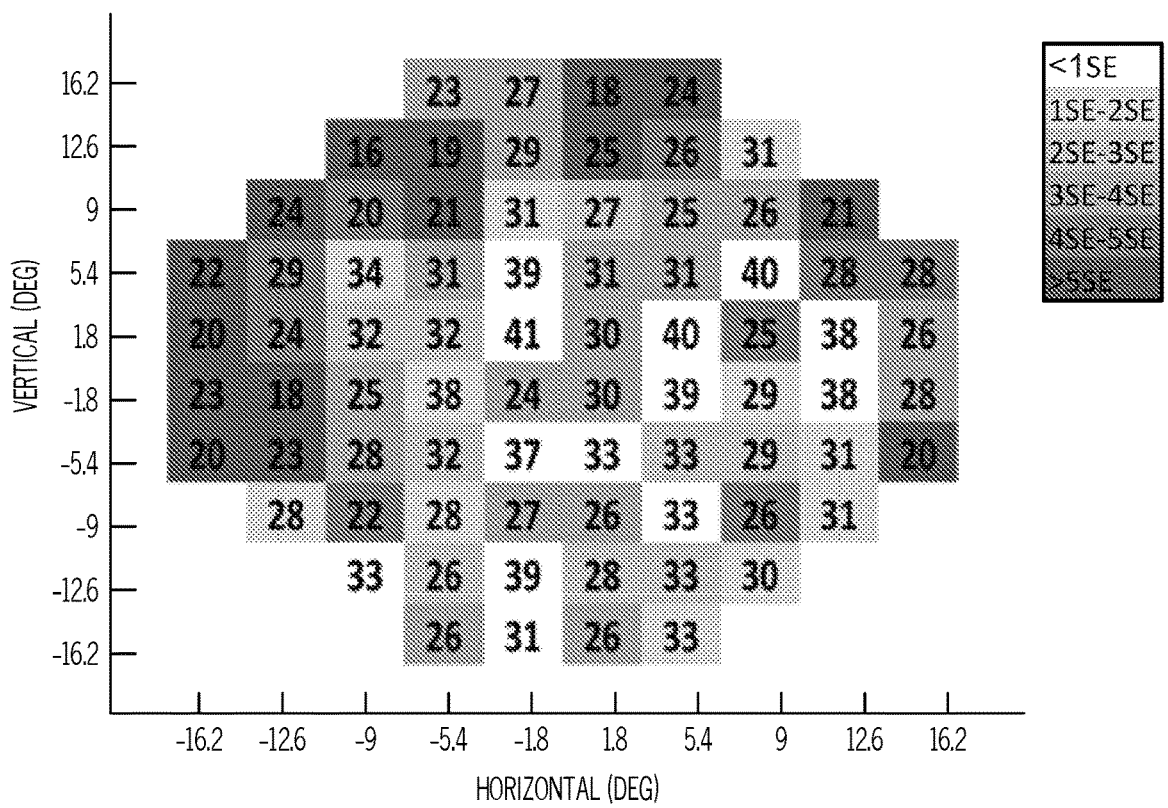
Figure 6F:
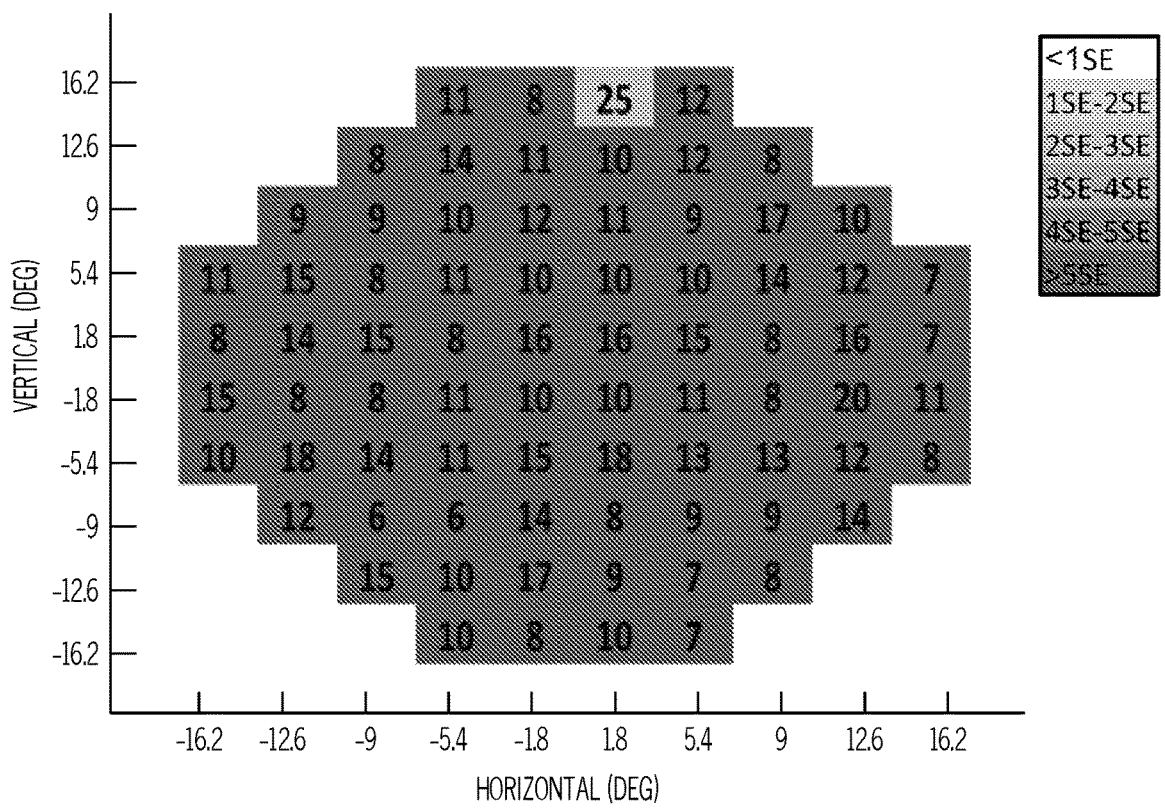
Figure 6G:
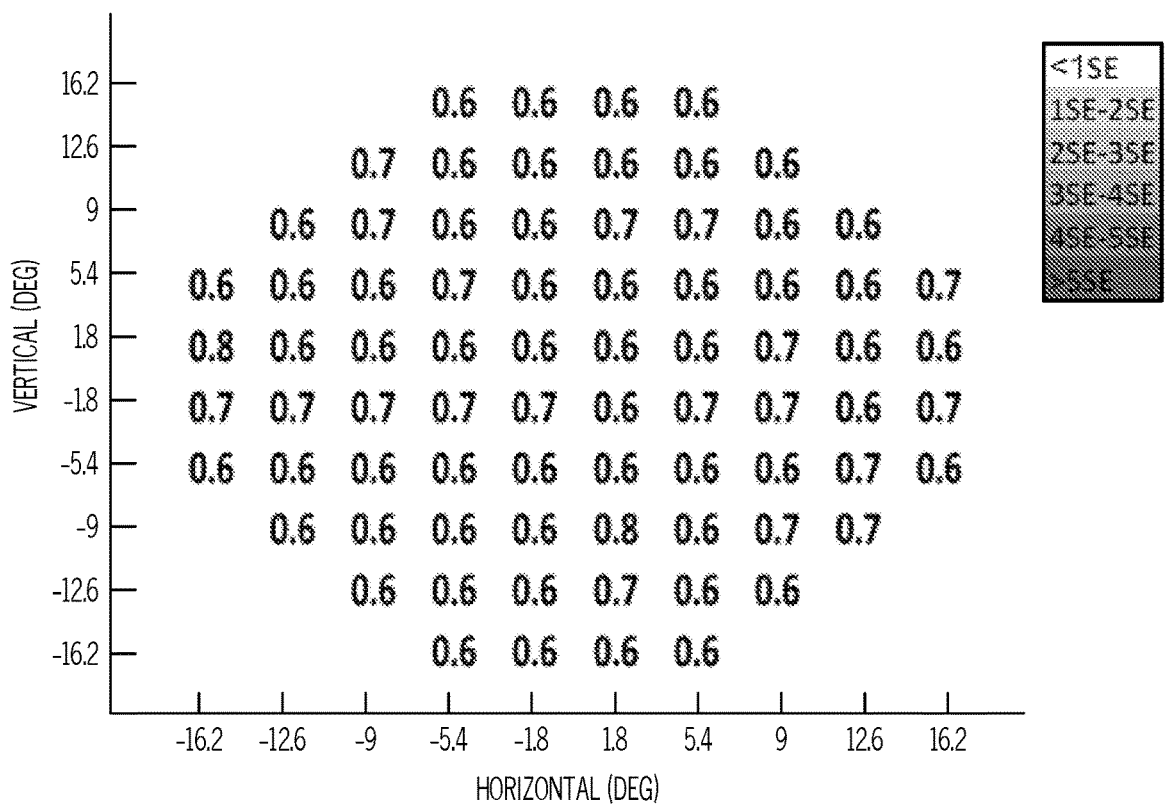
Figure 6H:
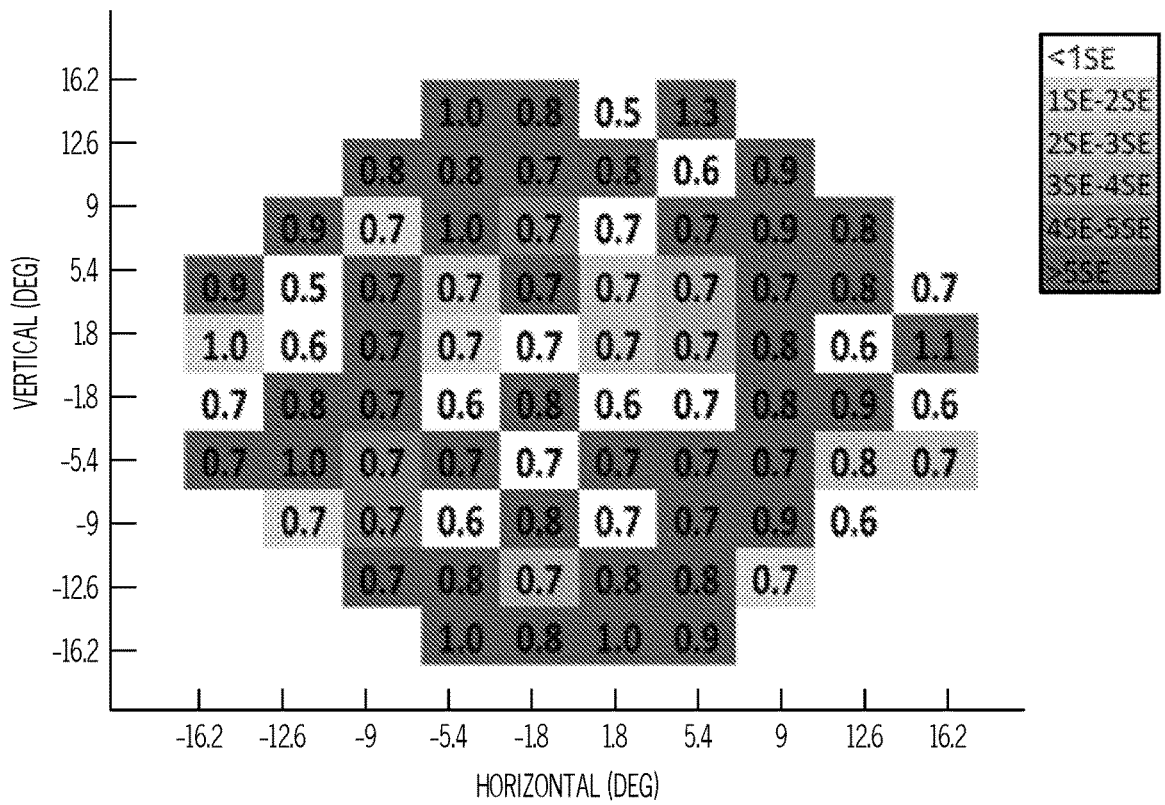
Figure 61:
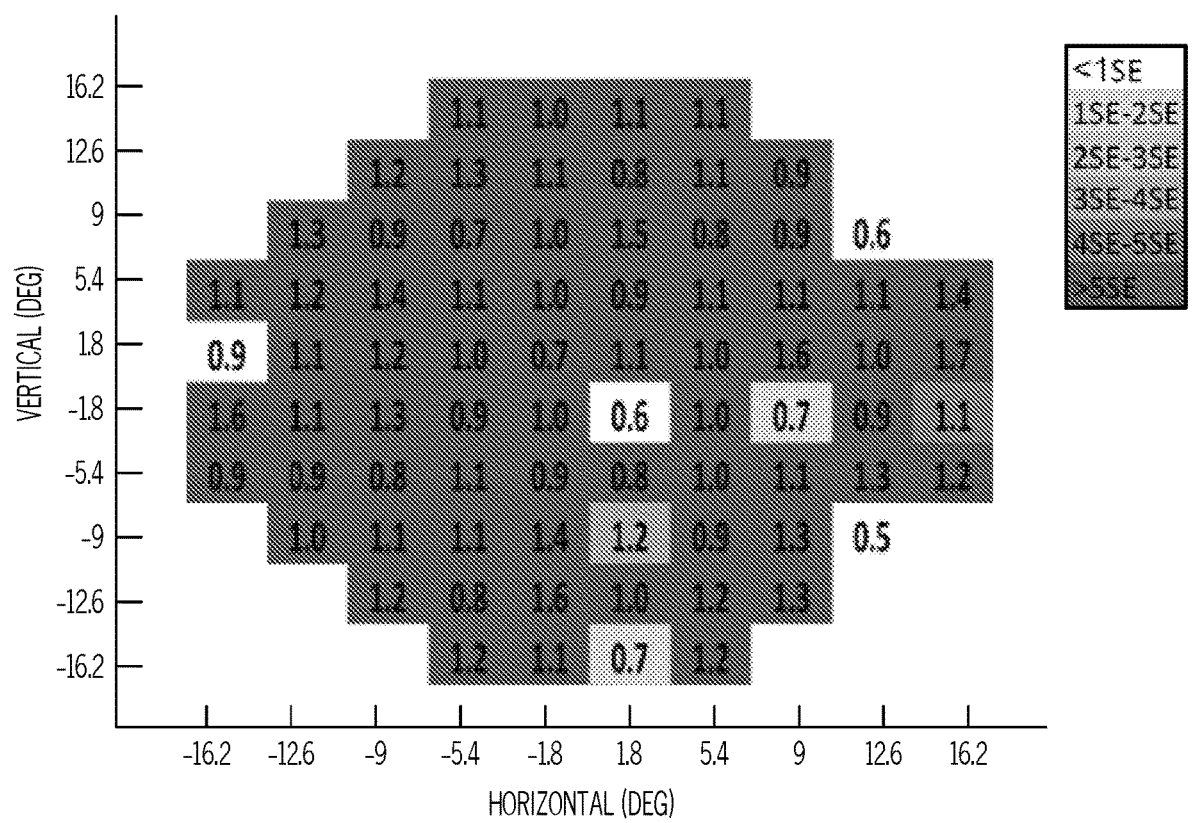

Referring to FIGS. 6A-6I, grayscale maps of mean PPC (6A-6C), MCV (6D-6F) and LMCV (6G-6I) recorded in each test point location in response to blue light in healthy subjects (See FIGS. 6A, 6D, and 6G), patients with intermediate stage of retinal degeneration (Group A; FIGS. 6B, 6E, and 6H), and patients with severe stage retinal degeneration (Group B; FIGS. 6C, 6F, 6I) are illustrated. Grayscale coding was set with white color for normal values and darker colors for values that were lower than normal. Normal values were set as the mean of healthy subjects in each test point location. Deviation from normal was determined based on the standard errors (SEs) calculated for each parameter in each target point in the healthy subjects. Thus, for PPC and MCV parameters darkest color was used for test points in which the mean of patients was lower than 5 SEs away from the mean of healthy subjects in those points. For the LMCV parameter, darkest color was used for test points in which the mean of patients was higher than 5 SEs away from the mean of healthy subjects in those points. In Group B, the mean PPC and MCV parameters in response to the blue light were lower than 5 SEs away from the mean of healthy subjects in nearly all test point locations (FIGS. 6C and 6F). Similarly, the mean LMCV was higher than 5 SEs away from the mean of healthy subjects in 68 out of the 76 test points (FIG. 6I).

By contrast, the mean PPC recorded in Group A patients was equal to or was lower by less than 2 SEs away from the mean of healthy subjects in majority of the VF (50 test points, FIG. 6B). For 26 test points, mostly located in the periphery of the VF, the mean PPC of Group B patients was lower than 2 SEs away from the mean of healthy subjects. The MCV and LMCV parameters also demonstrated an intermediate defect in pupil response. Thus, in 33 and 25 test point locations, the mean MCV and LMCV, respectively, were lower than 3 SEs away from the mean of healthy subjects (FIGS. 6E and 6H).

Figure 7A:
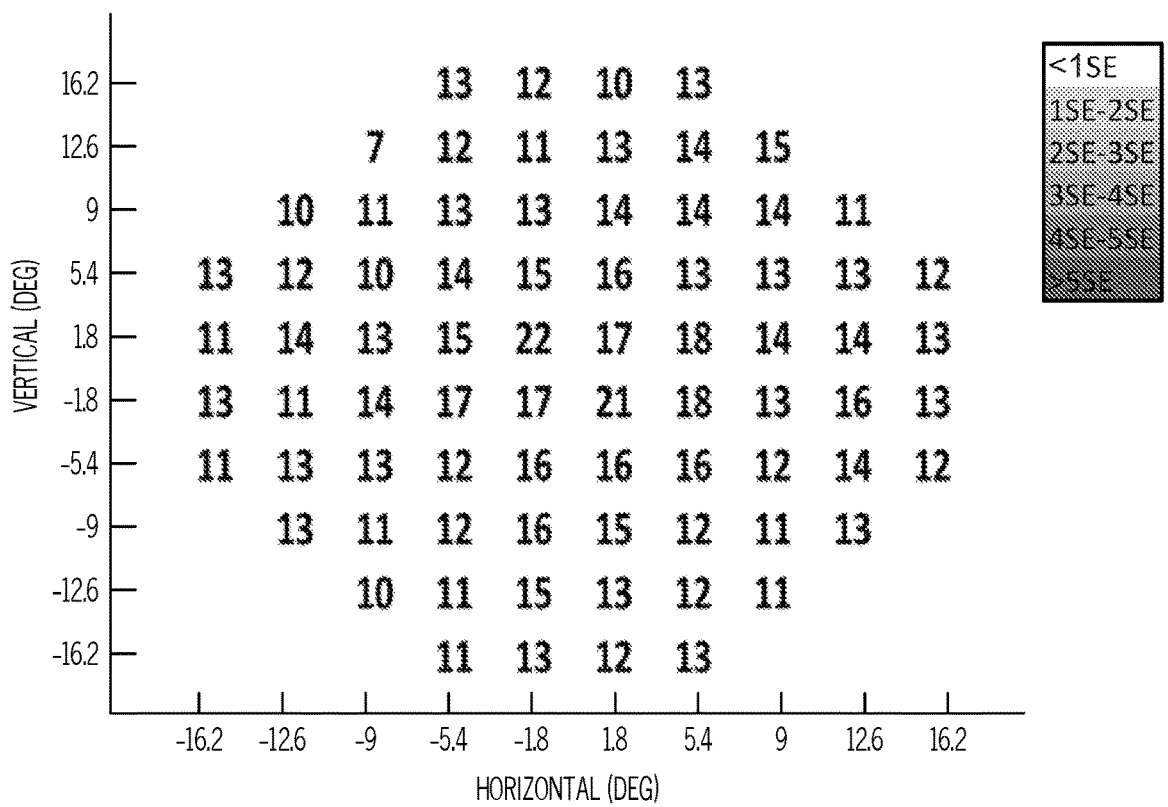
FIGS. 7A-7C illustrate the mean PPC parameters in response to blue light in healthy subjects (FIG. 7A), in patients from group A (FIG. 7B), and in patients from group B (FIG. 7C), for each of the 76 test targets of the 16.2 degree visual field (VF) according to one or more embodiments shown and described herein.
Figure 7B:
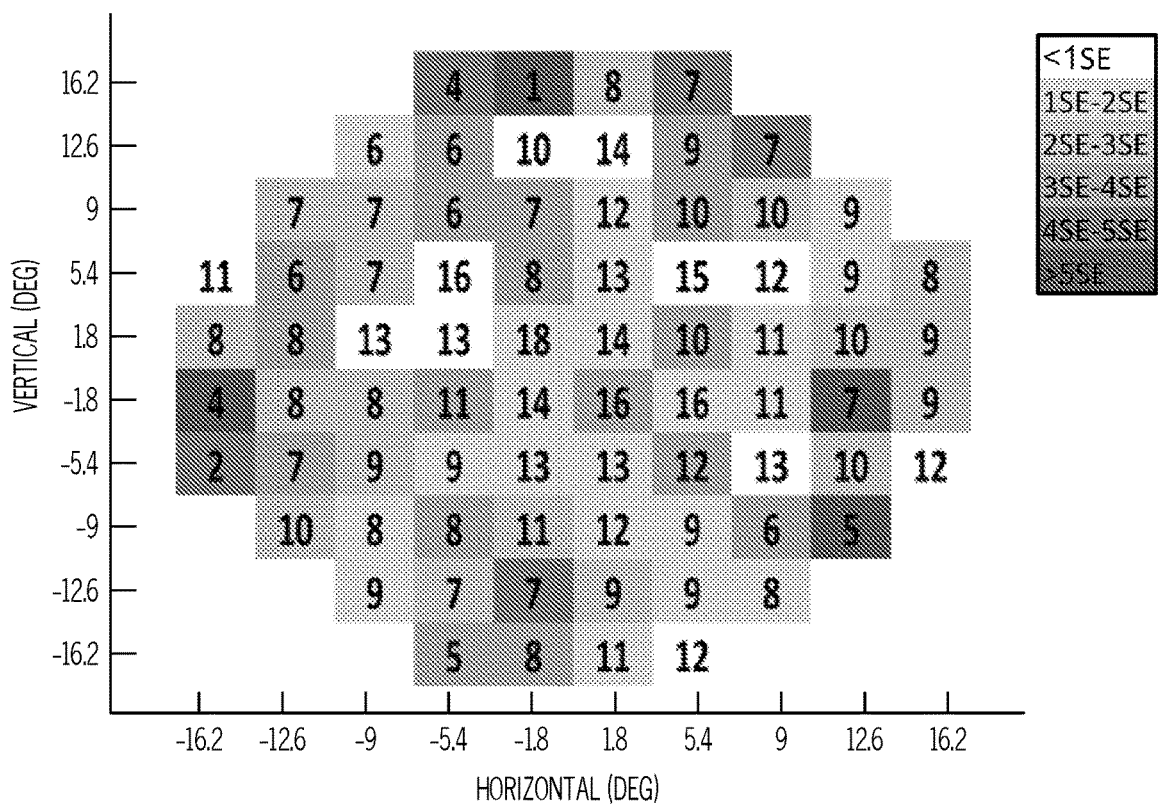
Figure 7C:
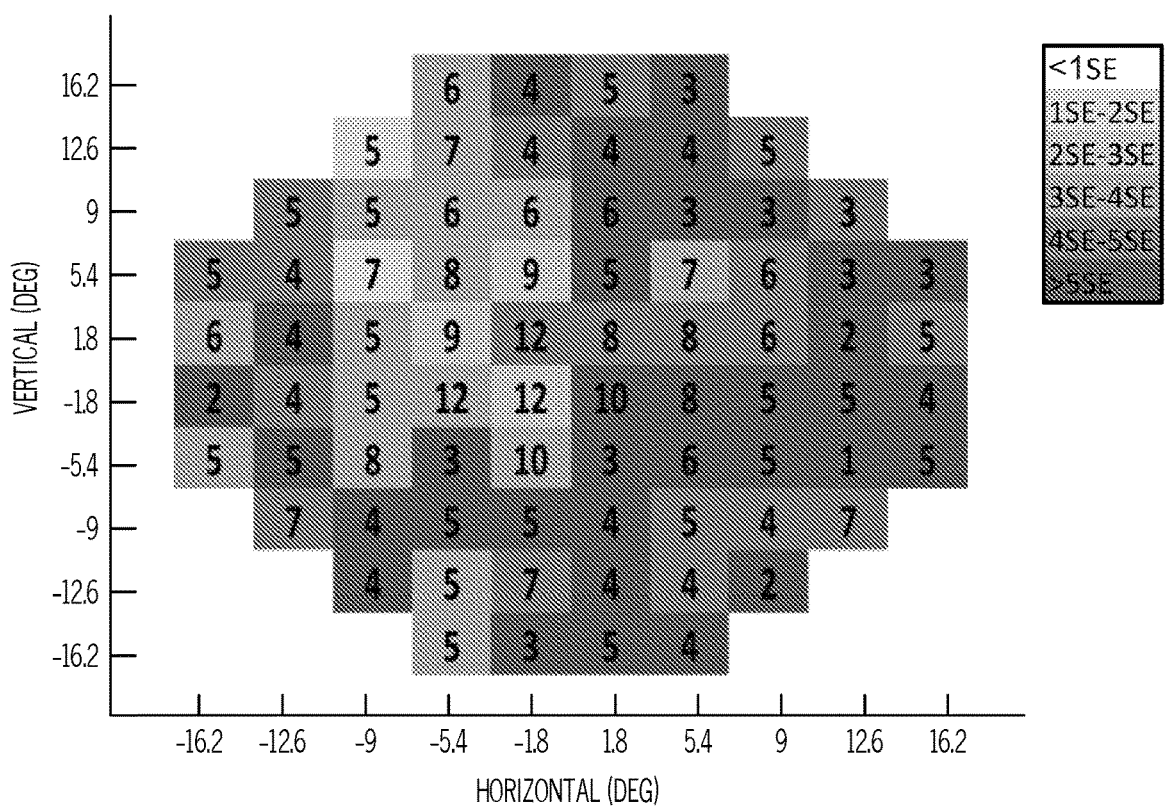
Figure 7D:
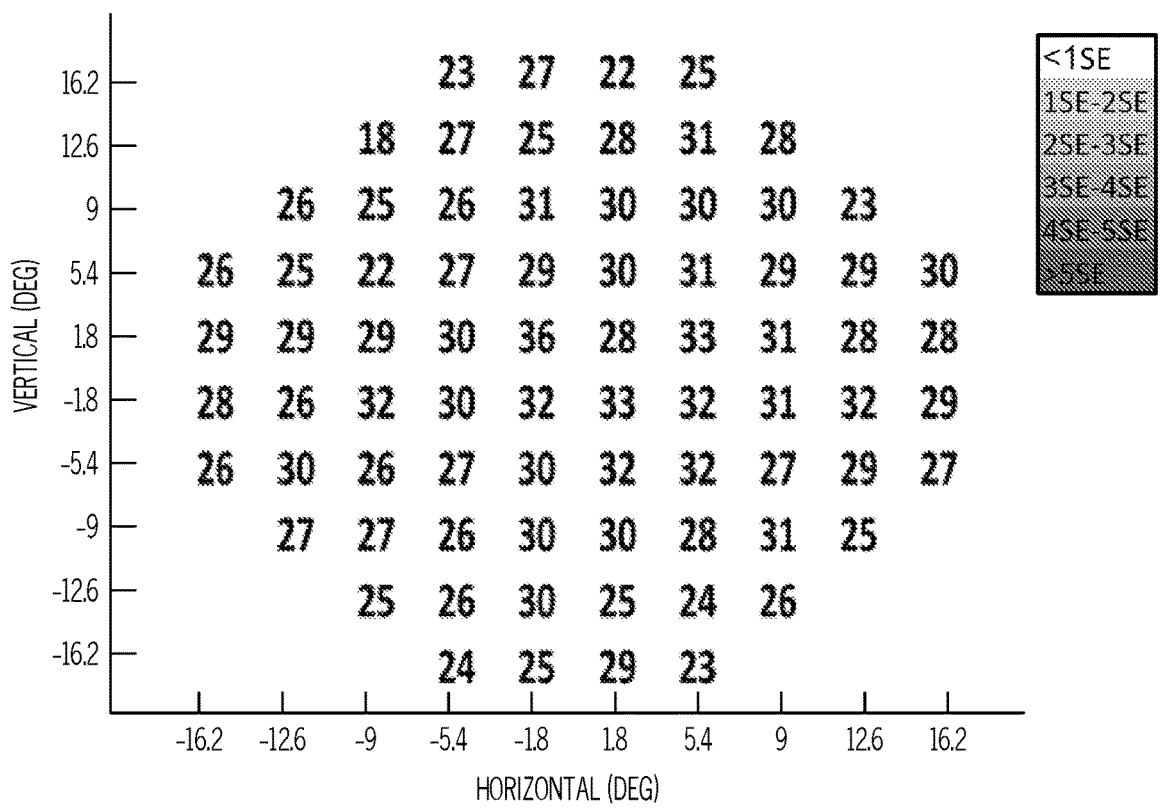
FIGS. 7D-7F illustrate the mean MCV parameters in response to blue light in healthy subjects (FIG. 7D), in patients from group A (FIG. 7E), and in patients from group B (FIG. 7F), for each of the 76 test targets of the 16.2 degree visual field (VF) according to one or more embodiments shown and described herein.
Figure 7E:
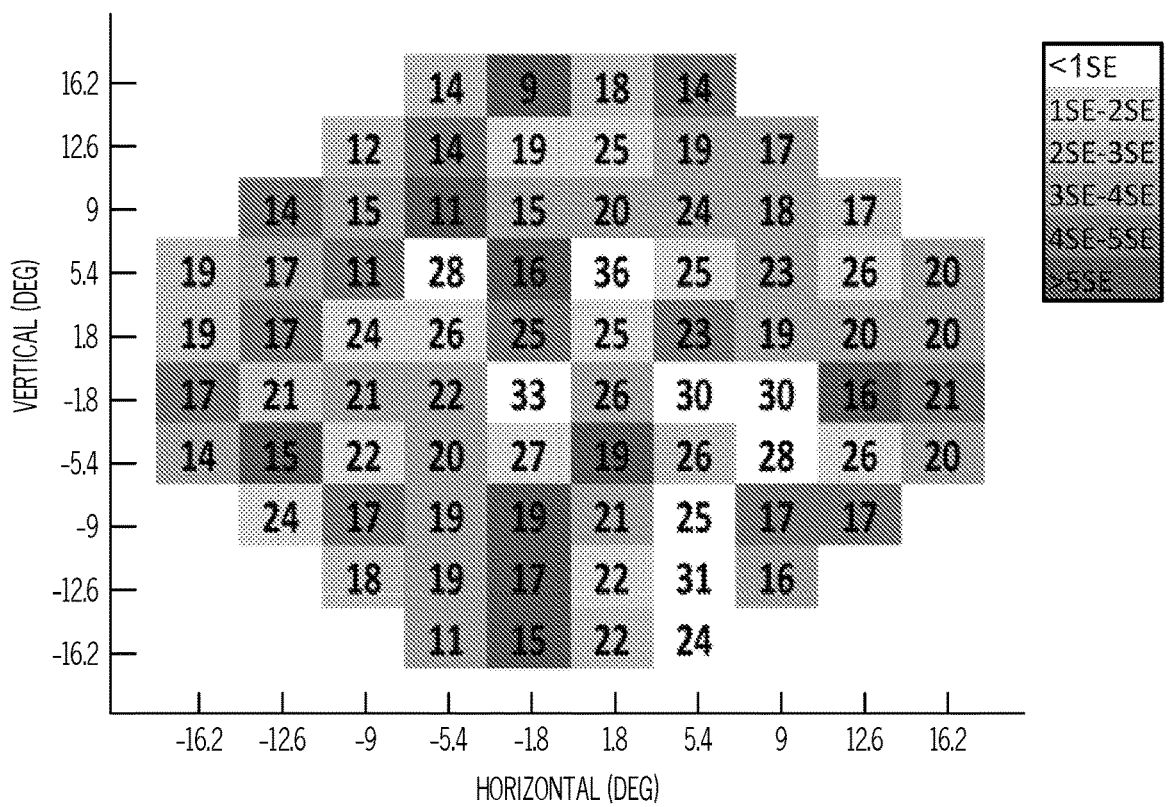
Figure 7F:
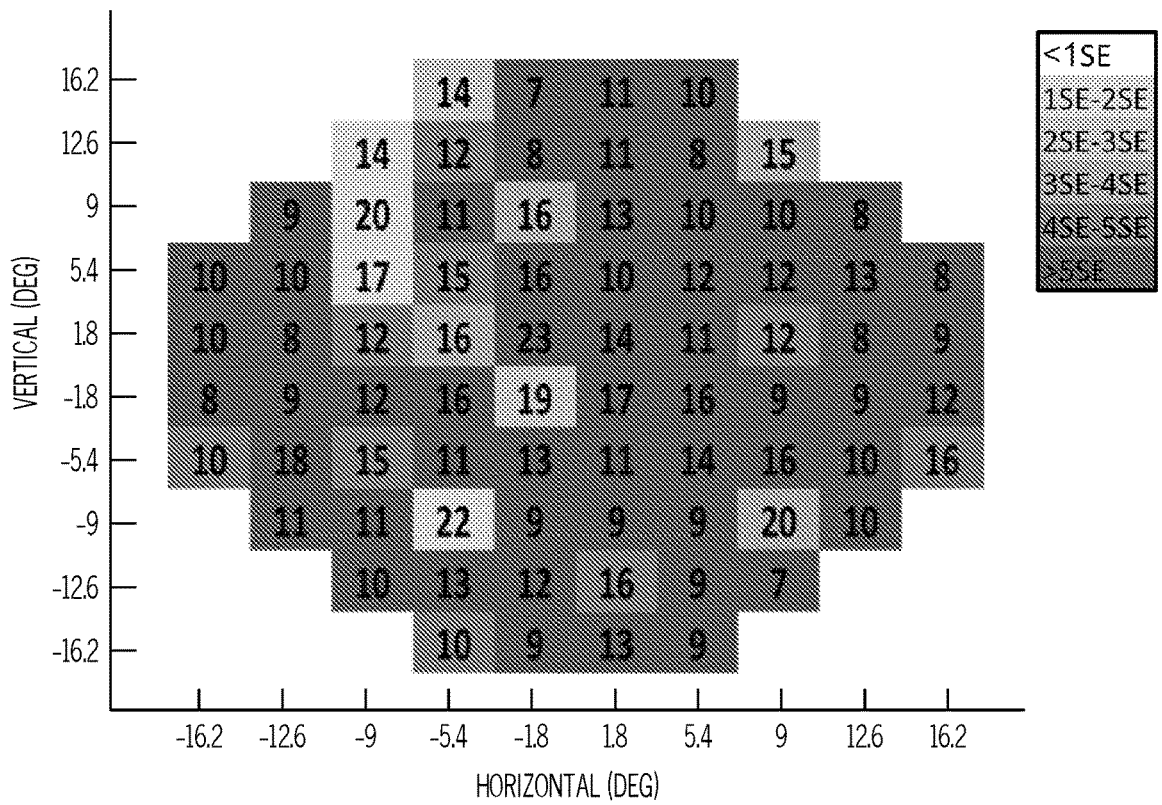
Figure 7G:
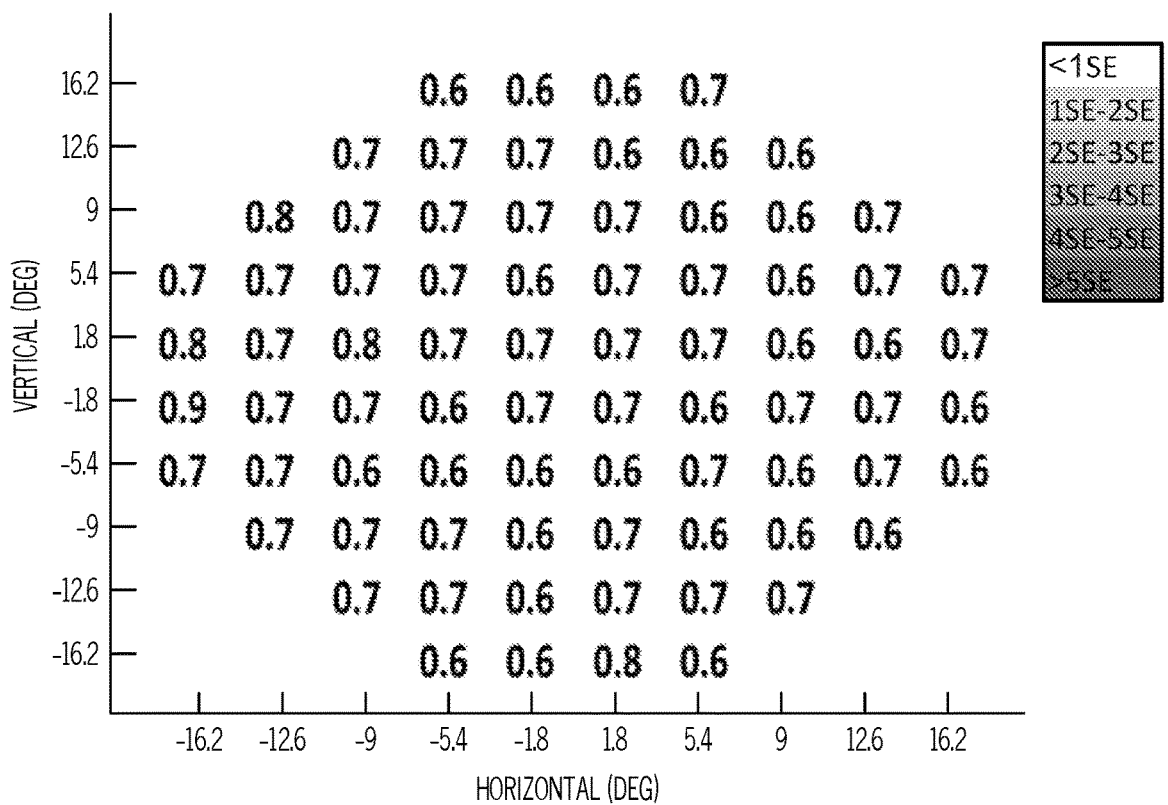
Figure 7H:
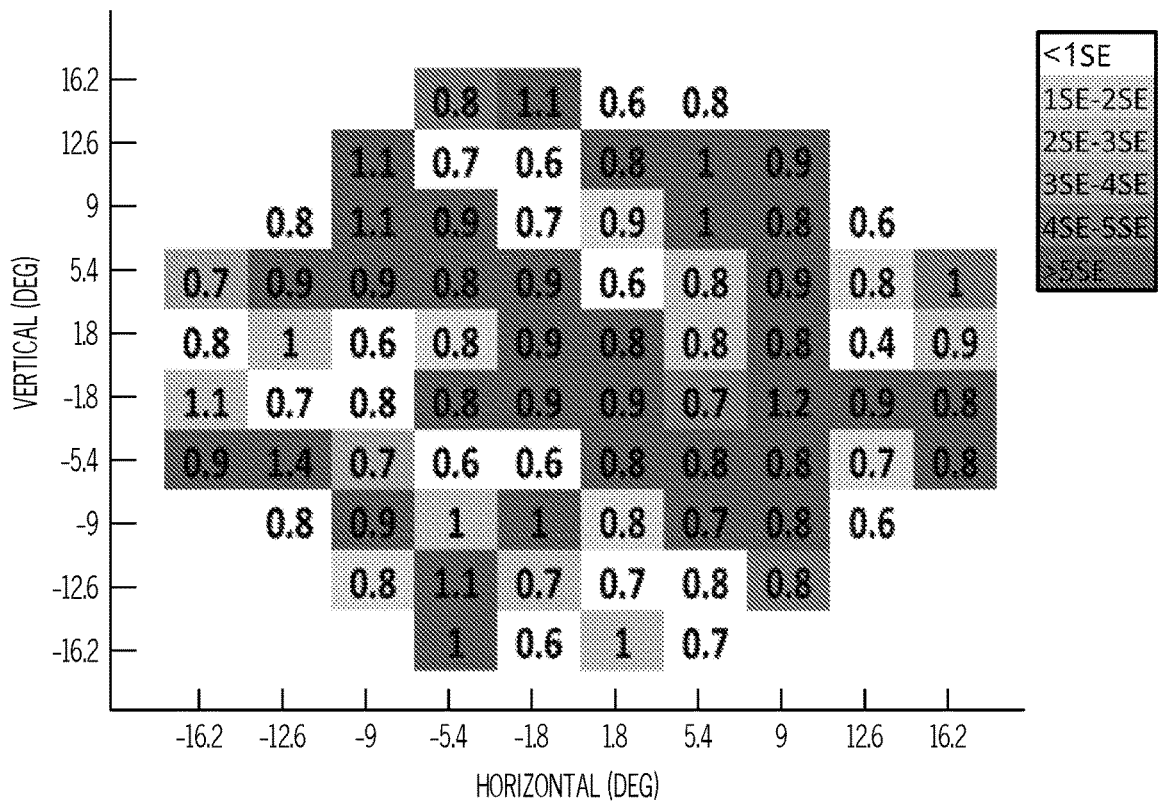
Figure 71:
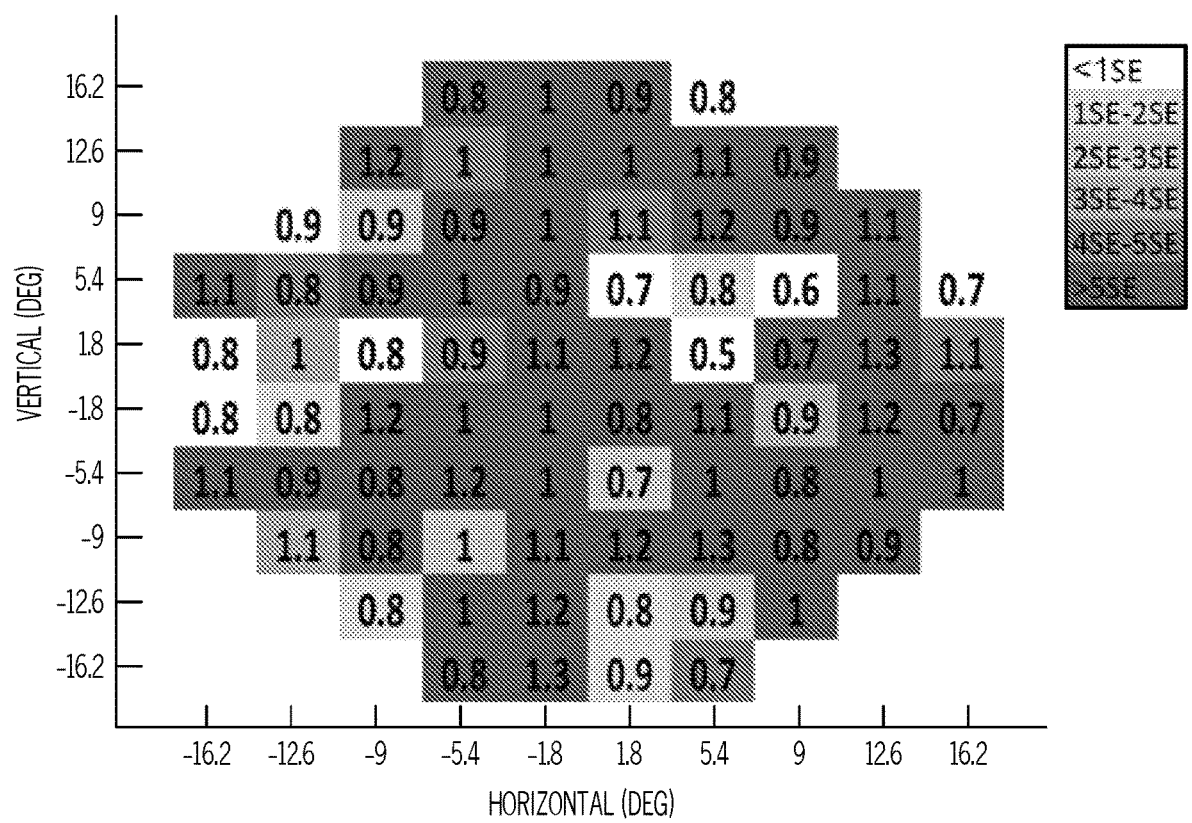

Referring to FIGS. 7A-7I, the mean PPC (FIGS. 7A, 7B and 7C), mean MCV (FIGS. 7D, 7E, and 7F) and mean LMCV (FIGS. 7G, 7H, and 7I) parameters in response to red light in healthy subjects (FIGS. 7A, 7D, and 7G), Group A patients (FIGS. 7B, 7E, and 7H) and Group B patients (FIGS. 7C, 7F, and 7I) are illustrated using grayscale visual field charts, similar to FIGS. 6A-6I. FIGS. 7A-7I demonstrate the pupil responses to red light in healthy subjects and RP patients. RP patients from both groups demonstrated lower PPC and MCV and longer LMCV compared to healthy subjects, but to a smaller extent than the response to the blue light. Thus in Group B, the mean PPC and MCV were lower than 5 SEs away from the mean of healthy subjects in 35 and 57 test points, respectively (FIGS. 7C and 7F). Similarly, comparing Group B mean LMCV (FIG. 7I) to the mean LMCV (FIG. 7G) of healthy subjects, the Group B mean LMCV was higher than 5 SEs away from the mean of healthy subjects in 50 test points as compared to 68 points in response to blue light, FIG. 7I). Group A demonstrated a milder decline in pupil responses compared to Group B, with only 4 and 9 test points in which the PPC and MCV were lower than 5 SEs away from the mean of healthy subjects, respectively (FIGS. 7B and 7E). The mean LMCV was higher than 5 SEs away from the mean of healthy subjects in 31 test points of the VF (FIG. 7H).

Figure 8:
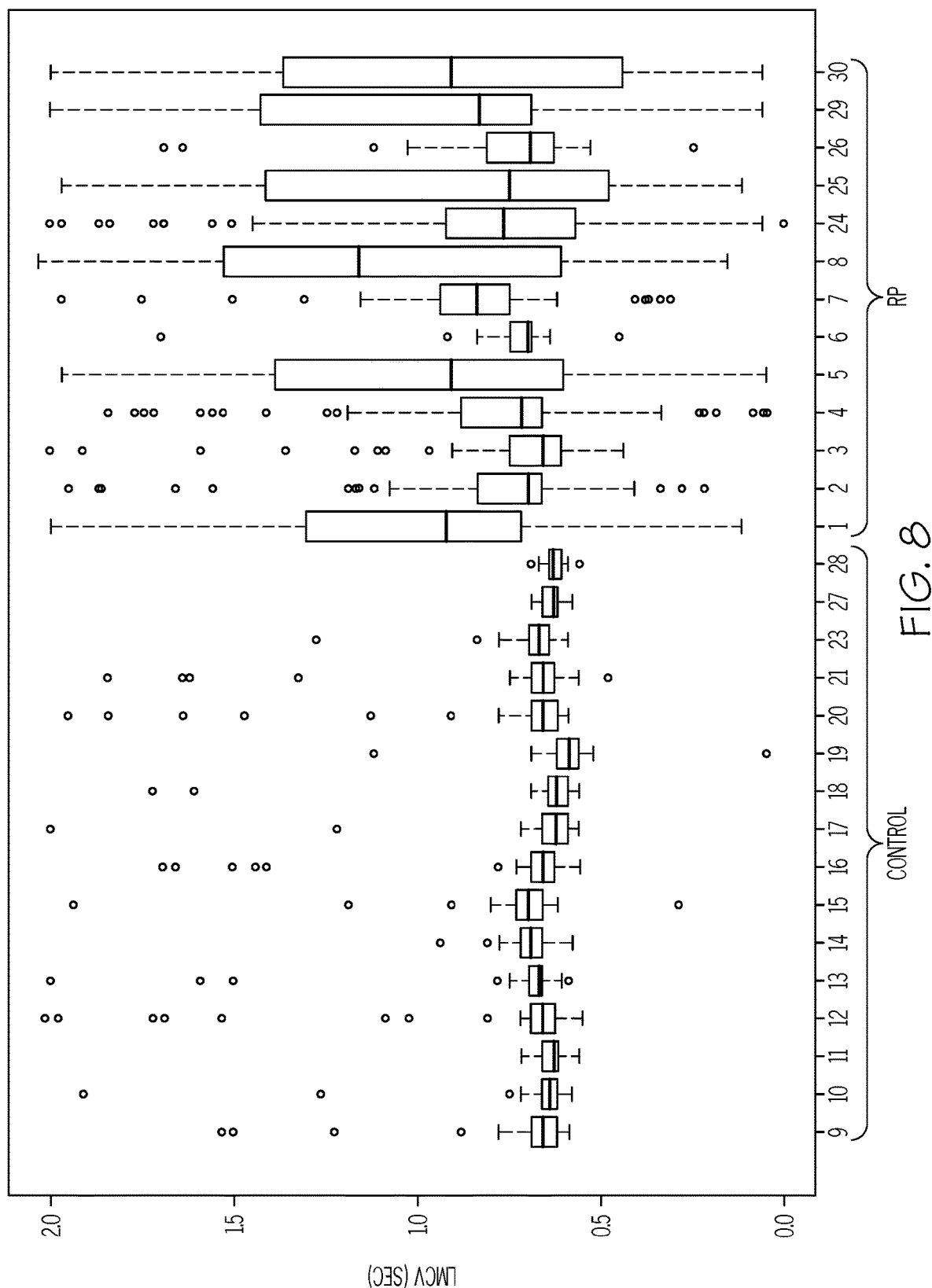
FIG. 8 illustrates the variability in the LMCV parameter in response to red light stimuli between different visual field (VF) locations in retinitis pigmentosa (RP) patients compared with control subjects according to one or more embodiments shown and described herein.

Additionally, the variability in LMCV parameter as a diagnostic tool for RP was examined. As shown in FIGS. 4A-4F and 6A-6I, the LMCV parameter was relatively constant in healthy subjects in response to blue and red light in majority of test point locations, ranging from 0.6 to 0.8 sec. By contrast, this parameter was highly variable between different test point locations in RP patients, ranging from 0.6 to 1.7 and from 0.6 to 1.4 sec in response to the blue and red light, respectively (see FIGS. 6A-6I and FIGS. 7A-7I). To evaluate the extent of the variability in LMCV between different test point locations of the VF, the mean response for each subject was determined (i.e., the mean LMCV among the subject's 76 test points). Then, the mean absolute deviation was calculated as the mean of the absolute differences between the mean and the measurements in each of the test points. FIG. 8 demonstrates for each participant a boxplot depicting the distribution of the LMCV parameter for all testing points in response to the red light. The mean absolute deviation in LMCV in response to the red light between different test points of each participant was significantly higher in patients with RP than in healthy subjects (p-value<10-6, Wilcoxon-Mann-Whitney test). In addition, the Mann-Whitney-Wilcoxon test statistic indicated that a classification method based on measurement of LMCV in response to red light would have an area under the curve (AUC) of 0.97. Similarly, the mean absolute deviation of LMCV in response to the blue light between different test points of each participant was significantly higher in patients with RP than in healthy subjects (p-value=10-4, Wilcoxon- Mann-Whitney test, with AUC of 0.93, data not shown). There was no significant difference in the absolute mean deviation of the PPC and MCV parameters between RP patients and healthy controls.

Figure 9:
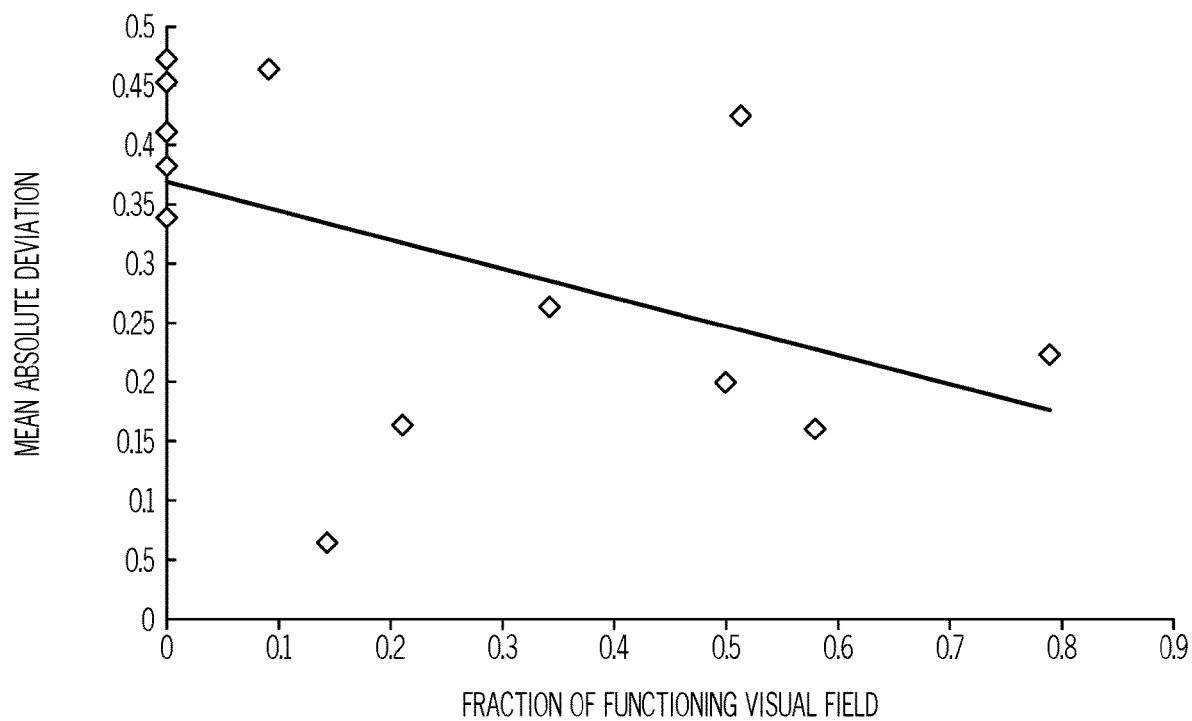
FIG. 9 illustrates a negative linear correlation between the LMCV score and corresponding results from the dark-adapted Goldmann visual field (DA-GVF) testing according to one or more embodiments shown and described herein.

Referring to FIG. 9, the mean absolute deviation in LMCV in response to the red light negatively correlated with the fraction of functional subjective VF determined by DA-GVF, Spearman's rho=−0.45, p=0.13. The highest mean absolute deviation in LMCV (>0.3) was found in patients from Group B (no light detection). By contrast, lower mean absolute deviation in LMCV (<0.3) was demonstrated in patients with some functional VF (Group A).

Figure 10:
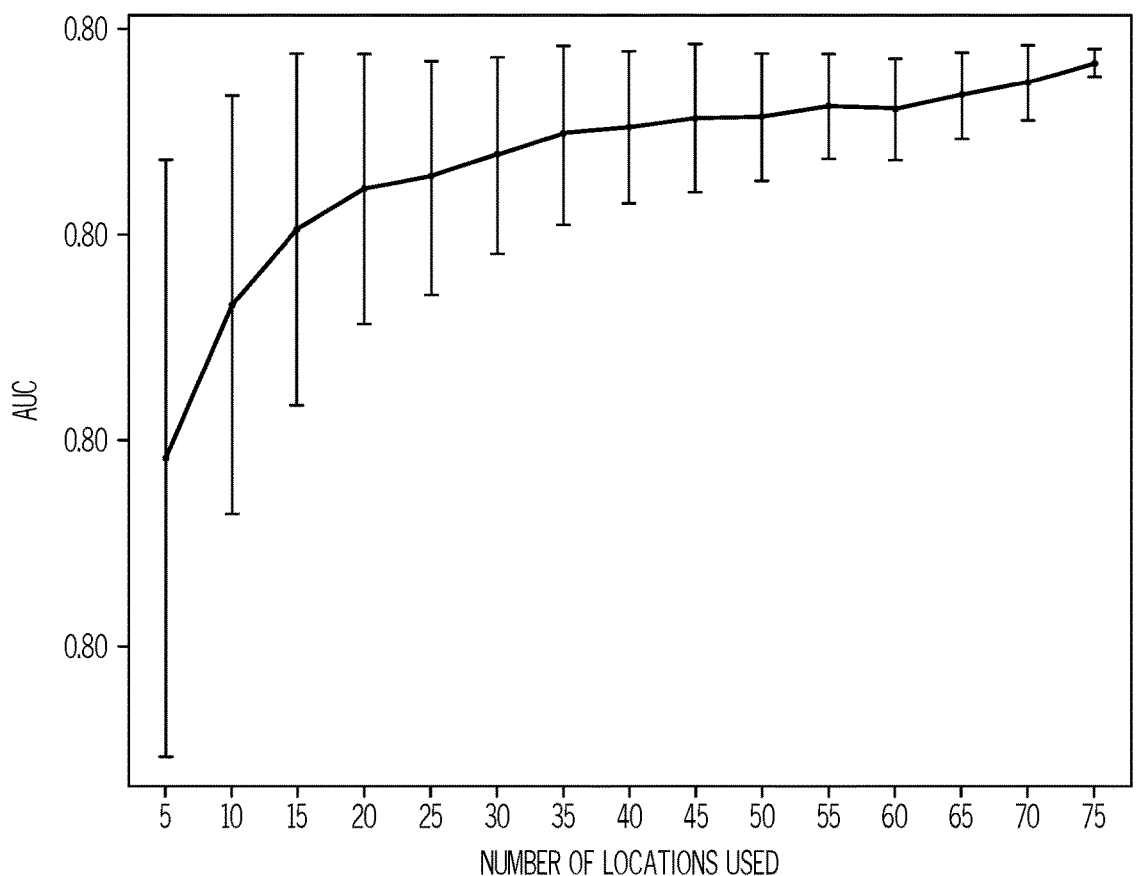
FIG. 10 illustrates a computational random selection analysis of the LMCV parameter according to one or more embodiments shown and described herein.

In an attempt to optimize the analysis of pupillometer-based perimetry and reduce testing time a fewer number of test point locations were contemplated. FIG. 10 shows the mean and standard deviation of the AUC obtained following a random selection of test-locations. As shown in FIG. 10, randomly reducing the number of test points up to 15 does not significantly reduce the AUC in RP diagnosis based on the absolute mean deviation of LMCV. The AUC=0.90 suggests that the probability of LMCV to discriminate successfully a randomly selected RP patient from a randomly selected healthy subject is 0.9.

The individual reports for 3 RP patients are presented in FIGS. 11-13 to illustrate the pattern of recorded pupil response values compared with the results of subjective DA-GVF testing. Referring to FIGS. 11A-11F, the PPC, MCV and LMCV results for patient #30 in response to blue light and red light stimuli recorded for each of the 76 test points of the 16.2 degree VF are illustrated. Patient #30 had no light detection by DA-GVF. PPC and MCV parameters were lower than 5 SEs away from the mean of healthy subjects in 75 out of the 76 test points in response to blue light (FIGS. 10A and 10B). The LMCV parameter was higher than 5 SEs away from the mean of healthy subjects in 48 of the 76 test points (FIG. 10C).

Figure 11A:
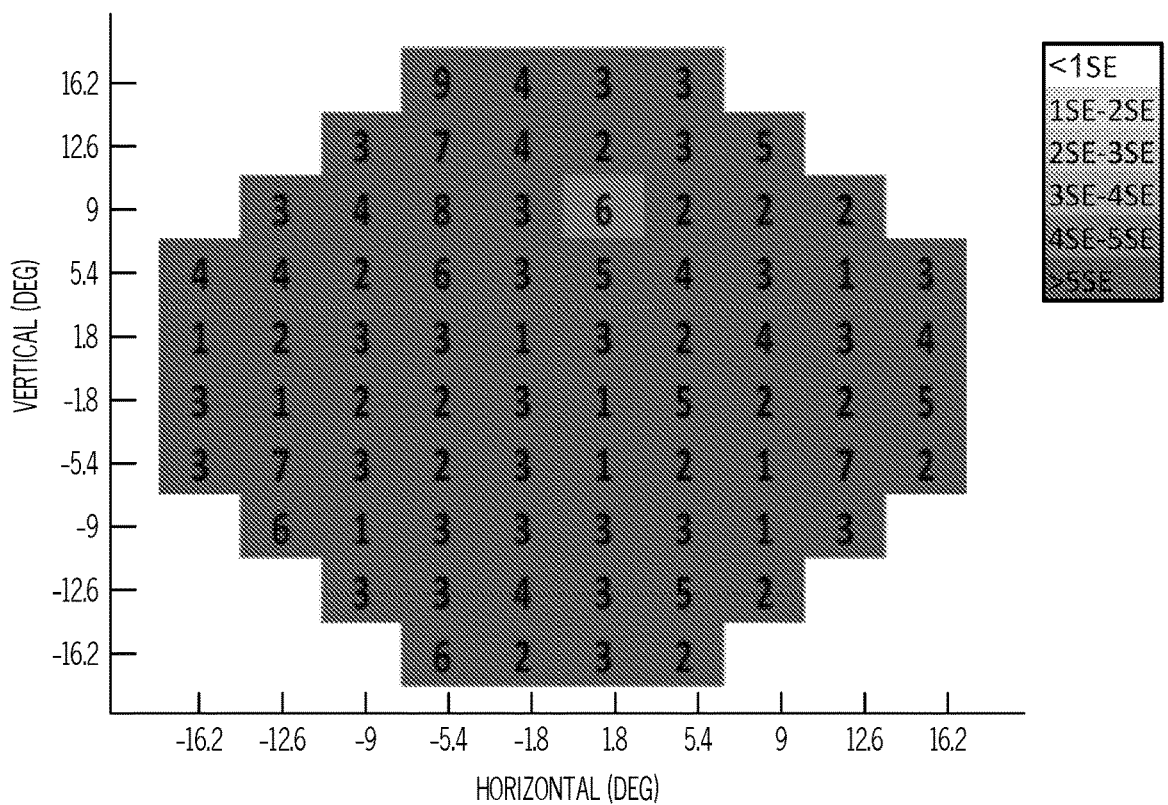
FIGS. 11A-11C illustrate PPC (FIG. 11A), MCV (FIG. 11B), and LMCV (FIG. 11C) results for patient #30 in response to blue light stimuli recorded in each of the 76 points of the 16.2 degree VF according to one or more embodiments shown and described herein.
Figure 11B:
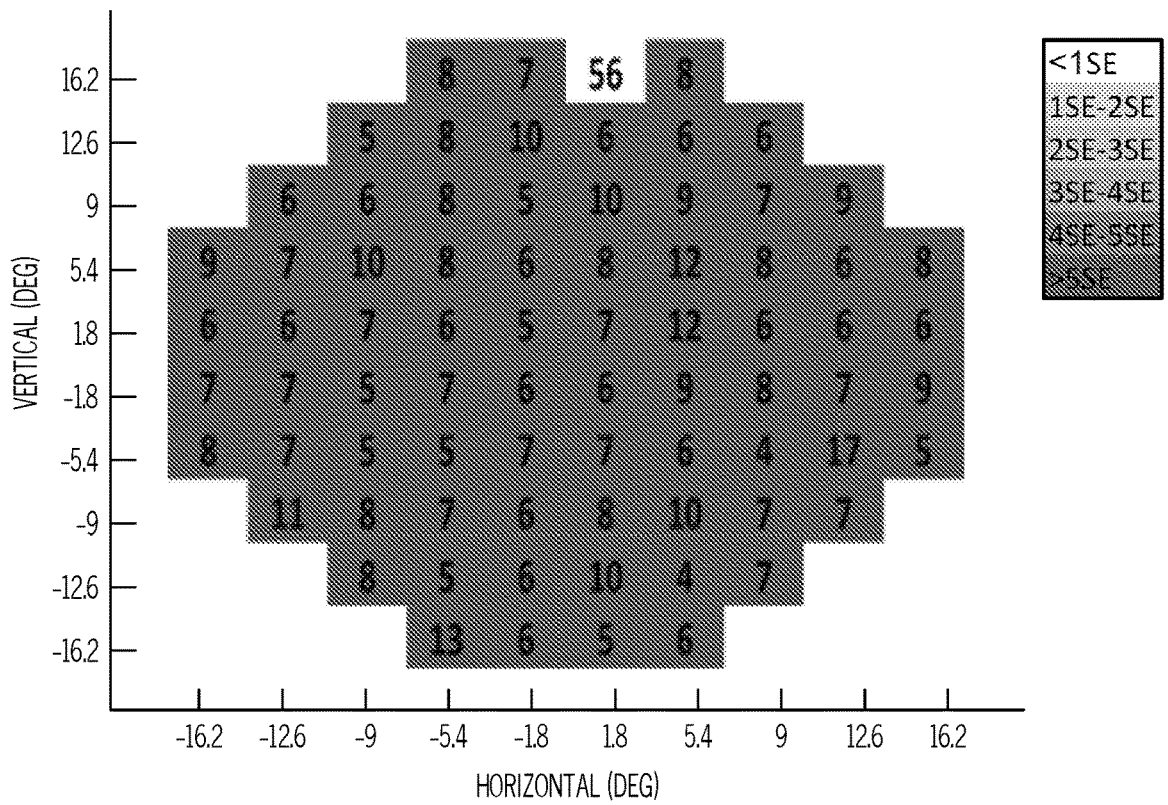
Figure 11C:
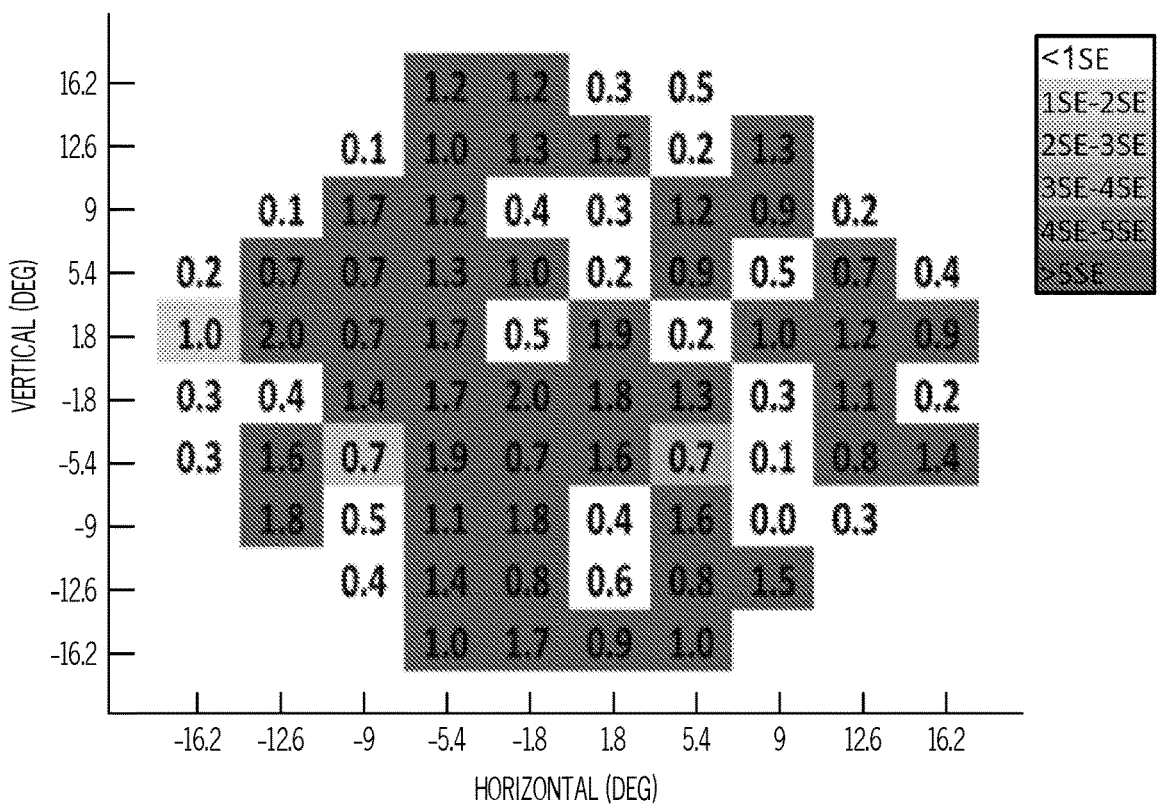
Figure 11D:
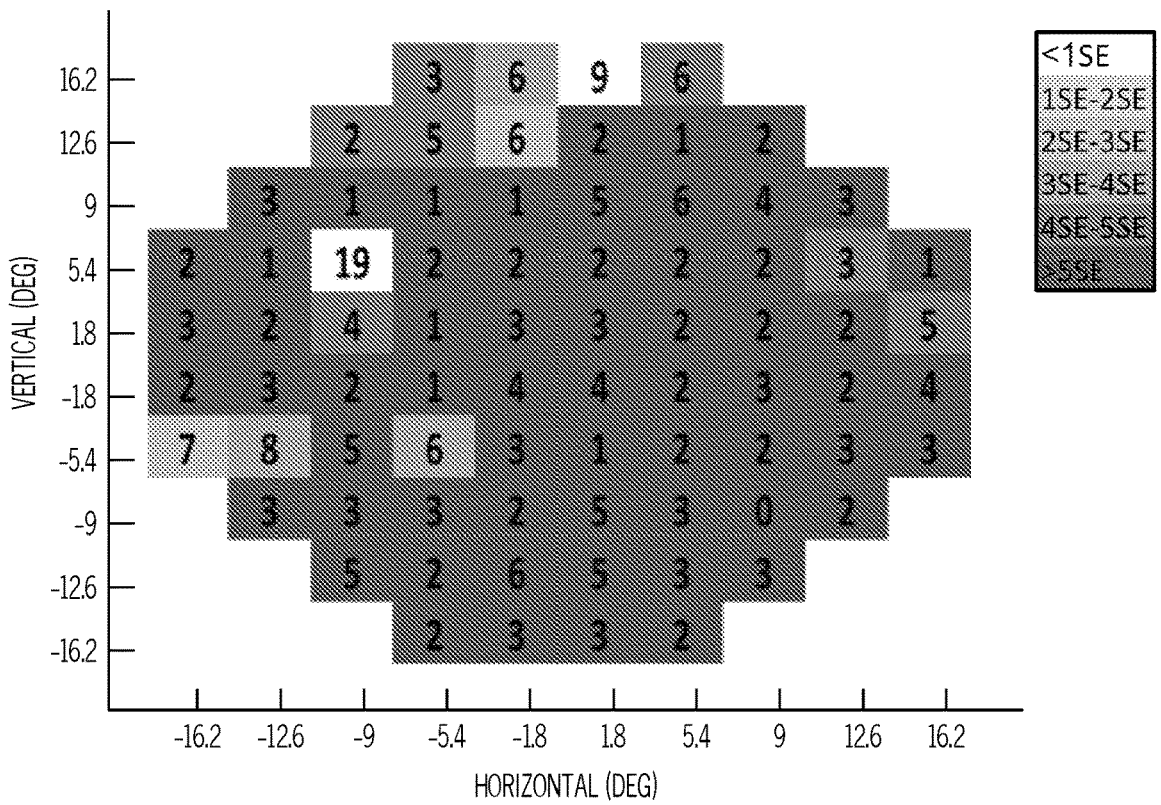
FIGS. 11D-11F illustrate PPC (FIG. 11D), MCV (FIG. 11E), and LMCV (FIG. 11F) results for patient #30 in response to red light stimuli recorded in each of the 76 points of the 16.2 degree VF according to one or more embodiments shown and described herein.
Figure 11E:
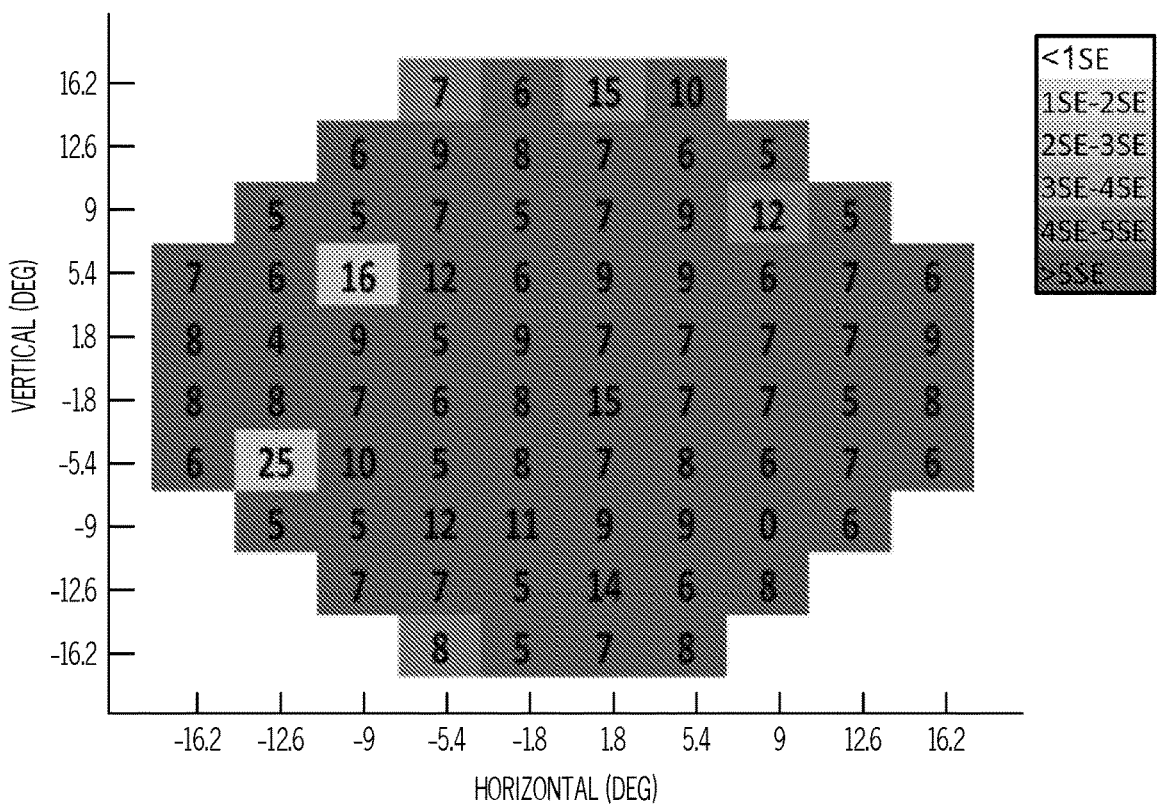
Figure 11F:
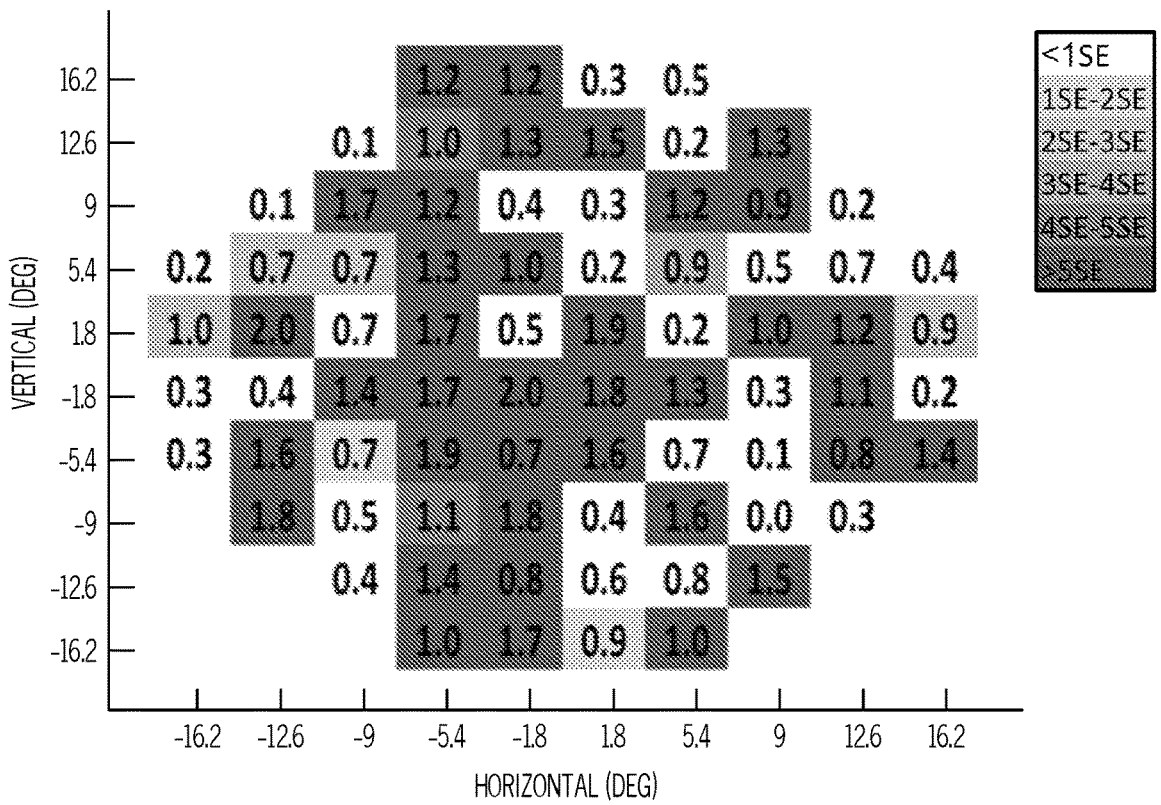

The pupil responses to red light were also significantly diminished throughout the VF, with 69 and 74 out of the 76 test points presenting PPC and MCV lower than 4 SEs away from the mean of healthy subjects (FIGS. 11D and 11E). The LMCV parameter was higher than 5 SEs away from the mean of healthy subjects in 38 test points (FIG. 11F). The mean absolute deviation in LMCV in response to the red light for this patient was the largest recorded in this study (0.47 sec).

Figure 12A:
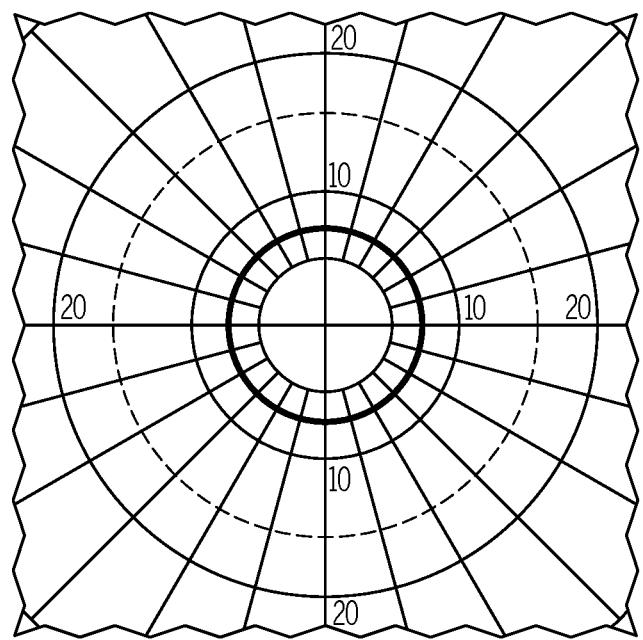
FIGS. 12A and 12E illustrate results of DA-GVF testing in patient #3, which results demonstrate the subjective VF for red light (FIG. 12A) and blue light (FIG. 12E) with the dashed line indicating the borders of the 16.2 degree VF according to one or more embodiments shown and described herein.
Figure 12E:
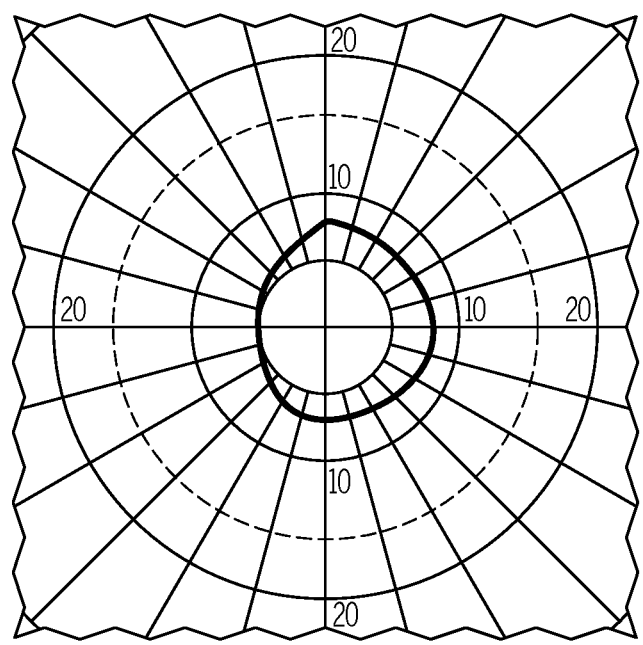
Figure 12B:
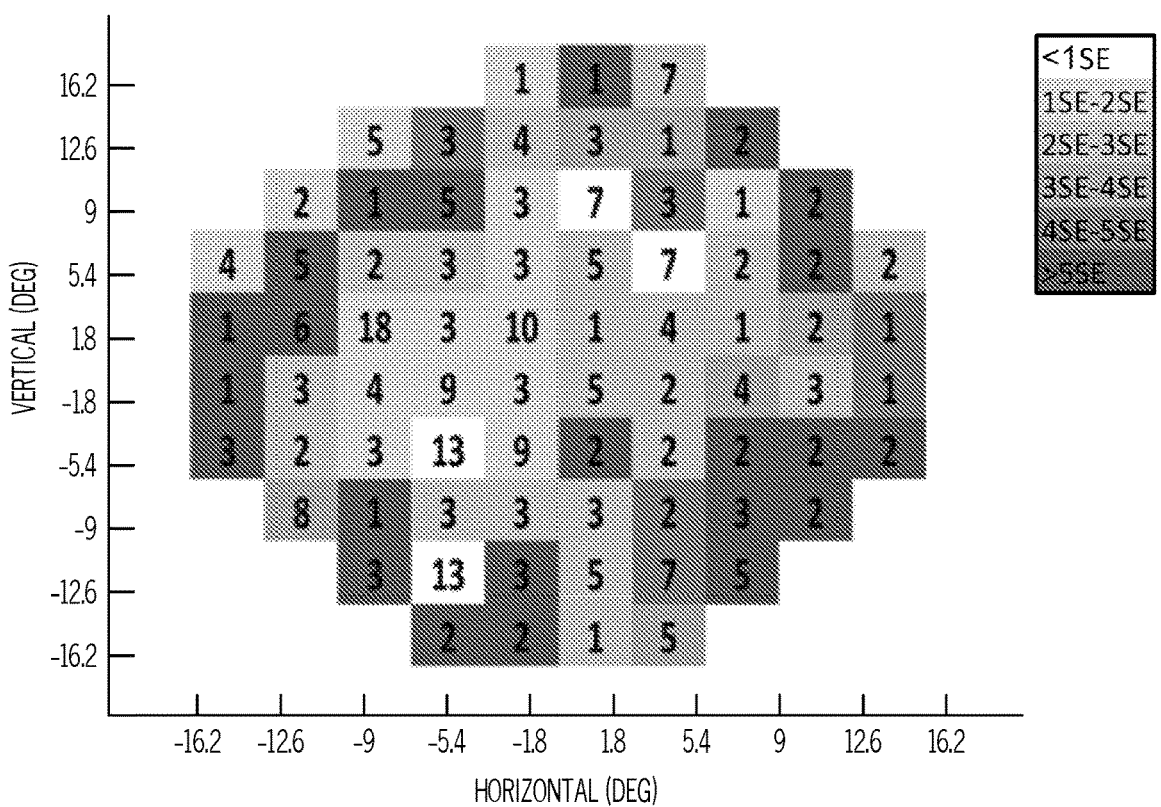
FIGS. 12B-12D illustrate PPC (FIG. 12B), MCV (FIG. 12C), and LMCV (FIG. 12D) of patient #3 in response to blue light stimuli recorded in each of the 76 points of the 16.2 degree VF according to one or more embodiments shown and described herein.
Figure 12F:
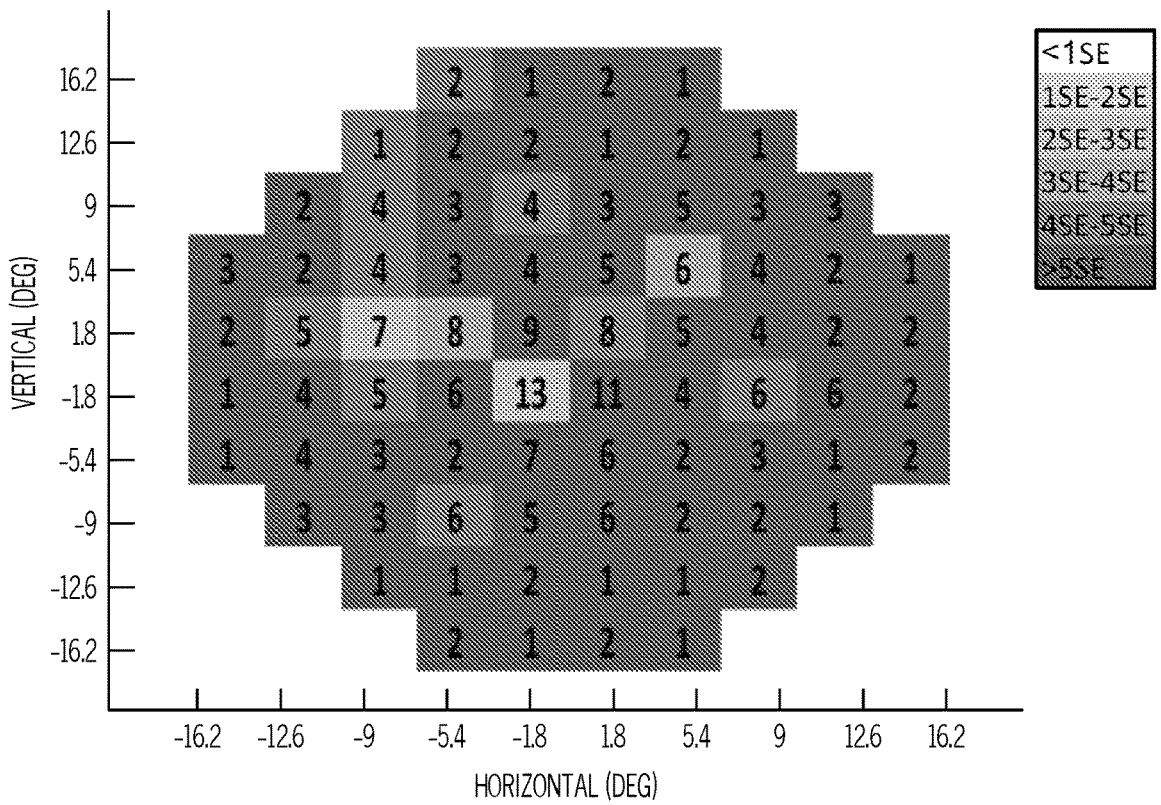
FIGS. 12F-12H illustrate PPC (FIG. 12F), MCV (FIG. 12G), and LMCV (FIG. 12H) of patient #3 in response to red light stimuli recorded in each of the 76 points of the 16.2 degree VF according to the one or more embodiments shown and described herein.
Figure 12C:
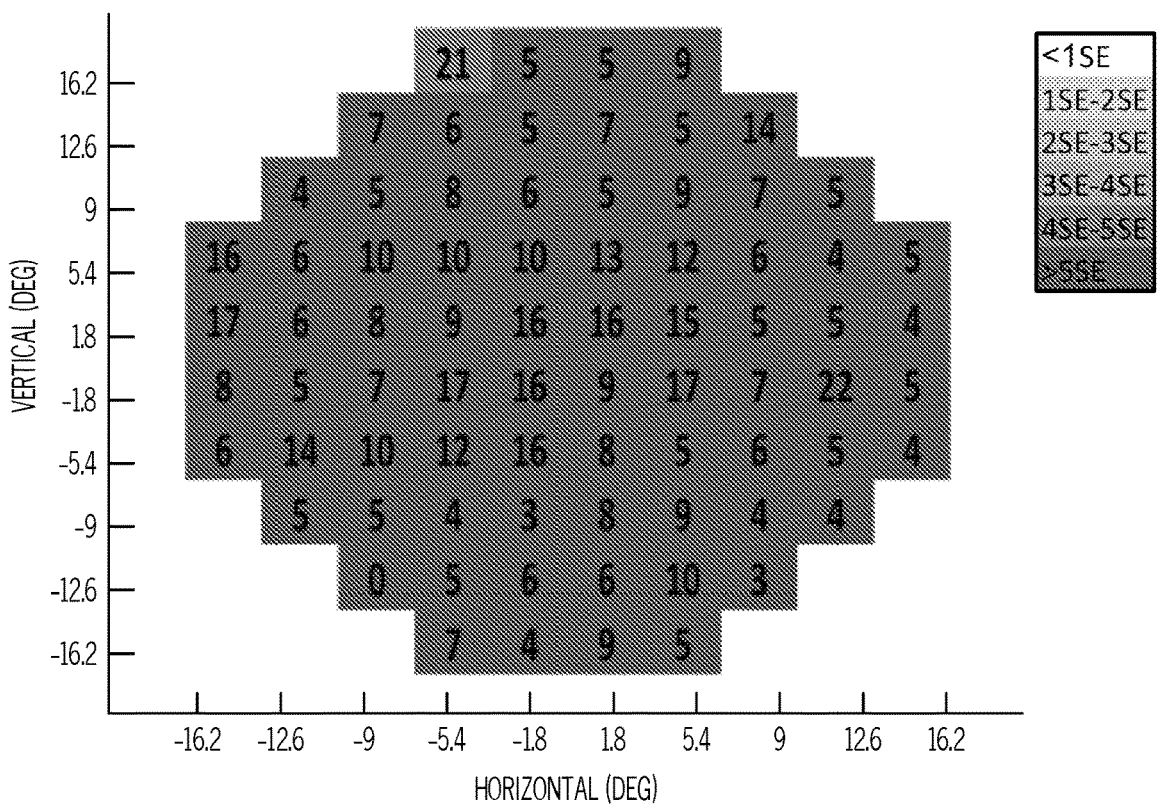
Figure 12G:
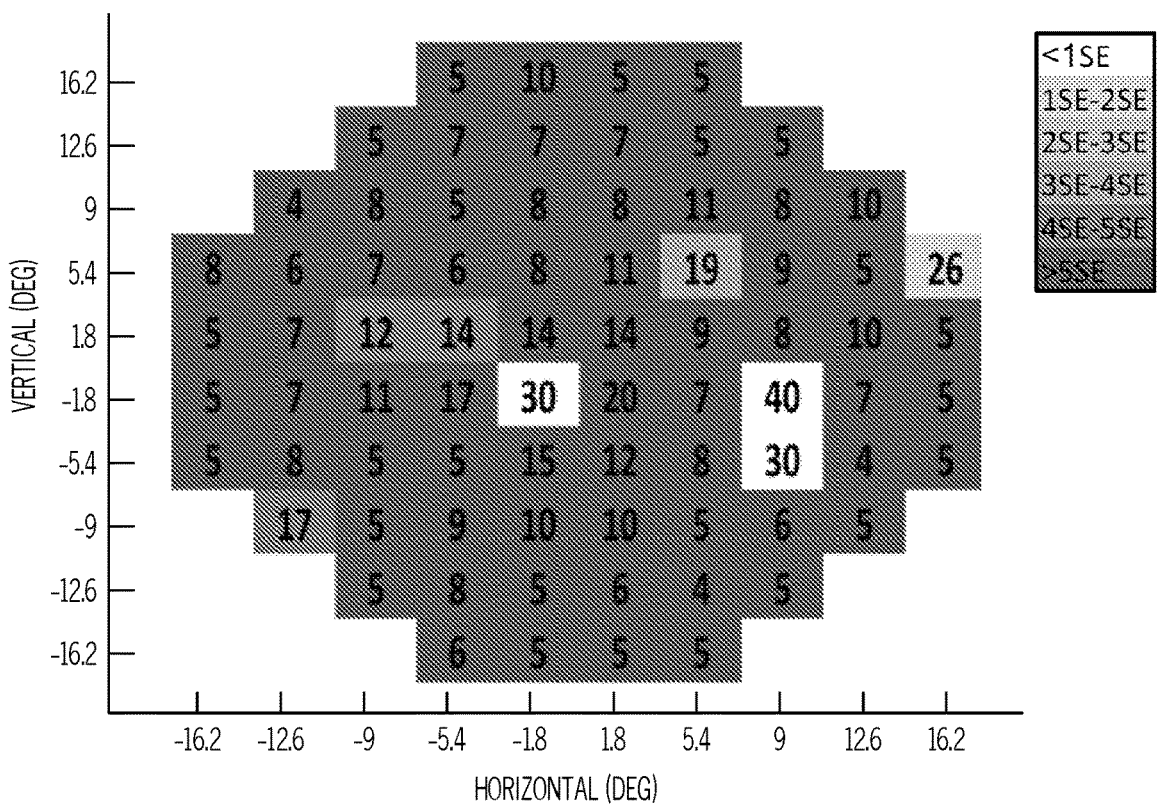
Figure 12D:
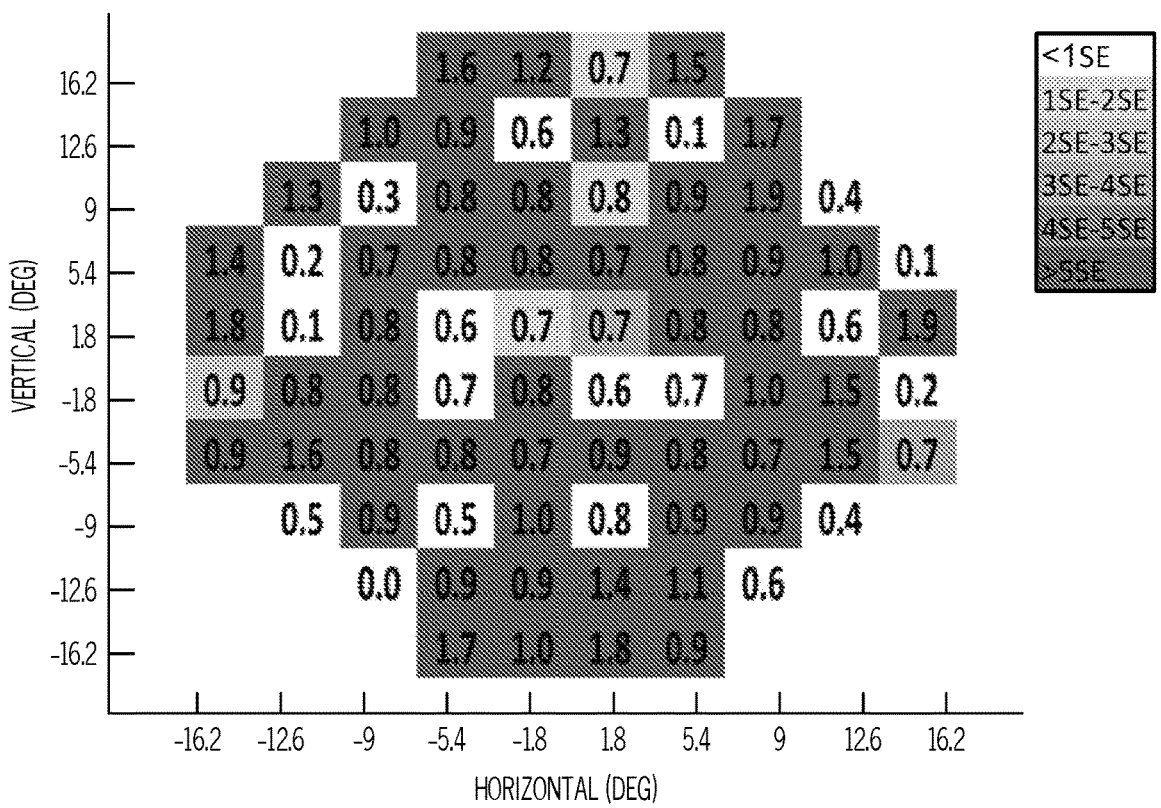

Referring to FIGS. 12A-12F, the PPC, MCV and LMCV results for patient #4 in response to blue light and red light stimuli recorded for each of the 76 test points of the 16.2 degree VF are illustrated. Patient #4 had "Tunnel vision" by DA-GVF (FIGS. 12A and 12E). The map of PPC parameter in response to blue light correlated with the DA-GVF map. Thus, in peripheral test point locations ("non-seeing" by DA-GVF), the PPC values were lower than 5 SEs away from the mean of healthy subjects, whereas in central locations PPC values were only 1-3 SEs lower than the mean of healthy subjects (FIG. 12B). The map of MCV demonstrated substantial reduction of MCV throughout the VF, with MCV lower than 4 SEs than mean of normal subjects in all 76 test points (FIG. 12C). The LMCV parameter was 1-2 SEs away from the mean of healthy in 20 test points, mostly in central locations (FIG. 12D).

Figure 12H:
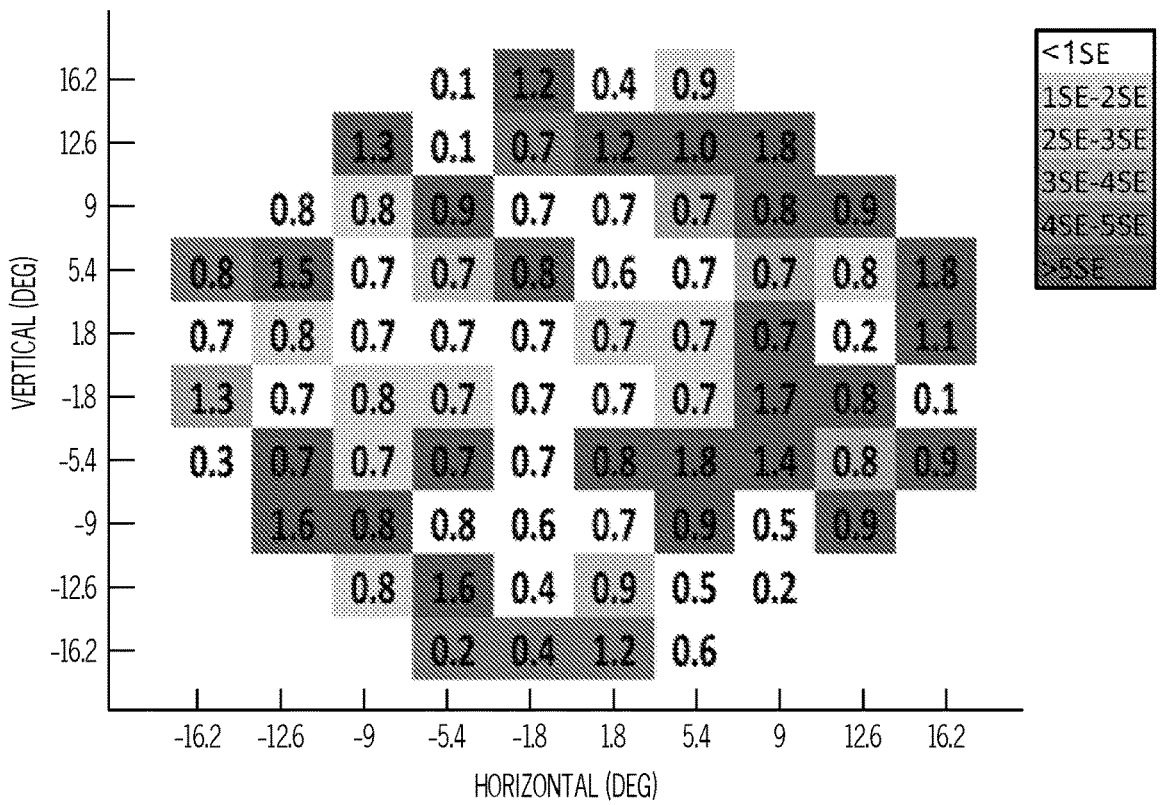
Figure 13A:
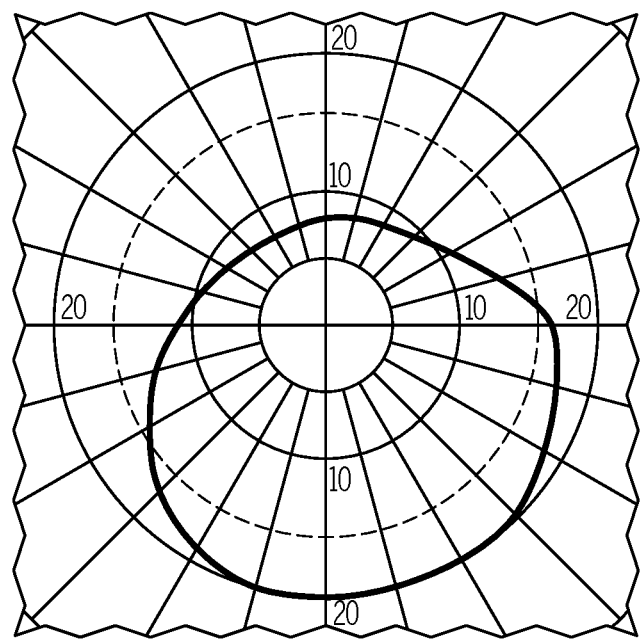
FIGS. 13A and 13E illustrate results of DA-GVF testing in patient #4, which results demonstrate the subjective VF for red light (FIG. 13A) and blue light (FIG. 13E) with the dashed line indicating the borders of the 16.2 degree VF according to one or more of the embodiments described herein.
Figure 13E:
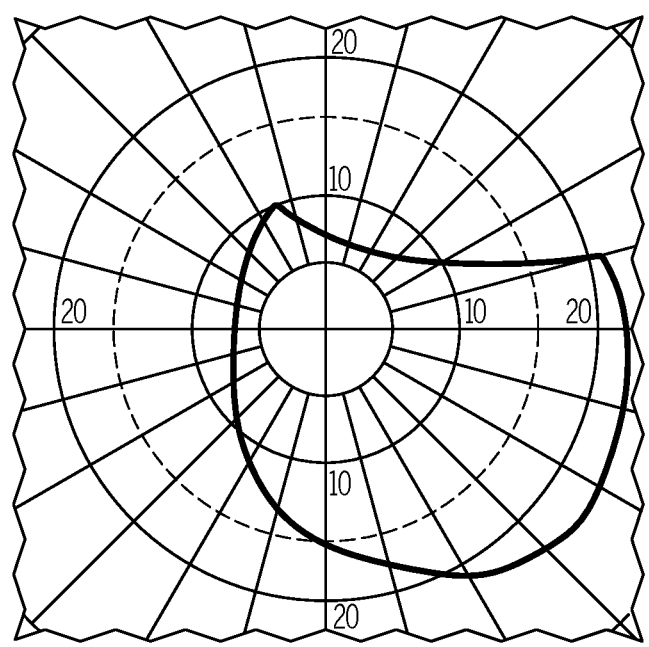
Figure 13B:
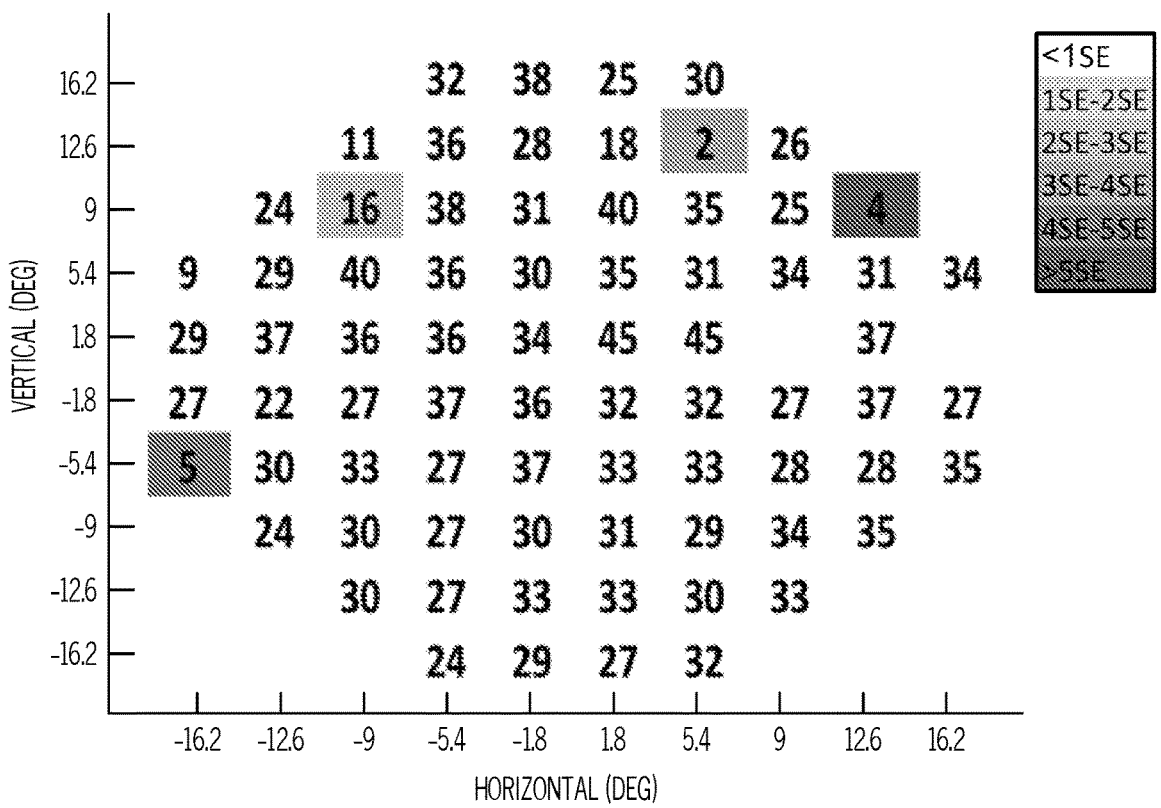
FIGS. 13B-13D illustrate PPC (FIG. 13B), MCV (FIG. 13C), and LMCV (FIG. 13D) of patient #4 in response to blue light stimuli recorded in each of the 76 points of the 16.2 degree VF according to one or more of the embodiments described herein.
Figure 13F:
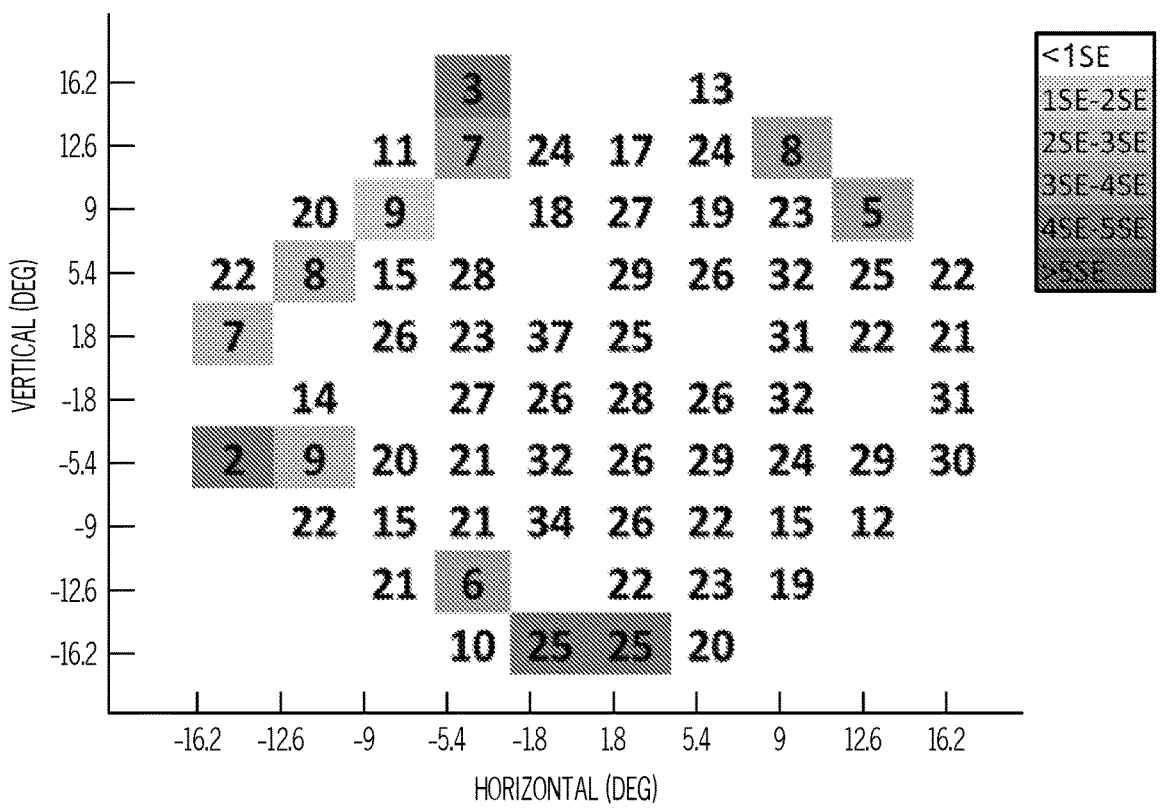
FIGS. 13F-13H illustrate PPC (FIG. 13F), MCV (FIG. 13G), and LMCV (FIG. 13H) of patient #4 in response to red light stimuli recorded in each of the 76 points of the 16.2 degree VF according to one or more of the embodiments described herein.
Figure 13C:
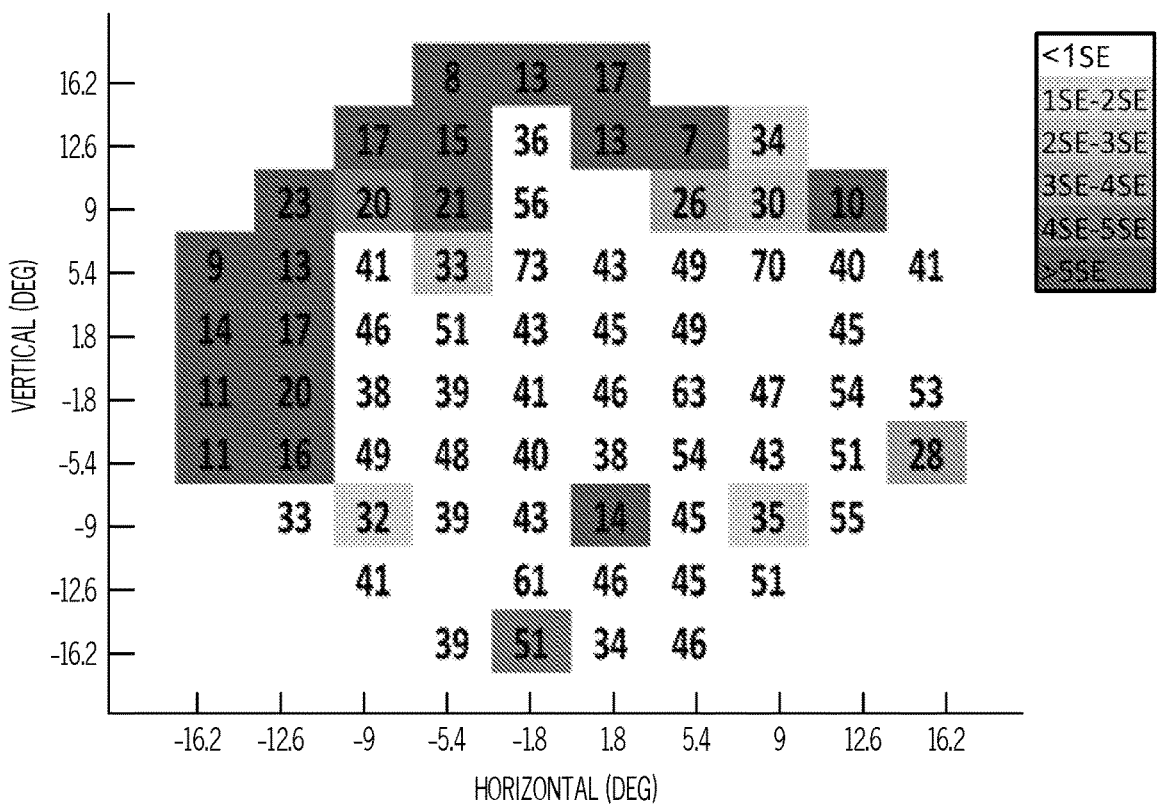
Figure 13G:
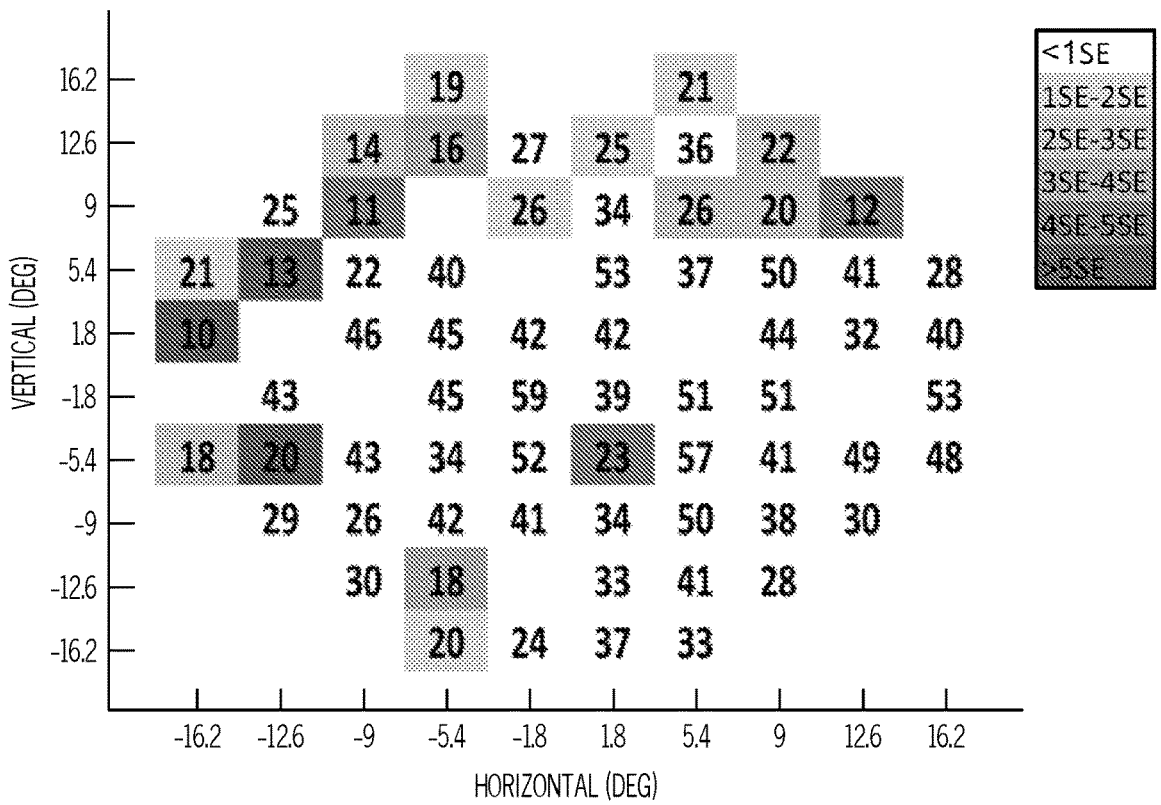
Figure 13D:
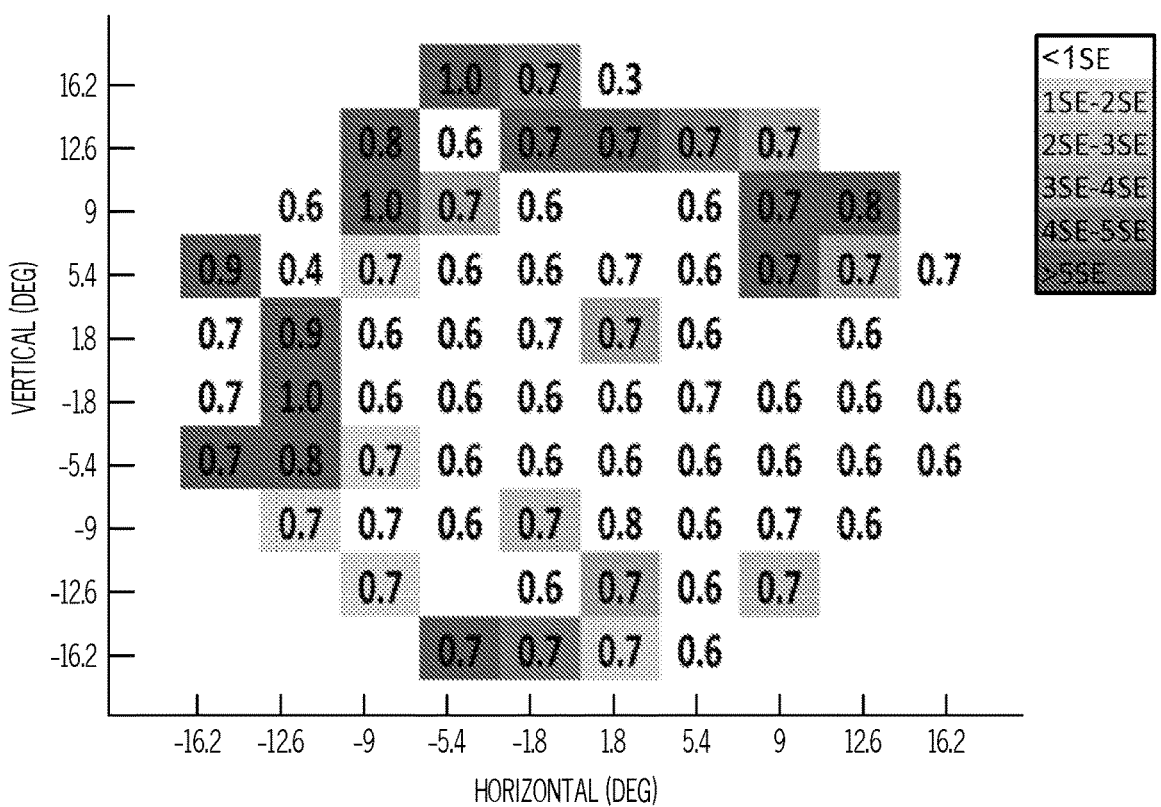
Figure 13H:
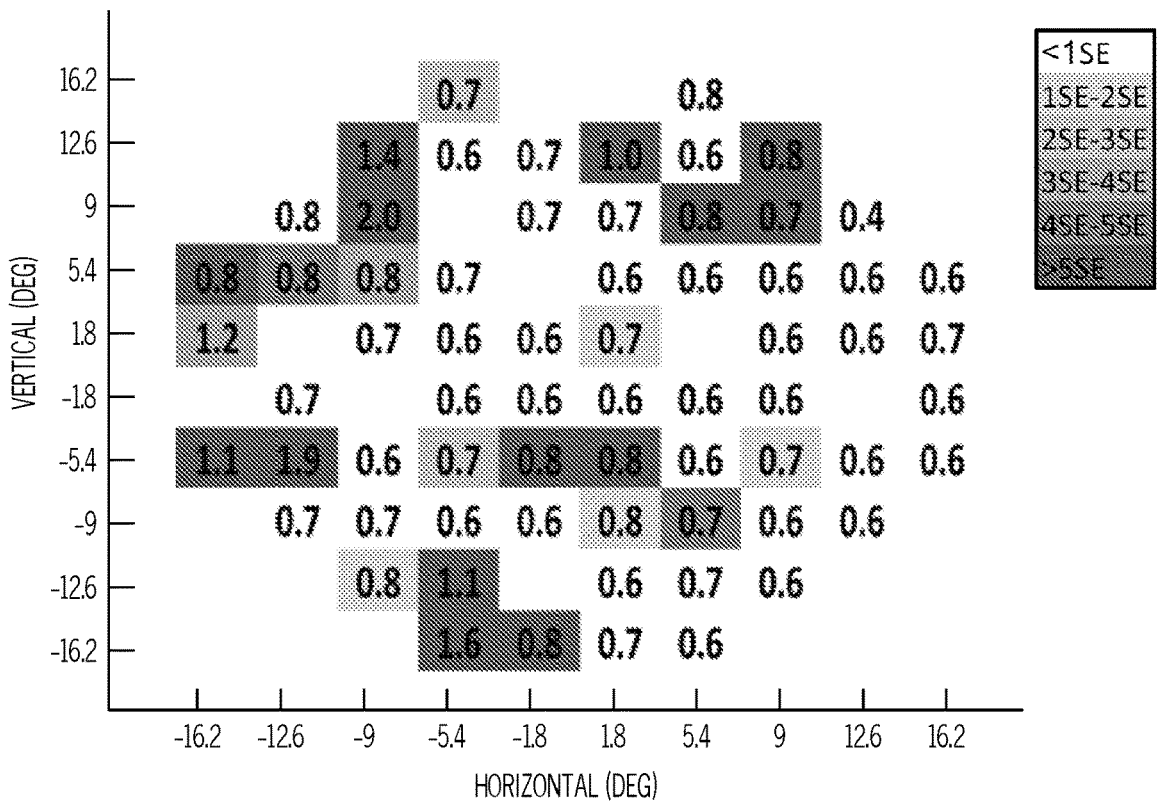

A similar "tunnel vision" pattern of pupil responses was obtained in response to the red light. The PPC and MCV parameters were equal to or only 1 SEs away from the mean of healthy subjects in 14 and 8 central test point locations, respectively, whereas PPC and MCV recorded in nearly all peripheral test points were over 5 SEs lower than the mean of normal subjects (FIGS. 12F and 12G). The LMCV parameter was close to normal (1-2 SEs away from the mean of healthy subjects) in 38 test points, most of them were located at the center of the VF (FIG. 12H). The mean absolute deviation in LMCV in response to the red light for this patient was intermediate (0.26 sec).

Referring to FIGS. 13A-13F, the PPC, MCV and LMCV results for patient #3 in response to blue light and red light stimuli recorded for each of the 76 test points of the 16.2 degree VF are illustrated. Patient #3 had a larger fraction of functional chromatic dark-adapted Goldman visual field (DA-GVF) than patient #4. Patient #3 had a significant functional portion of the 16.2 degree VF as determined by the subjective DA-GVF (FIGS. 12A and 12E). The pupil responses of this patient to both the red and blue light were equal to or 1-2 SE away from the mean of healthy subjects in majority of test points located in functional areas determined by the DA-GVF). The majority of areas that demonstrated substantially reduced PPC, MCV and longer LMCV compared to control (more than 2 SEs away from the mean of healthy subjects) were mostly located in "non-seeing" areas determined by the DA-GVF (FIG. 13). The mean absolute deviation in LMCV in response to the red light for this patient was small (0.16 sec).

It is contemplated that the system and method for performing objective perimetry and diagnosis of patients with retinitis pigmentosa and other ocular diseases is a valuable diagnostic tool for RP. The test point locations in which the parameters PPC and MCV were lower than four standard errors away from the mean of normal subjects, correlated with areas that were abnormal ("non-seeing") by dark adapted chromatic Goldmann. RP patients with severe VF loss presented more testing points that substantially differed from the mean of normal subjects as compared with patients with a moderate loss of VF, particularly in response to the blue light stimuli. Patients with some functional VF demonstrated reduced PLR particularly in peripheral test points and in response to the blue light stimuli. The pathology of RP is characterized by loss of rod function that exceeds the reduction of cone function and VF loss typically begins with peripheral VF constriction. The findings that pupil response to blue light in RP patients was more affected than the pupil response to red light stimuli strongly suggest that the pupil response to blue light measured by the chromatic multifocal pupillometer herein described is mediated mainly by rods, whereas the pupil response to red light is mediated mainly by cones. Hence, the chromatic multifocal pupillometer enables objective non-invasive assessment of the function of rods and cones at distinct locations of the VF.

Although the intensity of blue light stimulus used was 5 fold lower than the red light stimulus, the pupil responses to blue light stimulus in healthy subjects were stronger than the responses to red light stimuli in the same test locations (FIG. 4). These findings may be explained by the lower number of cones compared with rods in the human retina, the smaller receptive fields of cones and their lower sensitivity for light compared with rods.

The LMCV parameter recorded in response to red light appears to be is a useful tool for noninvasive and objective diagnosis of RP with an AUC of 0.97. The computer-based random clustering analysis suggested that shortening test duration may be possible with computational clustering, without reducing the sensitivity and accuracy of RP diagnosis. Thus, testing of only 15 test points in response to red light stimuli, which is predicted to take about 1 minute would enable diagnosis of RP with AUC of 0.9. Importantly the study group included RP patients at different stages of the diseases, some with substantial functional 16.2 degree VF (such as patient #3) and some patients that had no light detection (such as patient #30), further emphasizing the high specificity and sensitivity of the LMCV score. It is contemplated that using a chromatic multifocal pupillometer at a larger VF, e.g., about 30 degree, and a larger cohort of patients, and healthy subjects, would include a more thorough computational optimization for clustering, based on the results of random reduction of target locations.

The chromatic multifocal pupillometer device presented here was built to enable mapping of the central visual field. The choice to examine the device and method in RP patients was due to their pathology that facilitates the differentiation between cone and rod function. Examination of other ocular diseases may include patients with other blinding diseases, such as patients with macular degeneration and glaucoma, using a device that enables 30 degree VF testing.

It is further contemplated that including follow-up pupillometry and Optical Coherence Tomography (OCT) testing will allow analysis of longitudinal changes in pupillary response with respect to disease progression and in comparison with structural findings. The pupillometer test results were compared with DA-GVF, to enable evaluation of cone and rod responses. In other evaluations, a larger patient group may be tested and the pupillometer results may be compared with the more commonly used Humphrey perimetry.

Taken together, the results suggest direct correlation between "seeing" and pupil response function of the retina. The system and method described herein may facilitate objective perimetry and assessment of function of retinal photoreceptors with minimal patient cooperation and minimal technician training. The system and method is also predicted to be less stressful for tested subjects as they are unaware of the test results.

For the purposes of describing and defining the present invention, it is noted that reference herein to a characteristic of the subject matter of the present disclosure being a "function of" a parameter, variable, or other characteristic is not intended to denote that the characteristic is exclusively a function of the listed parameter, variable, or characteristic. Rather, reference herein to a characteristic that is a "function" of a listed parameter, variable, etc., is intended to be open ended such that the characteristic may be a function of a single parameter, variable, etc., or a plurality of parameters, variables, etc.

It is also noted that recitations herein of "at least one" component, element, etc., should not be used to create an inference that the alternative use of the articles "a" or "an" should be limited to a single component, element, etc. As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "about" are utilized herein to represent the inherent degree of uncertainty that may be attributed to any quantitative comparison, value, measurement, or other representation. The terms "substantially" and "about" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

The invention claimed is:

1. A method for determining a state of health of an eye using a multifocal pupillometer, wherein:
   the multifocal pupillometer comprises an ocular fixture, a testing compartment, at least one camera, and a controller;
   the testing compartment comprises a plurality of chromatic beam emitters arranged about a visual field of the pupillometer, the plurality of chromatic beam emitters are structurally configured to generate chromatic stimuli and to provide red and blue stimuli;
   the ocular fixture is positioned to facilitate exposure of light sensitive ocular structures of the eye to the chromatic stimuli of the plurality of chromatic beam emitters;
   the at least one camera is positioned to record temporal pupil contraction of the eye in response to the chromatic stimuli of the plurality of chromatic beam emitters;
   the controller controls emission wavelength, intensity, and duration of the chromatic beam emitters;

the controller processes temporal pupil contraction data recorded by the at least one camera to generate latency of maximal contraction velocity signals and percentage of pupil contraction or maximal contraction velocity signals representative of the eye positioned at the ocular fixture in response to the chromatic stimuli of the plurality of chromatic beam emitters at a plurality of locations in the visual field of the pupillometer; and
the method comprises
positioning a subject eye at the ocular fixture,
driving a selected first subset of the plurality of the chromatic beam emitters with the controller into a first illumination mode to determine an extent of a functional visual field of the subject eye from the percentage of pupil contraction or maximal contraction velocity signals, and
driving a selected second subset of the plurality of the chromatic beam emitters with the controller into a second illumination mode to determine the state of health of the subject eye as an objective function of mean absolute deviation in the latency of maximal contraction velocity signals between the plurality of locations in the visual field, wherein the controller selects and drives the second subset of the plurality of chromatic beam emitters based on the extent of the functional visual field determined in the first illumination mode.

2. The method of claim 1, wherein: the selected second subset of the plurality of chromatic beam emitters define an illuminated portion of the visual field of the pupillometer; and the illuminated portion of the visual field of the pupillometer does not extend substantially beyond the functional visual field of the subject eye.

3. The method of claim 1, wherein: the controller selects and drives the selected second subset of the plurality of chromatic beam emitters define an illuminated portion of the visual field of the pupillometer; and the illuminated portion of the visual field of the pupillometer is substantially congruent with the functional visual field of the subject eye.

4. The method of claim 1, wherein the testing compartment comprises:
a closed testing compartment comprising a viewing port disposed between/behind the ocular fixture and the plurality of chromatic beam emitters; or
an open testing compartment and the chromatic stimuli are generated in a dark room comprising a background luminance of less than about 30 cd/m$^2$.

5. The method of claim 1, wherein the testing compartment is provided in the form of a hemisphere bowl and the plurality of chromatic beam emitters are arranged about the hemisphere bowl.

6. The method of claim 1, wherein one or more of the plurality of chromatic beam emitters are structurally configured to generate the chromatic stimuli within a blue portion of a visible electromagnetic spectrum and one or more of the plurality of chromatic beam emitters are structurally configured to generate the chromatic stimuli within a red portion of the visible electromagnetic spectrum.

7. The method of claim 1, wherein driving the first subset of the plurality of chromatic beam emitters with the controller in the first illumination mode includes using the chromatic stimuli within a blue portion and a red portion of a visible electromagnetic spectrum.

8. The method of claim 7, wherein the chromatic stimuli within the red portion of the visible electromagnetic spectrum have an intensity between about 1 and about up to 1000 times greater than the chromatic stimuli within the blue portion of the visible electromagnetic spectrum.

9. The method of claim 1, wherein driving the second subset of the plurality of chromatic beam emitters with the controller in the second illumination mode includes using the chromatic stimuli within a blue portion and a red portion of a visible electromagnetic spectrum.

10. The method of claim 9, wherein the chromatic stimuli within the red portion of the visible electromagnetic spectrum have an intensity between about 1 and about up to 1000 times greater than the chromatic stimuli within the blue portion of the visible electromagnetic spectrum.

11. The method of claim 9, wherein:
the chromatic stimuli within the blue portion of the visible electromagnetic spectrum have a wavelength with a peak value lying in a range from about 450 nm to about 490 nm; and
the chromatic stimuli within the red portion of the visible electromagnetic spectrum have a wavelength with a peak value lying in a range from about 620 nm to about 700 nm.

12. The method of claim 1, wherein the controller is configured to activate one or more of the plurality of chromatic beam emitters for a duration between about 0.1 seconds and about 60 seconds.

13. A pupillometer comprising:
an ocular fixture;
a testing compartment;
at least one camera; and
a controller, wherein
the testing compartment comprises a plurality of chromatic beam emitters arranged about a visual field of the pupillometer,
one or more of the plurality of chromatic beam emitters are structurally configured to generate chromatic stimuli and configured to provide red and blue stimuli,
the ocular fixture is positioned to facilitate exposure of light sensitive ocular structures of an eye to the chromatic stimuli of the plurality of chromatic beam emitters,
the at least one camera is positioned to record temporal pupil contraction of the eye in response to the chromatic stimuli of the plurality of chromatic beam emitters,
the controller is configured to control emission wavelength, intensity, and duration of the plurality of chromatic beam emitters,
the controller is configured to process temporal pupil contraction data recorded by the at least one camera and to generate latency of maximal contraction velocity signals and percentage of pupil contraction or maximal contraction velocity signals representative of the eye positioned at the ocular fixture in response to the chromatic stimuli of the plurality of chromatic beam emitters at a plurality of locations in the visual field of the pupillometer; and
the controller is programmed to:
drive a first subset of the plurality of chromatic beam emitters into a first illumination mode to determine an extent of a functional visual field of a subject eye from the percentage of pupil contraction or maximal contraction velocity signals, and
drive a second subset of the plurality of chromatic beam emitters into a second illumination mode to determine a state of health of the subject eye as an objective function of mean absolute deviation in the latency of maximal contraction velocity signals between the plurality of locations in the visual field, wherein the controller is configured to select and drive a first subset of the plurality of chromatic beam emitters based on the extent of the functional visual field determined in the first illumination mode.

14. The pupillometer of claim 13, wherein the controller is configured to select and drive the second subset of the plurality of chromatic beam emitters to define an illuminated portion of the visual field of the pupillometer, wherein the illuminated portion of the visual field of the pupillometer does not extend substantially beyond the functional visual field of the subject eye.

15. The pupillometer of claim 13, wherein:
the controller is configured to select and drive the second subset of the plurality of chromatic beam emitters to define an illuminated portion of the visual field of the pupillometer; and the illuminated portion of the visual field of the pupillometer is substantially congruent with the functional visual field of the subject eye.

16. The pupillometer of claim 13, wherein the testing compartment comprises:
a closed testing compartment comprising a viewing port disposed between/behind the ocular fixture and the plurality of chromatic beam emitters; or
an open testing compartment and the chromatic stimuli are generated in a dark room comprising a background luminance of less than about 30 cd/m$^2$.

17. The pupillometer of claim 13, wherein the testing compartment is provided in the form of a hemisphere bowl and the plurality of chromatic beam emitters are arranged about the hemisphere bowl.

18. The pupillometer of claim 13, wherein the second subset of plurality of chromatic beam emitters with the controller in the second illumination mode includes using the chromatic stimuli within a blue portion and a red portion of a visible electromagnetic spectrum.

19. The pupillometer of claim 18, wherein the chromatic stimuli within the red portion of the visible electromagnetic spectrum have an intensity between about 1 and about up to 1000 times greater than the chromatic stimuli within the blue portion of the visible electromagnetic spectrum.

20. The pupillometer of claim 18, wherein:
the chromatic stimuli within the blue portion of the visible electromagnetic spectrum have a wavelength with a peak value lying in a range from about 450 nm to about 490 nm; and
the chromatic stimuli within the red portion of the visible electromagnetic spectrum have a wavelength with a peak value lying in a range from about 620 nm to about 700 nm.

* * * * *